US010837020B2

(12) United States Patent
Yanik et al.

(10) Patent No.: US 10,837,020 B2
(45) Date of Patent: Nov. 17, 2020

(54) INNATE IMMUNE SUPPRESSION ENABLES REPEATED DELIVERY OF LONG RNA MOLECULES

(75) Inventors: Mehmet Fatih Yanik, Watertown, MA (US); Matthew Angel, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 270 days.

(21) Appl. No.: 13/455,327

(22) Filed: Apr. 25, 2012

(65) Prior Publication Data

US 2012/0208278 A1  Aug. 16, 2012

Related U.S. Application Data

(62) Division of application No. 12/428,378, filed on Apr. 22, 2009, now abandoned.

(51) Int. Cl.
*C12N 15/85* (2006.01)
*C12N 15/67* (2006.01)
*C12N 15/113* (2010.01)

(52) U.S. Cl.
CPC ............ *C12N 15/67* (2013.01); *C12N 15/113* (2013.01); *C12N 15/1136* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 5,824,497 A | 10/1998 | Andrews et al. | |
| 6,602,713 B1 | 8/2003 | Wyatt | |
| 6,602,857 B1 | 8/2003 | Cowsert et al. | |
| 6,607,915 B1 | 8/2003 | Monia et al. | |
| 7,250,404 B2 | 7/2007 | Felgner et al. | |
| 2005/0053588 A1 | 3/2005 | Yin et al. | |
| 2005/0153910 A1 | 7/2005 | Matsumoto et al. | |
| 2005/0181385 A1 | 8/2005 | Linsley et al. | |
| 2006/0178334 A1* | 8/2006 | Rossi ............... | C12N 15/111 514/44 A |
| 2009/0093433 A1 | 4/2009 | Woolf et al. | |
| 2009/0286852 A1 | 11/2009 | Kariko et al. | |
| 2010/0189729 A1 | 7/2010 | Hoerr et al. | |
| 2011/0045001 A1 | 2/2011 | Klosel et al. | |
| 2012/0322865 A1 | 12/2012 | Rossi et al. | |
| 2014/0073053 A1 | 3/2014 | Yanik et al. | |

FOREIGN PATENT DOCUMENTS

| | | | |
|---|---|---|---|
| WO | WO-9612030 A1 * | 4/1996 | ........... C07K 14/005 |
| WO | WO 2001/59069 A1 | 8/2001 | |
| WO | WO2004/041172 A2 | 5/2004 | |
| WO | WO-2004/046320 A2 | 6/2004 | |
| WO | WO-2004/085654 A2 | 10/2004 | |
| WO | WO-2004098532 A2 | 11/2004 | |
| WO | WO-2009/065618 A2 | 5/2009 | |
| WO | WO 2010/129023 A9 | 11/2010 | |
| WO | WO 2012/122318 A2 | 9/2012 | |

OTHER PUBLICATIONS

Adamsen et al (International Journal of Oncology, 2007. vol. 31, pp. 1491-1500).*
Liu et al (Journal of Virology, 2007.vol. 81, No. 3, pp. 1401-1411).*
Alcami et al (Journal of Virology, 2000.. vol. 74, No. 23, pp. 11230-11239).*
Drews et al. (Biomaterials, 2012. vol. 33, pp. 4059-4068).*
Matthew Angel: Extended transient trasfection by repeated delivery of in vitro transcribed RNA, Sep. 2008, Archives Apr. 27, 2009.*
Alexopoulou, et al., "Recognition of Doublestranded RNA and Activation of NF-kappaB by Toll-Like Receptor 3," *Nature* 413: 732-738 (2001).
Bode et al., "Subversion of Innate Host Antiviral Strategies by the Hepatitis C Virus", *Archives of Biochemistry and Biophysics* 462: 254-265 (2007).
Bonehill et al., "Messenger RNA-Electroporated Dendritic Cells Presenting MAGE-A3 Simultaneously in HLA Class I and Class II Molecules," *J. Immunol.* 172: 6649-6657 (2004).
Cheung et al., "A pH-Sensitive Polymer that Enhances Cationic Lipid-Mediated Gene Transfer," *Bioconjug. Chem.* 12: 906-910 (2001).
Choi et al., "MyoD Converts Primary Dermal Fibroblasts, Chondroblasts, Smooth Muscle, and Retinal Pigmented Epithelial Cells Into Striated Mononucleated Myoblasts and Multinucleated Myotubes," *PNAS* 87 (1990).
Diebold et al., "Innate Antiviral Responses by Means of TLR7-Mediated Recognition of Single-Stranded RNA," *Science* 303: 1529-1531 (2004).
Feng et al., "PU.1 and C/EBP Alpha/Beta Convert Fibroblasts Into Macrophage-Like Cells," *Proc. Natl. Acad. Sci. USA* 105(16): 6057-6062 (2008).
Feng et al., "PU.1 and C/EBP•/• Convert Fibroblasts Into Macrophage-Like Cells," *PNAS* 105 (2008).
Gonzalez et al., "Selection of an Optimal RNA Transfection Reagent and Comparison to Electroporation for the Delivery of Viral RNA," *J. Virol. Methods* 145: 14-21 (2007).
Homung et al., "5'-Triphosphate RNA is the Ligand for RIG-1," *Science* 314: 994-997 (2006).

(Continued)

*Primary Examiner* — Celine X Qian
(74) *Attorney, Agent, or Firm* — Wolf, Greenfield & Sacks, P.C.

(57) ABSTRACT

The present invention relates in part to methods for suppressing the innate immune response of a cell to transfection with an exogenous nucleic acid, to methods for increasing expression of a protein encoded by an exogenous nucleic acid by repeated delivery of the exogenous nucleic acid to a cell, and to methods of changing the phenotype of a cell by differentiating, transdifferentiating or dedifferentiating cells by repeatedly delivering one or more nucleic acids that encode defined proteins. A method is provided for extended transient transfection by repeated delivery of an in vitro-transcribed RNA ("ivT-RNA") to a cell to achieve a high and sustained level of expression of a protein encoded by an ivT-RNA transcripts.

22 Claims, 15 Drawing Sheets

Specification includes a Sequence Listing.

(56) References Cited

OTHER PUBLICATIONS

Huangfu et al., "Induction of Pluripotent Stem Cells by Defined Factors is Greatly Improved by Small-Molecule Compounds," *Nat. Biotech.* (2008).
International Preliminary Report on Patentability for PCT/US2009/041453, dated Nov. 3, 2011.
International Search Report, PCT/US2009/041453, dated Apr. 22, 2009, 1-18.
Jessberger et al., "Directed Differentiation of Hippocampal Stem/Progenitor Cells in the Adult Brain," *Nature Neuroscience* 11(8): 888-893 (2008).
Jiang et al., "A Nucleolin-Binding 3' Untranslated Region Element Stabilizes Beta-Globin mRNA In Vivo," *Mol. Cell. Biol.* 26: 2419-2429 (2006).
Kariko et al., "Incorporation of Pseudouridine into mRNA Yields Superior Nonimmunogenic Vector With Increased Translational Capacity and Biological Stability, Journal," *The American Society of Gene Therapy* 16(11):1833-1840 (2008).
Kariko et al., "mRNA is an Endogenous Ligand for Toll-Like Receptor 3," *J. Biol. Chem.* 279: 12542-12550 (2004).
Kehat et al., "Human Embryonic Stem Cells Can Differentiate Into Myocytes with Structural and Functional Properties of Cardiomyocytes," *J. Clin. Invest.* 108:407-414 (2001).
Kim et al., "Oct4-induced Pluripotency in Adult Neural Stem Cells," *Cell*, 136(3): 411-419 (2009).
Kim et al., Pluripotent Stem Cells Induced from Adult Neural Stem Cells by Reprogramming with Two Factors, *Nature* 454 (2008).
Kozak et al., "Point Mutations Define a Sequence Flanking the AUG Initiator Codon that Modulates Translation by Eukaryotic Ribosomes," *Cell* 44:283-292 (1986).
Lafleur et al., "A Novel Type I Interferon Expressed in Human Keratinocytes," *J. of Biol. Chem.* 276(43) (2001).
Li et al., "Specification of Motoneurons from Human Embryonic Stem Cells," Nat. Biotechnol 23:215-221 (2005).
Liu et al., "Experimental Studies on the Differentiation of Fibroblasts into Myoblasts induced by MyoD Genes In Vitro," *International Journal of Biomedical Science* 4(1): 14-19 (2008).
Maherali et al., "Directly Reprogrammed Fibroblasts Show Global Epigenetic Remodeling and Widespread Tissue Contribution," *Cell Stem Cell.* 1 (2007).
Malone et al., "Cationic Liposome-Mediated RNA Transfection," *Proc. Natl. Acad. Sci USA* 86:6077-6081 (1989).
Melton et al., "Efficient In Vitro Synthesis of Biologically-Active RNA and RNA Hybridization Probes from Plasmids Containing a Bacteriophage SP6 Promoter," *Nucleic Acids Res.* 12:7035-7056 (1984).
Mikkelsen et al., "Dissecting Direct Reprogramming Through Integrative Genomic Analysis," *Nature* (2008).
Mockey et al., "mRNA Transfection of Dendritic Cells: Synergistic Effect of ARCA mRNA Capping with Poly(a) Chains in Cis and in Trans for a High Protein Expression Level," *Biochem. Biophys Res. Commun.* 340:1062-1068 (2006).
Neb Catalog 1995.
Okita et al., "Generation of Germline-Competent Induced Pluripotent Stem Cells," *Dept. of Stem Cell Biology, Institute for Frontier Medical Sciences*, Kyoto University, 448: 313-318 (2007).
Paterson et al., "Efficient Translation of Prokaryotic mRNAs in a Eukaryotic Cell-Free System Requires Addition of a Cap Structure," *Nature* 279: 692-696 (1979).
Perrier et al., "Derivation of Midbrain Dopamine Neurons from Human Embryonic Stem Cells," *Proc. Natl. Acad. Sci. USA* 101: 12543-12548 (2004).
Ponsaerts et al., "Highly Efficient mRNA-Based Gene Transfer in Feeder-Free Cultured H9 Human Embryonic Stem Cells," *Cloning Stem Cells* 6:211-216 (2004).
Prasad et al., "Quantitative Aspects of Endocytic Activity in Lipid-Mediated Transfections," *FEBS Lett* 579:2635-2642 (2005).
Reynolds et al., "Induction of the interferon response by siRNA is cell type and duplex length-dependent," *RNA* 12(6): 988-93 (2006).

Russell et al., "The Stability of Human Beta-Globin mRNA is Dependent on Structural Determinants Positioned Within Its 3' Untranslated Region," *Blood* 87: 5314-5323 (1996).
Saito et al., "Innate Immunity Induced by Composition-Dependent RIG-I Recognition of Hepatitis C Virus RNA," *Nature* 454: 523-527 (2008).
Sawai et al., "A Novel Method of Cell-Specific mRNA Transfection," *Mol. Genet. Metab.* 64: 44-51 (1998).
Schultz et al., "Differentiation of Human Embryonic Stem Cells to Dopaminergic Neurons in Serum-Free Suspension Culture," *Stem Cells* 22:1218-1238 (2004).
Shi et al., "A Combined Chemical and Genetic Approach for the Generation of Induced Pluripotent Stem Cells," *Cell Stem Cell.* 2 (2008).
Shin et al., "Human Motor Neuron Differentiation from Human Embryonic Stem Cells," *Stem Cells Dev* 14:266-269 (2005).
Stadtfeld et al., "Induced Pluripotent Stem Cells Generated Without Viral Integration" Science 322: 945-949 (2008).
Stepinski et al., "Synthesis and Properties of mRNAs Containing the Novel "Anti-Reverse" Cap Analogs 7-Methyl(3'-Omethyl) GpppG and 7-Methyl(3'deoxy)GpppG," 7:1486-1495 (2001).
Stewart et al., "Manipulation of Human Pluripotent Embryonal Carcinoma Stem Cells and the Development of Neural Subtypes," *Stem Cells* 21:248-256 (2003).
Tan et al., "Title" *Human Immunology*, 69: 32-40 (2008).
Van Tendeloo et al., "Highly Efficient Gene Delivery by mRNA Electroporation in Human Hematopoietic Cells: Superiority to Lipofection and Passive Pulsing of mRNA and to Electroporation of Plasmid cDNA for Tumor Antigen Loading of Dendritic Cells," *Blood* 98:49-56 (2001).
Wernig et al., "In Vitro Reprogramming of Fibroblasts into a Pluripotent ES-Cell-Like State," *Nature* 448 (2007).
Yoneyama et al., "The RNA Helicase RI:G-I has an Essential Function in Doublestranded RNA-Induced Innate Antiviral Responses," *Nat. Immunol.* 5: 730-737 (2004).
Yu et al., "Structural and Functional Analysis of an mRNP Complex that Mediates the High Stability of Human Beta-Globin mRNA," *Mol. Cell Biol.* 21:;5879-5888 (2001).
Zabner et al., "Cellular and Molecular Barriers to Gene Transfer by a Cationic Lipid," *J. Biol. Chem.* 270:18997-19007 (1995).
Zhou et al., "In Vivo Reprogramming of Adult Pancreatic Exocrine Cells β-Cells," *Nature* 455:627-632 (2008).
Zohra et al., "Effective Delivery with Enhanced Translational Activity Synergistically Accelerates mRNA-Based Transfection," *Biochem Biophys Res Commun* 358:373-379 (2007).
L. Martinez-Sobrido et al., Inhibition of the Type I Interferon response by the nucleoprotein of the prototypic arenavirus lymphocyctic choriomeningitis virus, Journal of Virology 80(18): 9192-9199 (2006).
Luo et al., Porcine reproductive and respiratory syndrome virus (PRRSV) suppresses interferon-beta production by interfering with the RIG-I signaling pathway, Molecular Immunology, 45(10): 2839-2846 (2008).
Zhang et al., Hepatitis C vius single-stranded RNA induces innate immunity via Toll-like receptor 7, Journal of Hepatology, 51(1): 29-38 (2009).
Matthew Angel et al., Innate immune suppression enables frequent transfection with RNA encoding reprogramming proteins, PLOS One, 5(7): e11756 (Jul. 23, 2010).
European Search Report for EP09843771.8 dated Jan. 21, 2013.
Waibler, et al., Vaccinia virus-mediated inhibition of Type 1 interferon responses is a multifactorial process involving the soluble Type 1 Interferon Receptor B18 and intracellular components, Journal of Virology 83(4): 1563-1571 (2009).
West et al., Upregulation of the TLR3 pathway by Kaposi's sarcoma-associated herpesvirus during primary infection. J Virol. Jun. 2008;82(11):5440-9. doi: 10.1128/JV1.02590-07. Epub Mar. 26, 2008.
Angel, Extended transient transfection by repeated delivery of in vitro-transcribed RNA. Massachusetts Institute of Technology Master's Thesis. Sep. 1, 2008; 1-56.

(56) References Cited

OTHER PUBLICATIONS

Barbalat et al., Nucleic acid recognition by the innate immune system. Annu Rev Immunol. 2011;29:185-214. doi: 10.1146/annurev-immunol-031210-101340.

Drusch et al., Efficient stabilization of bulk fish oil rich in long-chain polyunsaturated fatty acids. Eur J Lipid Sci Technol. 2008;110:351-359. doi: 10.1002/ejlt.200700195.

Ham, Clonal growth of mammalian cells in a chemically defined, synthetic medium. Proc Natl Acad Sci U S A. Feb. 1965;53:288-93.

Haynes et al., L-Glutamine or L-alanyl-L-glutamine prevents oxidant- or endotoxin-induced death of neonatal enterocytes. Amino Acids. May 2009;37(1):131-42.

Ishii et al., Innate immune recognition of nucleic acids: beyond toll-like receptors. Int J Cancer. Nov. 20, 2005;117(4):517-23.

Kariko et al., Generating the optimal mRNA for therapy: HPLC purification eliminates immune activation and improves translation of nucleoside-modified, protein-encoding mRNA. Nucleic Acids Res. Nov. 2011;39(21):e142. doi: 10.1093/nar/gkr695. Epub Sep. 2, 2011.

Liu et al., A novel chemical-defined medium with bFGF and N2B27 supplements supports undifferentiated growth in human embryonic stem cells. Biochem Biophys Res Commun. Jul. 21, 2006;346(1):131-9. Epub May 24, 2006.

Van Der Valk et al., Optimization of chemically defined cell culture media—replacing fetal bovine serum in mammalian in vitro methods. Toxicol In Vitro. Jun. 2010;24(4):1053-63. doi: 10.1016/j.tiv.2010.03.016. Epub Mar. 31, 2010.

Warren et al., Highly efficient reprogramming to pluripotency and directed differentiation of human cells with synthetic modified mRNA. Cell Stem Cell. Nov. 5, 2010;7(5):618-30. doi: 10.1016/j.stem.2010.08.012. Epub Sep. 30, 2010.

Zhou et al., Generation of induced pluripotent stem cells using recombinant proteins. Cell Stem Cell. May 8, 2009;4(5):381-4. doi: 10.1016/j.stem.2009.04.005. Epub Apr. 23, 2009. Erratum in: Cell Stem Cell. Jun. 5, 2009;4(6):581.

Opposition of EP application No. 009843771.8, dated Jan. 10, 2018, by Dr. Christian Müller.

Bowie et al., Viral evasion and subversion of pattern-recognition receptor signalling. Nat Rev Immunol. Dec. 2008;8(12):911-22. doi:10.1038/nri2436.

Brown et al., In vivo administration of lentiviral vectors triggers a type I interferon response that restricts hepatocyte gene transfer and promotes vector clearance. Blood. Apr. 1, 2007;109(7):2797-805.

Colamonici et al., Vaccinia virus B18R gene encodes a type I interferon-binding protein that blocks interferon alpha transmembrane signaling. J Biol Chem. Jul. 7, 1995;270(27):15974-8.

De Vries et al., Increased virus replication in mammalian cells by blocking intracellular innate defense responses. Gene Ther. Apr. 2008;15(7):545-52. doi: 10.1038/gt.2008.12. Epub Feb. 14, 2008.

Duinsbergen et al., Induced pluripotency with endogenous and inducible genes. Exp Cell Res. Oct. 15, 2008;314(17):3255-63. doi: 10.1016/j.yexcr.2008.06.024. Epub Jul. 9, 2008.

Jackson et al., Role of genes that modulate host immune responses in the immunogenicity and pathogenicity of vaccinia virus. J Virol. May 2005;79(10):6554-9.

Jessberger et al., Fate plasticity of adult hippocampal progenitors: biological relevance and therapeutic use. Trends Pharmacol Sci. Feb. 2009;30(2):61-5. doi: 10.1016/j.tips.2008.11.003. Epub Jan. 8, 2009.

Kim et al., Recombinant Vaccinia virus-coded interferon inhibitor B18R: Expression, refolding and a use in a mammalian expression system with a RNA-vector. PLoS One. Dec. 7, 2017;12(12):e0189308. doi:10.1371/journal.pone.0189308. eCollection 2017.

Quabius et al., Synthetic mRNAs for manipulating cellular phenotypes: an overview. N Biotechnol. Jan. 25, 2015;32(1):229-35. doi: 10.1016/j.nbt.2014.04.008. Epub May 9, 2014.

Reynolds et al., Rational siRNA design for RNA interference. Nat Biotechnol. Mar. 2004;22(3):326-30. Epub Feb. 1, 2004.

Sakurai et al., Innate immune response induced by gene delivery vectors. Int J Pharm. Apr. 16, 2008;354(1-2):9-15. Epub Jun. 16, 2007.

Takahashi et al., Induction of pluripotent stem cells from mouse embryonic and adult fibroblast cultures by defined factors. Cell. Aug. 25, 2006;126(4):663-76. Epub Aug. 10, 2006.

Yoshioka et al., Enhanced generation of iPSCs from older adult human cells by a synthetic five-factor self-replicative RNA. PLoS One. Jul. 27, 2017;12(7):e0182018. doi: 10.1371/journal.pone.0182018. eCollection 2017.

Zhu et al., Innate immune response to adenoviral vectors is mediated by both Toll-like receptor-dependent and -independent pathways. J Virol. Apr. 2007;81(7):3170-80. Epub Jan. 17, 2007.

Kariko et al., Impacts of nucleoside modification on RNA-mediated activation of toll-like receptors. Nucleic Acids In Innate Immunity. May 2008:171-88. doi: 10.1201/9781420068269.ch13.

Kariko et al., Naturally occurring nucleoside modifications suppress the immunostimulatory activity of RNA: implication for therapeutic RNA development. Curr Opin Drug Discov Devel. Sep. 2007;10(5):523-32.

Karpala et al., Immune responses to dsRNA: implications for gene silencing technology. Immunol Cell Biol. Jun. 1, 2005;83(3):211-6.

\* cited by examiner

FIG. 1

Embodiment of a HUSK ivT-RNA Transcript

5' m7G cap-2'-O-methylated second nucleotide/ stable 5'UTR with or without IRES/ strong Kozak / protein coding sequence (CDS) / stable 3'UTR / poly(A) tail 3'

INNATE IMMUNE SUPPRESSION ENABLES REPEATED DELIVERY OF LONG RNA MOLECULES

CROSS REFERENCE TO RELATED APPLICATIONS

This application is a divisional of U.S. Ser. No. 12/428,378, filed on Apr. 22, 2009, the entire contents of each of which is incorporated herein by reference.

BACKGROUND OF THE INVENTION

1. Field of the Invention

The present invention relates to cell transfection with nucleic acids encoding proteins or RNA molecules to be expressed by the cell.

2. Description of the Related Art

The possibility of using human embryonic stem (hES) cells as an unlimited source of tissue-specific cells for implantation into patients suffering from a wide range of diseases and injuries is quickly becoming a reality. Many debilitating diseases are characterized by the loss of a single type of tissue-specific cell (Parkinson's, dopaminergic neuron; multiple sclerosis, oligodendrocyte; type-1 diabetes, insulin-producing β-cells), and several recent studies, including a number of controlled clinical trials, have demonstrated that many of the effects of cell-type-specific diseases can be reversed to varying degrees by implanting cells of the missing cell type or related cell types into the affected region of the body[1-8]. Because many terminally differentiated cell types do not proliferate readily in culture, multipotent cells must first be expanded and then differentiated in vitro to produce these tissue-specific cells in the large quantities needed for implantation. For this reason, the establishment of cultures of human ES cells that proliferate indefinitely and can differentiate into any cell type, marked a major milestone in the development of new cell-replacement therapies.

However, developing protocols for the in vitro differentiation of hES cells into pure populations of tissue-specific cells for both screening and regenerative-medicine applications has proved challenging.[9-14]. The available protocols produce cultures that contain undesirable cell types and markers needed for efficient purification of many tissue-specific cell types remain to be discovered. A new technology is needed to direct the differentiation of stem cells into any desired cell type with high efficiency, and also to cause differentiated cells to transdifferentiate or dedifferentiate into desired cell types.

Cell type is determined by the epigenome, the set of chromatin modifications and other factors that establish the degree to which each of a cell's genes is expressed, and that can be passed to daughter cells during mitosis.[15-18, 27-30] The epigenetic marks that collectively determine cell type are not permanent,[19-21], but are written and erased both during germ-cell formation and early development,[22-26] and also throughout the life of an adult. The differentiation that occurs in these stem-cell niches and in embryonic stem cells is controlled by extracellular cues that initiate cascades of intracellular signalling, which ultimately result in an epigenetic transition that selectively silences some genes while activating others.

Rather than screening libraries of small molecules for compounds that increase the efficiency of specific transitions that cells undergo as they differentiate in culture, a method of directly changing the cell's gene-expression program by transiently increasing expression of known factors that maintain the target-cell phenotype is needed. While RNA transfection is able to transiently increase expression of an ivT-RNA-encoded protein, no technique exists to maintain that high level of initial expression for more than a few hours or through multiple rounds of cell division without genetically modifying the cell.

Thus there is a need for techniques that will enable sustained expression of proteins encoded by ivT-RNA for several days, and in many cases for multiple generations, i.e. for more than one cell cycle using either synchronized or unsynchronized cells, to alter the cell's protein expression, which in turn would enable regulation of the gene-expression program and ultimately the cell phenotype.

FIGURE LEGENDS

The present invention is illustrated by way of example, and not by way of limitation, in the figures of the accompanying drawings and in which:

FIG. 1 provides a diagram of a HUSK ivT-RNA embodiment of the invention.

FIG. 2A depicts the intracellular stability of a HUSK ivT-RNA of the invention. MRC-5 fibroblasts were transfected with 2 µg of HUSK Transcript A or F or full-length Transcript A, and the intracellular concentration of each transcript was measured 2, 4, 12, and 24 hours after transfection. GAPDH was used as a loading control. Exponential regressions are shown for the HUSK-transcripts (solid lines) and the full-length-transcript (dashed line). Error bars show the pooled standard deviation of replicate samples.

FIG. 2B provides a diagram of MRC-5 fibroblasts pre-transfected with an siRNA cocktail targeting IFNB1, EIF2AK2, STAT2, and TLR3 (see text and methods) then co-transfected with 0.5 µg Lin28 ivT-RNA and additional siRNA at time 0. After the cells had attached, 200 µg/mL RNase A was added to the culture medium to degrade extracellular RNA. Cells were lysed at the indicated times, and the amount of Lin28 ivT-RNA was measured by RT-PCR using primers specific to the exogenous transcript. An exponential regression (black line, $R^2=0.96$) is shown. GAPDH was used as an endogenous control. Error bars show the standard deviation of replicate samples FIG. 3 A provides an example of the time-evolution of expression of translated protein EAQ following transfection with a HUSK ivT-RNA. Transcripts A, B, or F were delivered to MRC-5 fibroblasts by electroporation, and whole-cell lysates were prepared at the indicated times. A western blot was performed to measure the time-evolution of expression of the encoded proteins (see methods). A sample of cells that normally express the encoded proteins (H9 human embryonic stem cells) was used for comparison. β-actin (ACTB) was used as a loading control.

FIG. 3B provides an example of a more detailed protein expression time course and includes data showing the dose-response of protein expression after transfection with a HUSK ivT-RNA of the invention. MRC-5 fibroblasts were transfected with the indicated HUSK ivT-RNA, and whole-cell lysates were prepared at the indicated times. Proteins were detected by western blot.

FIG. 4 provides a bar graph comparing the innate-immune response elicited by different RNA transcripts. A: MRC-5 fibroblasts were transfected with 2 µg of HUSK Transcript A, B, or F of the invention, or full-length Transcript A, and the level of IFNB1 expression was measured after 24 hours. GAPDH was used as a loading control. Error bars show the pooled standard deviation of replicate samples. B: The transfected cells were monitored for several days and estimates of confluency were made at the indicated times. Data points are connected for clarity.

FIG. 5 depicts the cytostatic effect of transfection with a HUSK ivT-RNA HUSK ivT-RNA of the invention on MRC-5 fibroblasts transfected with 200 nM TP53 siRNA as indicated; two days later, the cells were suspended by trypsinization and electroporated with 3.5 µg HUSK ivT-RNA or 3.5 µg HUSK ivT-RNA and 200 nM TP53 siRNA as indicated. Only the cells that received siRNA on day 0 received additional siRNA on day 2. Data points are connected for clarity.

FIG. 6 provides a bar graph showing the innate-immune-related gene expression pattern after transfection with a HUSK ivT-RNA of the invention measured by quantitative RT-PCR 24 hours after transfection with HUSK ivT-RNA compared to mock-transfected cells. GAPDH was used as a loading control. Error bars show the pooled standard deviation of replicate samples.

FIG. 7 provides a series of bar graphs showing gene expression after interferon-β knockdown. A: MRC-5 fibroblasts were pre-transfected with IFNB1 siRNA, and then co-transfected with a HUSK ivT-RNA of the invention and siRNA two days later. Gene expression was measured 24 hours after the second transfection. B: MRC-5 fibroblasts were co-transfected with a HUSK ivT-RNA of the invention and IFNB1 siRNA, and the expression of TLR3, RARRES3, and IFNB1 was measured after 24 hours. Error bars show the pooled standard deviation of replicate samples.

FIG. 8 shows cell proliferation after interferon-β knockdown. MRC-5 fibroblasts were transfected with the indicated siRNA on day 0, and then co-transfected with 2.5 µg a HUSK ivT-RNA of the invention and siRNA on day 3. A,B: The expression of IFNB1 and TP53 was measured 24 hours after the second transfection. GAPDH was used as a loading control. Error bars show the pooled standard deviation of replicate samples. C: The confluency of each dish of cells was estimated at the indicated times. As in the experiment described in FIG. 5, the cells that received no HUSK ivT-RNA (diamonds) recovered quickly after the second electroporation, while the cells that received HUSK ivT-RNA (squares) exhibited proliferation delayed by approximately 48 hours. Also as before, TP53 knockdown (triangles, circles) shortened the recovery time by about half. However, IFNB1 knockdown (crosses, circles) had little or no effect on proliferation. Data points are connected for clarity.

FIG. 9 shows the effect of the knockdown of genes involved in the innate-immune response where (1). MRC-5 fibroblasts were pre-transfected with the indicated siRNAs (200 nM by electroporation), and then co-transfected with both siRNA and 2.5 µg a HUSK ivT-RNA of the invention 48 hours later. Gene expression was measured 24 hours after the second transfection, and is shown relative to mock-transfected cells. A: Gene expression of TLR3, STAT2, VISA, TBK1, and IRF3 was measured after knocking down each gene. B: Gene expression of TLR3, TICAM1, and TICAM2 was measured after combined knockdown of all three genes. C: IFNB1 expression of cells transfected with the indicated siRNAs. D: The confluency of transfected cells was estimated at the indicated times. Proliferation of cells transfected with siRNAs targeting genes other than STAT2 was indistinguishable from the no-siRNA control. Error bars in A-C show the pooled standard deviation of replicate samples. Data points in D are connected for clarity.

FIG. 10 shows the effect of knockdown of genes involved in the innate-immune response where (2). A,B: MRC-5 fibroblasts were transfected and gene expression was measured as in the previous FIG. C: The confluency of transfected cells was estimated at the indicated times. Proliferation of cells transfected with siRNAs targeting genes other than EIF2AK2 was indistinguishable from the no-siRNA control. Differences in post-transfection confluency (day 0 and day 2+) between this and the previous experiment are the result of different plating densities after electroporation. Error bars in A-B show the pooled standard deviation of replicate samples. Data points in C are connected for clarity.

FIG. 11A shows gene expression after combined knockdown of innate-immune-related genes where MRC-5 fibroblasts were transfected with siRNA Mix 1 (400 nM TP53, 200 nM STAT2, and 200 nM EIF2AK2) or siRNA Mix 2 (400 nM TP53, 200 nM STAT2, 200 nM EIF2AK2, 00 nM IFNB1, 200 nM TLR3, and 200 nM CDKN1A) on day 0, and then transfected with 0.5 µg HUSK Transcript B or F of the invention and additional siRNA after 48. Gene expression was measured 24 hours after the second transfection. GAPDH was used as a loading control. Error bars show the pooled standard deviation of replicate samples.

FIG. 11B shows the response of MRC-5 fibroblasts that were transfected twice with 0.5 µg Lin28-encoding a HUSK ivT-RNA of the invention at a 48-hour interval. Samples of cells transfected with RNA (gray circles) and mock-transfected cells (black squares) were trypsinized and counted at the indicated times. Data points and error bars represent the mean and standard error of two independent experiments. Data points are connected for clarity.

FIG. 11C shows MRC-5 fibroblasts and CCD-1109Sk fibroblasts that were transfected as in (11B), but mock-transfected on day 2 and transfected on day 4 with 0.5 µg of either Lin28 or MyoD1-encoding HUSK ivT-RNA. Gene expression was measured by RT-PCR 24 hours after the second transfection (day 5). Values are given relative to mock-transfected cells.

FIG. 11D shows cells that were transfected as in (11B), but with a cocktail of siRNA targeting IFNB1, EIFAK2, STAT2, and TLR3 on day 2, and 0.5 µg of either Lin28 or MyoD1-encoding HUSK ivT-RNA and additional siRNA on day 4. Gene expression was measured 24 hours after the second transfection (day 5). Values are given relative to cells that received no siRNA. GAPDH was used as an endogenous control. Error bars show the standard deviation of replicate samples.

FIG. 12 shows the amount of cell proliferation after repeated transfection with a HUSK ivT-RNA of the invention. A: MRC-5 fibroblasts were transfected with siRNA Mix 1 (400 nM TP53, 200 nM STAT2, and 200 nM EIF2AK2) or siRNA Mix 2 (400 nM TP53, 200 nM STAT2, 200 nM EIF2AK2, 200 nM IFNB1, 200 nM TLR3, and 200 nM CDKN1A) on day 0, and then transfected with 0.5 µg HUSK Transcript B on days 2, 3, and 4. Additional siRNA was included on days 2 and 4. After each transfection, approximately 10-15% of the cells were reserved for protein and RNA analysis, and the rest were plated in 10 cm dishes. The confluency of each dish was estimated at the indicated times. B: Cells were transfected as in A, but with 0.5 µg HUSK Transcript F, and no transfection was performed on day 3. Data points are connected for clarity.

FIG. 13A shows the response of MRC-5 fibroblasts that were pre-transfected with a cocktail of siRNAs targeting IFNB1, EIF2AK2, STAT2, and TLR3 before being transfected five times with 0.5 µg Lin28-encoding HUSK ivT-RNA and additional siRNA at 48-hour intervals. Cells were lysed at the indicated times, and the amount of Lin28 protein in each sample was assessed by western blot. ACTB was used as a loading control.

FIG. 13B shows the level of mature let7a miRNA relative to the level in mock-transfected cells measured 18 hours after transfection. Smoothed lines are drawn through data points corresponding to cells that were transfected once (solid line) and five times (dashed line). U47 RNA was used as an endogenous control. Error bars show the standard error of replicate samples.

DEFINITIONS

Figure 2A:
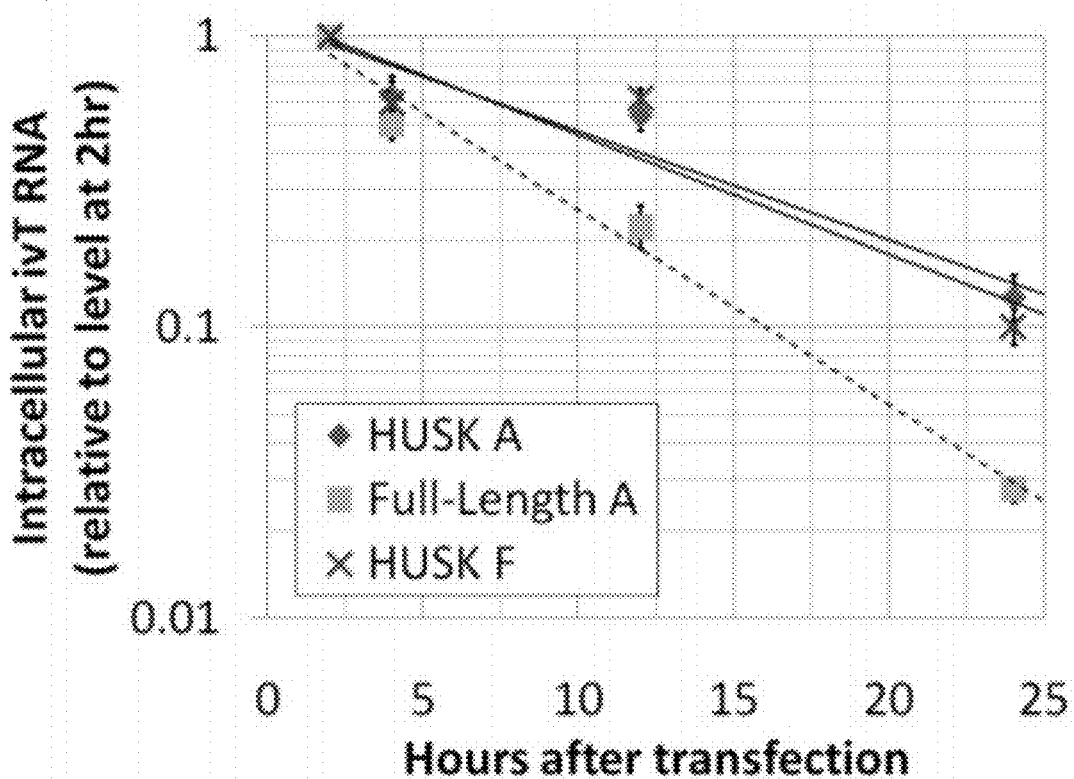

By "innate immune response" and "innate immune response" pathway is meant an immune response mounted by a cell to transfection with an exogenous nucleic acid including DNA, RNA, or DNA/RNA chimeras in any form including as a plasmid, a vector, an ivT-RNA transcript, or to endogenous nucleic acids removed from the cell and retransfected into the same cell or a different cell, and including nucleic acids containing one or more modifications such as a 2'-O-methylated nucleotide.

By "proteins in the innate immune response pathway" or "immune suppression proteins" is meant the proteins TP53, TLR3, TLR7, RARRES3, IFNA1, IFNA2, IFNA4, IFNA5, IFNA6, IFNA7, IFNA8, IFNA10, IFNA13, IFNA14, IFNA16, IFNA17, IFNA21, IFNK, IFNB1, IL6, TICAM1, TICAM2, MAVS, STAT1, STAT2, EIF2AK2, IRF3, TBK1, CDKN1A, CDKN2A, RNASEL, IFNAR1, IFNAR2, OAS1, OAS2, OAS3, OASL, RB1, ISG15, ISG20, IFIT1, IFIT2, IFIT3, and IFIT5, or a biologically-active fragment, analog or variant thereof. Immune suppression proteins further include any protein or peptide that increases the expression of type I interferons or the expression of which is increased by exposing the cell to type I interferons. The full names of the proteins are: TP53=tumor protein p53; TLR3=toll-like receptor 3; TLR7=toll-like receptor 7; RARRES3=retinoic acid receptor responder (tazarotene induced) 3; IFNA1=interferon, alpha 1; IFNA2=interferon, alpha 2; IFNA4=interferon, alpha 4; IFNA5=interferon, alpha 5; IFNA6=interferon, alpha 6; IFNA7=interferon, alpha 7; IFNA8=interferon, alpha 8; IFNA10=interferon, alpha 10; IFNA13=interferon, alpha 13; IFNA14=interferon, alpha 14; IFNA16=interferon, alpha 16; IFNA17=interferon, alpha 17; IFNA21=interferon, alpha 21; IFNK=interferon, kappa; IFNB1=interferon, beta 1, fibroblast; IL6=interleukin 6 (interferon, beta 2); TICAM1 toll-like receptor adaptor molecule 1; TICAM2=toll-like receptor adaptor molecule 2; MAVS=mitochondrial antiviral signaling protein; STAT1=signal transducer and activator of transcription 1, 91 kDa; STAT2=signal transducer and activator of transcription 2, 113 kDa; EIF2AK2=eukaryotic translation initiation factor 2-alpha kinase 2; IRF3=interferon regulatory factor 3; TBK1=TANK-binding kinase 1; CDKN1A=cyclin-dependent kinase inhibitor 1A (p21, Cip1); CDKN2A=cyclin-dependent kinase inhibitor 2A (melanoma, p16, inhibits CDK4); RNASEL=ribonuclease L (2',5'-oligoisoadenylate synthetase-dependent); IFNAR1=interferon (alpha, beta and omega) receptor 1; IFNAR2=interferon (alpha, beta and omega) receptor 2; OAS1=2',5'-oligoadenylate synthetase 1, 40/46 kDa; OAS2=2',5'-oligoadenylate synthetase 2, 69/71 kDa; OAS3=2',5'-oligoadenylate synthetase 3, 100 kDa; OASL=2',5'-oligoadenylate synthetase-like; RB1=retinoblastoma 1; ISG15=ISG15 ubiquitin-like modifier; ISG20=interferon stimulated exonuclease gene 20 kDa; IFIT1=interferon-induced protein with tetratricopeptide repeats 1; IFIT2=interferon-induced protein with tetratricopeptide repeats 2; IFIT3=interferon-induced protein with tetratricopeptide repeats 3; and IFIT5=interferon-induced protein with tetratricopeptide repeats 5.

By "Kozak" is meant the sequence surrounding the start codon of an mRNA molecule that plays a role in determining the efficiency with which the mRNA is translated into protein.[46]

By "strong Kozak" is meant (1) the Kozak consensus sequence RCC(AUG)G known to yield maximum translation efficiency with the start codon in parentheses, and the "R" at position-3 representing a purine (A or G) and (2) also other strong Kozak sequences having the general formula RXY(AUG), where R is a purine (A or G), Y is either C or G, and X is any base. Of the non-coding nucleotides, the bases at positions -3 and -1 are the most critical for a strong consensus and efficient translation.

By "in vitro-transcribed RNA" or "ivT-RNA" encoding a protein of interest is meant any ivT-RNA construct or transcript that can be introduced into a cell and translated by the into a protein, either in vitro or in vivo. Construct and transcript are used interchangeably herein when referring to HUSK ivT-RNA.

By "HUSK ivT RNA" is meant an ivT-RNA transcript or construct that has been customized to achieve a high level of expression of an encoded protein therein. The new ivT-RNA transcripts get their name from transcripts used herein that have at their 5' end an HBB UTR, and are thus HBB-UTR-Stabilized, and include the Kozak consensus sequence (HUSK). Example embodiments of a HUSK ivT RNA include the following in schematic representation, wherein "CDS" means protein coding sequence, "stable UTR" means untranslated region from a highly stable mRNA molecule, preferably an alpha or beta globin, and 5' UTR means a first UTR on the 5' side of the strong Kozak sequence and 3' UTR means a second UTR on the 3' side of the CDS, "IRES" means internal ribosome entry site, "m7G" means 7 guanosine, "poly(A) means poly adenenosine tail at the 3' end of the molecule;

5' stable 5'UTR—strong Kozak—CDS 3'
5' stable 5'UTR with IRES—strong Kozak—CDS 3'
5' stable 5' UTR—strong Kozak—(CDS)—stable 3'UTR 3'
5' stable 5' UTR—strong Kozak—(CDS)—stable 3'UTR 3'

The embodiments further include any of the above further including a poly(A) tail at the 3' end of the transcript, and any of the above further including a m7G cap at the 5' end of the transcript, and any of the above with both an m7G cap at the 5' end and a poly(A) tail at the 3' end of the transcript.

Where the transcript has an m7G cap, the second nucleotide thereafter can optionally have a 2'-O-methyl modification.

By "stable UTR" is meant a UTR from a highly stable mRNA, preferably alpha or beta globin UTR. In general the UTR is from a heterologous source relative to the protein encoded by the ivT-RNA. However, the stable 5' UTR could be naturally-occurring if the encoded protein in the HUSK ivT-RNA is beta or alpha globin, for example.

By "HUSK ivT-RNA template" is meant a DNA molecule that is customized to have a strong transcription promoter operably linked to a construct that produces an ivT-RNA, and which construct has a first restriction site (such as that for the enzyme NheI) that joins the stable 5' UTR to the strong Kozak sequence, and a second restriction site (such as that for the enzyme Ang1) that joins the CDS to the stable 3' UTR as necessary depending on the particular embodiment. The HUSK ivT-RNAs transcripts are transcribed from a HUSK ivT-RNA template.

By "strong promoter" is meant a promoter that exhibits at least about 80%-90% or more of the activity the T7, T3, SP6 promoters on the same DNA template in the same reaction conditions.

SUMMARY OF THE INVENTION

Certain embodiments of the invention are directed to a method for suppressing the innate immune response of a cell to transfection with a nucleic acid by introducing to the cell an effective amount of an agent that reduces the expression of one or more proteins in the innate immune response pathway as defined herein, or to biologically-active fragments or analogs thereof. In an embodiment the agent is siRNA, one or more antisense oligonucleotides or any combination thereof, and the cell is an animal cell, preferably a human cell. In certain embodiments the agent is an antibody that selectively binds to a protein in the innate immune response pathway or biologically-active fragment thereof, thereby reducing its biological activity. Introducing the nucleic acid can be accomplished using any method known in the art including electroporation, lipid-mediated transfection, ballistic transfection, magnetofection, peptide-mediated transfection, microinjection, or a combination thereof.

Other embodiments are directed to a method for transfecting a cell with a nucleic acid molecule, by a.) suppressing the innate immune response of the cell, and b.) introducing the nucleic acid into the cell. In a preferred embodiment the nucleic acid molecule encodes a protein or biological fragment thereof, or an RNA molecule that includes a single-stranded DNA or RNA molecule (preferably ivT-RNA), and a double stranded DNA or RNA molecule or a single or double stranded DNA/RNA chimera. Steps a.) and b.) can be simultaneous or consecutive, and in a preferred embodiment steps a.) and b.) are repeated two or more times. In a preferred embodiment the cell is an animal cell, preferably a human. Transfection can be accomplished in vitro or in vivo. In another preferred embodiment transfection with the nucleic acid causes expression of one or more proteins which, in turn, cause a desired phenotypic change in the cell including differentiation, transdifferentiation, or dedifferentiation of stem cells or differentiated cells.

Other embodiments are directed to a composition that includes a plurality of different siRNAs, one or more antisense oligonucleotides, or combinations thereof that specifically hybridize to mRNA or DNA molecules encoding two or more proteins in the innate immune response pathway or biologically-active fragments or analogs thereof, thereby reducing expression of the two or more proteins. In a preferred composition the mixture of siRNAs specifically hybridize to mRNA or DNA molecules encoding TP53, STAT2, and EIF2AK2, or a mixture of siRNAs that specifically hybridize to mRNA or DNA molecules encoding TP53, STAT2, EIF2AK2, and IFNB1. Other embodiments are directed to a cell produced by the immunosuppression and transfection methods.

Certain other embodiments are directed to various highly stable and efficiently translated in vitro-transcribed RNA transcripts encoding a protein of interest, which constructs have in operable combination, (i) a stable 5' UTR, and (ii) a strong Kozak sequence linked to a protein coding sequence (CDS). In some embodiments the transcript further includes (iii) a stable 3' UTR. Preferred UTRs are beta and alpha globin UTRs. The transcripts can further include one or more of the following elements: a poly(A) tail at the 3' end of the transcript, a 7-methylguanosine cap at the 5' end of the transcript, and an internal ribosome entry site.

Other embodiments are directed to DNA templates for making ivT-RNA and to kits that enable the user to insert a CDS of interest into a template that has a strong transcription promoter operably linked to a construct that produces an in vitro-transcribed RNA, the first strand of which comprises in operable combination (i) a stable 5' UTR, and (ii) a first restriction site capable of joining the 5' UTR to a Kozak consensus sequence.

DETAILED DESCRIPTION

The present invention relates in part to methods for suppressing the innate immune response of a cell to transfection with an exogenous nucleic acid, to methods for increasing expression of a protein encoded by an exogenous nucleic acid by repeated delivery of the exogenous nucleic acid to a cell, and to methods of changing the phenotype of a cell by differentiating, transdifferentiating or dedifferentiating cells by repeatedly delivering one or more nucleic acids that encode defined proteins. In a preferred embodiment, the nucleic acid is in vitro-transcribed RNA ("ivT-RNA") and a high and sustained level of expression of a protein encoded by an ivT-RNA transcript ("the encoded protein") is achieved and maintained over multiple cell generations by repeatedly transfecting the cell with ivT-RNA as needed to sustain the desired level of encoded protein expression.

In a preferred embodiment, ivT-RNA-encoded protein expression is further increased by suppressing the cell's innate immune response, preferably before transfection, preferably by introducing to the cell an amount of siRNA and/or antisense oligonucleotides that are specifically hybridizable to an mRNA or DNA molecule encoding one or more proteins in the innate immune response pathway as defined herein, thereby reducing expression of the targeted protein. Antibodies or small molecules that reduce the biological activity of one or more proteins in the innate immune response pathway can also be used, either alone or in combination with the siRNA or antisense oligonucleotides. In a preferred embodiment the innate immune response is suppressed about 24 to 48 hours before the first ivT-RNA transfection, and immune response suppression is repeated as needed, preferably at least about every 48 hours, to sustain the high level of encoded protein expression through subsequent rounds of ivT-RNA transfection.

Other embodiments are directed to stable and efficiently translated ivT-RNA transcripts or constructs hereafter referred to as "HUSK ivT-RNA transcripts" that can be customized to encode any protein of interest, and to DNA templates used for making them. Various embodiments of the HUSK ivT-RNA transcripts are described in the definitions and in more detail below. In an example of a preferred HUSK ivT-RNA, the naturally-occurring 5' UTR of the encoded protein is replaced by a 5' UTR derived from a highly stable mRNA (hereafter "stable 5' UTR") such as that encoding beta globin ("HBB") or alpha globin, and the naturally-occurring Kozak sequence is replaced with a "strong Kozak" consensus sequence, preferably (RCC (AUG)). The ivT-RNA transcripts get their name from transcripts used herein that have at their 5' end an HBB UTR, and are thus HBB-UTR-Stabilized, and include the strong Kozak consensus sequence (HUSK).

In another preferred embodiment the HUSK ivT-RNA transcript also has a second stable UTR on the 3' side (the stable 3' UTR) of the protein coding sequence (hereafter "CDS"), a poly(A) tail on the 3' end to facilitate translation, and either a 7-methylguanosine cap at the 5' end or an internal ribosome entry site (hereafter "IRES") located in the stable 5' UTR. The IRES facilitates ribosome attachment to the ivT-RNA to increase translation efficiency. Yet other embodiments are directed to kits that let the user customize the templates and the HUSK ivT-RNA transcribed from them by inserting any nucleic acid.

Other embodiments are directed to methods for changing the phenotype of a cell by extended transient transfection by repeated delivery of HUSK ivT-RNA encoding one or more proteins that are known to affect or control cellular phenotype. For example, causing a stem cell to differentiate into a cell with a desired phenotype or causing a differentiated cell to transdifferentiate into a cell with a desired phenotype, or to dedifferentiate into a stem cell or other precursor cell. Other embodiments are directed to cells transfected with HUSK ivT-RNAs encoding defined proteins and to various compositions of siRNAs and antisense oligonucleotides.

HUSK ivT-RNA Design

The present invention provides improved ivT-RNAs referred to as HUSK ivT-RNAs that are efficiently translated to achieve a consistently high and sustained level of expression of an encoded protein for extended periods of time. IvT-RNA transfection is used widely to study a variety of cellular processes, particularly where the transient over expression of one or more proteins or particular genes is desired.[32-34] High-efficiency, high-viability transfection of human embryonic stem cells (hES) with ivT-RNA has recently been demonstrated[35]. Techniques for the in vitro synthesis of large quantities of capped, polyadenylated ivT-RNAs have been available for some time,[36-39] as have a variety of delivery techniques including electroporation and lipid-mediated transfection.[40-45]

Although the intracellular lifetime of most mRNA molecules is only a few hours, the degradation rate of an mRNA molecule is strongly affected by sequence elements present in its untranslated regions (UTRs). Replacing the UTRs of an ivT-RNA transcript with those of a more stable mRNA molecule has been shown to increase the intracellular stability of the ivT-RNA transcript, thus increasing the amount of protein that can be translated.[42] The stability of an mRNA molecule is determined primarily by the sequences of its 5'- and 3'-UTRs, which regulate degradation by associating with specific factors.[47-49] Replacing either the 5'- or 3'-UTR of an unstable RNA molecule with a UTR from a more stable mRNA molecule has been shown to significantly increase its stability; replacing both UTRs further increases stability.

The sequence surrounding the start codon of an mRNA molecule (known as the "Kozak sequence") has also been shown to play a crucial role in determining the efficiency with which the mRNA is translated into protein.[46] The strongest Kozak consensus sequence yielding maximum translation efficiency is: RCC(AUG)G (hereafter "the Kozak consensus sequence"), with the start codon in parentheses, and the "R" at position-3 representing a purine (A or G). More generally, the sequence RXY(AUG), where R is a purine (A or G), Y is either C or G, and X is any base is considered an efficient, hence a "strong Kozak sequence" for the purpose of the present invention. Of the non-coding nucleotides, the bases at positions −3 and −1 are the most critical for a strong consensus and efficient translation. Without being bound by theory, the dependence of translation efficiency on the sequence surrounding the start codon has been explained by a model of translation in which certain portions of the mRNA sequence that are complementary to the ribosome can cause the translation complex to pause near the start codon, increasing the probability of translation initiation.

Certain embodiments of the invention are directed to improved ivT-RNA transcripts that are stable and efficiently translated (hereafter referred to as "HUSK ivT-RNA transcripts or constructs") that can be customized to encode any protein of interest, and to DNA templates used for making them. Various embodiments of the HUSK ivT-RNA transcripts are described in the definitions. In the simplest embodiments of a HUSK ivT-RNA the naturally-occurring Kozak sequence of the encoded protein is replaced with a strong Kozak sequence, preferably the Kozak consensus sequence (RCC(AUG) and the naturally occurring 5' UTR is replaced with a "stable 5'UTR," which optionally includes an internal ribosome entry site ("IRES"). In a preferred embodiment both the naturally-occurring 5' UTR and 3' UTR sequences of the encoded protein are replaced with a stable UTR, preferably from beta globin (HBB) and/or alpha globin. In another preferred embodiment the HUSK ivT-RNA transcript also has a poly(A) tail on the 3' end to facilitate translation. One example embodiment is set forth below.

Stable 5' UTR with or without IRES—Strong Kozak—CDS—Stable 3' UTR—Poly(A) 3'

In the embodiments having stable UTRs at both the 5' and 3' positions, each UTR can be the same or different, but each is derived from a stable mRNA and as such is different than the corresponding naturally-occurring UTRs of the endogenous mRNA that encodes the encoded protein. The β-globin gene (HBB) was used in the experiments described below because it encodes one of the most stable mRNA molecules known.[49] The HBB UTRs are short (5'-UTR=50 nt, 3'-UTR=132 nt) and therefore contribute only a small amount of mass to a protein-encoding transcript of average length, giving the complete transcript a high copy-to-mass ratio. In the exemplified embodiments, the HUSK ivT-RNA transcripts included the HBB UTRs at both the 5'- and 3'-positions to maximize the intracellular stability. (See references 42, 47-49). In addition to beta-globin, alpha-globin mRNA is known to have a high intracellular stability as a result of specific elements in its UTRs, and can be used to make HUSK ivT-RNAs. (see reference 47, and also Russell, et al. "Sequence Divergence in the 3' Untranslated Regions of Human ζ- and α-Globin mRNAs Mediates a Difference in Their Stabilities and Contributes to Efficient α-to-ζ Gene Developmental Switching." Mol Cell Biol. 18(4) 2173-2183. 1998.) The UTRs from other structural proteins such as the actins, collagens and crystallines have mRNAs with long intracellular half-lives (see the references cited in 47) and therefore can also be used.

Other features that increase translation can also be included. For example, in one embodiment the construct has an internal ribosome entry site (IRES) that facilitates attachment of ribosomes to the transcript to increase translation. The IRES is an element in the 5'UTR, and so it is between the 5'-end of the ivT-RNA transcript and the strong Kozak sequence. Another optional feature of the HUSK ivT-RNA is a 7-methylguanosine (m7G) cap at the 5' end. If the transcript has an IRES, it does not need to have an m7G cap, although both elements could be used. In another embodiment the HUSK ivT-RNA has a second nucleotide that contains a 2'-O-methyl modification immediately following the 5' m7G cap. This modification is a component of many mRNAs in higher eukaryotic organisms, and is known to increase the efficiency with which ivT-RNA transcripts are translated into protein.

Certain embodiments are directed to the seven different HUSK ivT-RNAs described herein, each encoding a protein that was selected based on its known gene targets, its participation in cellular differentiation, maintenance of cell-type specificity and gene-expression programs, and the length of its coding sequences. The seven ivT-RNA-encoded proteins include five transcription factors and one mRNA-binding protein and one master gene. Transcripts A-G refer to the HUSK ivT-RNA constructs each encoding the following respective human proteins or biologically-active fragments, analogs or variants thereof:

Transcript A: OCT4 (mRNA SEQ ID NO: 1),
Transcript B: SOX2 (mRNA SEQ ID NO: 2),
Transcript C: KLF4 (mRNA SEQ ID NO: 3),
Transcript D: MYC (mRNA SEQ ID NO: 4),
Transcript E: NANOG (mRNA SEQ ID NO: 5),
Transcript F: LIN28 (mRNA SEQ ID NO: 6), and
Transcript G: MYOD1 (mRNA SEQ ID NO: 7).

Other proteins that are desirable for encoding in ivT-RNA include the following that have a role in phenotypic determination as is discussed below: Ascl1 (mRNA SEQ ID NO: 8), PU.1 (mRNA SEQ ID NO: 9), C/EBPα (mRNA SEQ ID NO: 10), C/EBPβ (mRNA SEQ ID NO: 11), Ngn3 (mRNA SEQ ID NO: 12), Pdx1 (mRNA SEQ ID NO: 13), Mafa (mRNA SEQ ID NO: 14), and Esrrb (mRNA SEQ ID NO: 15), or a biologically-active fragment or variant thereof.

The full protein names are: OCT4=POU class 5 homeobox 1; SOX2=SRY (sex determining region Y)-box 2; KLF4=Kruppel-like factor 4 (gut); MYC=v-myc myelocytomatosis viral oncogene homolog (avian); NANOG=Nanog homeobox; LIN28=lin-28 homolog (*C. elegans*); MYOD1=myogenic differentiation 1; ASCL1=achaete-scute complex homolog 1 (*Drosophila*); SPI1=spleen focus forming virus (SFFV) proviral integration oncogene spi1; CEBPA=CCAAT/enhancer binding protein (C/EBP), alpha; CEBPB=CCAAT/enhancer binding protein (C/EBP), beta; NEUROG3=neurogenin 3; PDX1=pancreatic and duodenal homeobox 1; MAFA=v-maf musculoaponeurotic fibrosarcoma oncogene homolog A (avian); and ESRRB=estrogen-related receptor beta.

Table 1 provides the names of the genes encoding proteins that were either tested, for which a specific example is included, or that are closely related members of the same family of one or more of those genes. It is known that closely related gene-family members referred to herein as "analogs," often have the same biological activity and so they can be used interchangeably. The gene symbol of each protein is provided in the first column; the list includes certain analogs and variants with their mRNA Accession Numbers.

Certain embodiments are directed to HUSK ivT-RNAs that encode any of the proteins in Table 1 or biologically-active fragments, analogs or variants thereof

TABLE 1

| OFFICIAL HUMAN GENE SYMBOL | NCBI REFSEQ MRNA ACCESSION NUMBERS |
|---|---|
| POU2F1 | NM_002697 |
| POU2F2 | NM_002698 |
| POU2F3 | NM_014352 |
| POU3F1 | NM_002699 |
| POU3F2 | NM_005604 |
| POU3F3 | NM_006236 |
| POU3F4 | NM_000307 |
| POU5F1 (encodes OCT4) | NM_002701, NM_203289 |
| POU5F2 | NM_153216 |
| POU6F1 | NM_002702, NR_026893 |
| POU6F2 | NM_007252 |
| SOX1 | NM_005986 |
| SOX2 | NM_003106 |
| SOX3 | NM_005634 |
| SOX4 | NM_003107 |
| SOX5 | NM_006940, NM_152989, NM_178010 |
| SOX6 | NM_017508, NM_033326, NM_001145811, NM_001145819 |
| SOX7 | NM_031439 |
| SOX8 | NM_014587 |
| SOX9 | NM_000346 |
| SOX10 | NM_006941 |
| SOX11 | NM_003108 |
| SOX12 | NM_006943 |
| SOX13 | NM_005686 |
| SOX14 | NM_004189 |
| SOX15 | NM_006942 |
| SOX17 | NM_022454 |
| SOX18 | NM_018419 |
| SOX21 | NM_007084 |
| SOX30 | NM_178424, NM_007017 |
| KLF1 | NM_006563 |
| KLF2 | NM_016270 |
| KLF3 | NM_016531 |
| KLF4 | NM_004235 |
| KLF5 | NM_001730 |
| KLF6 | NM_001300 |
| KLF7 | NM_003709 |
| KLF8 | NM_007250, NM_001159296 |
| KLF9 | NM_001206 |
| KLF10 | NM_005655, NM_001032282 |
| KLF11 | NM_003597 |
| KLF12 | NM_007249 |
| KLF13 | NM_015995 |
| KLF14 | NM_138693 |
| KLF15 | NM_014079 |
| KLF16 | NM_031918 |
| KLF17 | NM_173484 |
| POU5F1P1 | NR_002304 |
| MYC | NM_002467 |
| MYCL1 | NM_005376, NM_001033081, NM_001033082 |
| MYCN | NM_005378 |
| NANOG | NM_024865 |
| LIN28 | NM_024674 |
| THAP11 | NM_020457 |
| TERT | NM_198253, NM_198255 |
| MYOD1 | NM_002478 |
| ASCL1 | NM_004316 |
| SPI1 | NM_003120, NM_001080547 |
| CEBPA | NM_004364 |
| CEBPB | NM_005194 |
| NEUROG3 | NM_020999 |
| PDX1 | NM_000209 |
| MAFA | NM_201589 |
| ESRRB | NM_004452.2 |

MYOD1 is a master gene; transducing MYOD1 in fibroblasts (non-muscle cells) has been shown to be sufficient to cause them to transdifferentiate into myoblasts (muscle cells). A master gene is a gene at the highest level of the regulatory network that controls the gene-expression program of a cell. Master genes are usually transcription factors that directly control the expression of multiple genes, many of which in turn control the expression of more genes to establish the cell's gene-expression program. Inducing the expression of one or more master genes has been shown in several cases to induce a cell to differentiate, transdifferentiate, or dedifferentiate to the cell type that normally expresses the master gene. Seven double-stranded DNA templates were also designed that were transcribed to make the respective HUSK ivT-RNA transcripts. The seven ivT-RNA transcripts used in the experiments described herein had the following structure:

5' m7G Cap 2'-O-methylated Second Nucleotide—Stable 5'UTR with IRES/Strong Kozak/Coded Protein Sequence (CDS)/Stable 3'UTR/polyA Tail 3' ivT-template Assembly and In Vitro Transcription

Details for designing and making the HUSK templates are set forth in Example 2. The HUSK templates used in the experiments described herein are DNA molecules that include the strong T7 promoter at the 5' end, operably linked to a construct that produces an in vitro-transcribed RNA, which has in the simplest embodiment (i) a stable 5' UTR, and (ii) the strong Kozak consensus sequence RCC(AUG)G linked to a protein coding sequence (CDS). The templates further included a first restriction site which joins the 5' UTR to the Kozak consensus sequence (as shown below, a NheI site), and a second restriction site which joins the CDS to the 3' UTR (as shown below, an AgeI site).

Other strong promoters include T3 and SP6. The exemplified template has a stable HBB UTRs. Any restriction site can be used that enables the insertion of the strong Kozak sequence, the CDS and the stable 3' UTR at the appropriate sites. An embodiment is directed to the template which is set forth below (the drawing below discloses SEQ ID NOS: 19-21, respectively, in order of appearance).

CDS has to be connected with a restriction site, and there cannot be any space between the Kozak and the CDS, the restriction site has to be on the 5'-end of the Kozak, so the Kozak has to be connected to the user's CDS.

In other embodiments the kit may include one or more of the following: a polymerase that recognizes and binds to the promoter, a buffer suitable for conducting an in vitro-transcription reaction, a mixture of nucleotide triphosphates (NTPs), the restriction enzymes that recognize the first and the second restriction sites, a DNAse enzyme solution for degrading the used template once the in vitro-transcription reaction is complete, a capping enzyme for producing the 5' m7G cap, a 2-O-methyltransferase enzyme for adding a methyl group to the second nucleotide, a solution of GTP, a solution of S-adenosyl methionine (SAM), a poly(A) polymerase enzyme (for example E. coli poly(A) polymerase), a solution of ATP, and a buffer for the poly(A)-tailing reaction. The kit may further include a DNA template to be used as a positive control.

Transcript Synthesis

Messenger RNA (mRNA) used to make the various HUSK ivT-RNA templates was obtained from H9 human embryonic stem cells as is described in Example 2, and was amplified from reverse-transcribed poly(A)+ mRNA: Transcript A=OCT4, Transcript B=SOX2, Transcript C=KLF4, Transcript D=MYC, Transcript E=NANOG, Transcript F=LIN28, and Transcript G=MYOD1. A high-fidelity polymerase was used in all stages of the dsDNA template synthesis to minimize sequence errors. Denaturing formaldehyde-agarose gel electrophoresis was performed to confirm that the transcripts had the expected size before polyadenylation, that they were undegraded, and that the polyadenylation reaction added a poly(A) tail of sufficient length to promote efficient translation. Although full-length transcripts were produced from each template, completed reactions also contained large amounts of low-molecular-weight products, identified as a combination of prematurely terminated and degraded transcripts. Reducing the temperature of the in vitro-transcription reaction (i.e. the transcription of the template into ivT-RNA) to about 4-37° C.,

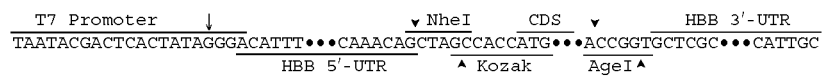

```
T7 Promoter          ↓           ▼ NheI    CDS   ▼      HBB 3'-UTR
TAATACGACTCACTATAGGGACATTT•••CAAACAGCTAGCCACCATG•••ACCGGTGCTCGC•••CATTGC
                     HBB 5'-UTR         ▲ Kozak     AgeI▲
```

Certain embodiments are directed to the seven templates described herein (and variants with different promoters, stable UTRs, restriction sites and strong Kozak sequences known in the art). In preferred embodiments the templates encode the proteins Oct4, Sox2, Klf4, Myc, Nanog, Lin28, and MyoD, or biologically-active fragment, analog or variant thereof.

Other embodiments are directed to kits that enable a user to insert any nucleic acid, preferably an mRNA encoding a protein of interest. Such kits for expressing a protein or peptide using in vitro-transcribed RNA include a DNA template having a strong transcription promoter operably linked to a construct that produces an in vitro-transcribed RNA, the first strand of which comprises in operable combination (i) a stable 5' UTR, and (ii) a first restriction site which joins the 5' UTR to a Kozak consensus sequence. The user designs a CDS with a strong Kozak and the appropriate complementary restriction sites to enable binding of the CDS to the template. The kit may further include primers to create the CDS from reverse transcribed RNA. Because the preferably 10° C. for about 20 hours dramatically increased the fraction of full-length transcripts produced. Temperatures between 4° C. and 15° C. are recommended, but may vary based on the experimental conditions. Capped, poly (A)+ transcripts were synthesized in T7 in vitro-transcription reactions from the seven linear dsDNA templates described above.

Delivery of In Vitro-transcribed RNA to Cells

MRC-5 human fetal-lung fibroblasts were chosen as the model for transfection with HUSK ivT-RNA for this study because they are easily cultured, they undergo several population doublings before the onset of senescence, and because as primary cells, they represent a more appropriate model for the development of cell-based therapies than would an immortalized cell line that can present a safety risk to patients due to the possibility of tumorigenesis. In addition, MRC-5 fibroblasts do not endogenously express the proteins encoded by Transcripts A-F, facilitating the analysis of protein translation from ivT-RNA.

Two nucleic-acid-delivery techniques are commonly used to transiently transfect cells: lipid-mediated transfection, and electroporation. Lipid-mediated transfection stimulates active uptake of nucleic acids by endocytosis, while electroporation delivers nucleic acids by transiently opening holes in the cell membrane while the cell is in a solution in which the nucleic acid is present at high concentration. This difference generally makes lipid-mediated transfection more suitable for delivering nucleic acids to cells under close-to-normal growth conditions (normal culture media, although often without serum, normal plating density, and attached to a culture dish if the cells are grown in adherent culture.)

Transfection techniques other than electroporation and lipid transfection can be used. These include: 1. Ballistic transfection (a.k.a. gene gun, a.k.a. biolistic transfection), 2. Magnetofection (see Scherer, et al. "Magnetofection: enhancing and targeting gene delivery by magnetic force in vitro and in vivo." Gene Therapy. Vol. 9. p. 102-109. 2002.), 3. Peptide-mediated transfection (either non-covalent peptide/RNA nanoparticle-based transfection such as the N-TER™ Transfection System from Sigma-Aldrich or by covalent attachment of the peptide to the RNA), and 4. Microinjection. Combinations of these techniques used in succession or simultaneously can also be used. Any method known in the art for introducing a nucleic acid to a cell may be used in the embodiments of the present invention.

To determine whether the HUSK ivT-RNA produced is readily translated into the encoded protein by primary cells, Transcripts A, B, and F were delivered to cultures of MRC-5 fibroblasts using a lipid-mediated transfection reagent (TransIT, Mirus Bio, see Methods), and the cells were stained 24 hours later using antibodies against the proteins encoded by each transcript. Many of the cells in cultures transfected with HUSK ivT-RNA stained brightly, and staining was correctly localized, while mock-transfected cells exhibited only a low level of background fluorescence. H9 hES cells that normally express the proteins encoded by Transcripts A-F exhibited a similar staining pattern and intensity, showing that the level of encoded protein expressed from HUSK ivT-RNA in MRC-5 fibroblasts 24 hours after transfection under these conditions is comparable to the level endogenously expressed by H9 cells. A western-blot analysis yielded similar results.

Although lipid-mediated transfection is a simple method for delivering RNA to cells, lipids are known to be inefficient when used to transfect cultures of primary cells, which generally exhibit low levels of endocytosis. In addition, the lipids have some degree of cytotoxicity as do the ancillary nucleic-acid-condensing compounds often used to increase lipid-mediated-transfection efficiency. While cells transfected using lipids may recover quickly, any cytotoxicity associated with lipid-mediated transfection reagents may be compounded in cells that are repeatedly transfected.

To attain the desired level of HUSK ivT-RNA-encoded protein expression that was achieved in the MRC-5 fibroblasts described above, transfection with a high concentration of lipid-RNA complexes was required. Increasing the amount of HUSK ivT-RNA delivered to the cells beyond this level resulted in decreased viability. Therefore electroporation of cells in suspension was tested. Electroporation does not require active uptake, but instead directly delivers the nucleic acids through the cell membrane. Although adherent cells can be electroporated because the cell membrane is permeabilized only transiently during electroporation, the concentration of the nucleic acid in the electroporation buffer must be high (a value of 100 µg/mL RNA is often used) to achieve an effective intracellular concentration. For this reason, electroporation is generally most suitable for transfecting cells in suspension, and allows the transfection of a large number of cells using a small amount of RNA because the cells can be suspended at high concentration during the electroporation procedure.

Electroporation parameters were optimized by transfecting MRC-5 fibroblasts with ivT-RNA, and measuring transfection efficiency by quantitative RT-PCR using primers designed to specifically detect the exogenous transcripts. Discharging a 150 uF capacitor charged to 145V into $2.5 \times 10^6$ cells suspended in 50µL of Opti-MEM (Invitrogen) in a standard electroporation cuvette with a 2 mm gap was sufficient to repeatedly deliver in excess of 10,000 copies of HUSK ivT-RNA per cell, as determined using the standard curve method, while maintaining high viability (70-90% of cells adherent 2 hours after plating). Further experiments revealed that the voltage required to efficiently transfect cells with HUSK ivT-RNA depends on the cell density during electroporation. While 145V was necessary to transfect cells at a density of $2.5 \times 10^6$ cells/50µL, as little as 110V was used to transfect cells at a density of $1 \times 10^6$ cells/50 µL with the same efficiency (same number of copies per cell). Routine experimentation will determine the optimum conditions for each particular transfection.

HUSK ivT RNA has a High Intracellular Stability and Protein Translation from HUSK ivT-RNA is Highly Efficient To compare the stability and translation efficiency of HUSK ivT-RNA to ivT-RNA encoding unmodified mRNA, a full-length Transcript A encoding OCT4 was synthesized using a template containing the complete sequence of the endogenous mRNA, which includes the naturally-occurring endogenous UTRs and the unmodified Kozak sequence associated with endogenous OCT4 mRNA. By contrast the HUSK transcripts had the HBB UTRs and the strong Kozak consensus sequence. RNAse A was added to the culture medium at a concentration of 100 µg/mL to eliminate extracellular HUSK ivT-RNA before making the measurement. The concentration of each of the HUSK transcripts reached 25% of its level at 2 hours approximately 17-18 hours after transfection, while the concentration of the full-length transcript reached 25% of its level at 2 hours approximately 10 hours after transfection, indicating that the intracellular stability of the HUSK transcript is significantly higher than that of the corresponding full-length transcript, and that the stabilities of the two HUSK transcripts A/OCT4 and F/LIN28 are comparable.

Figure 2B:
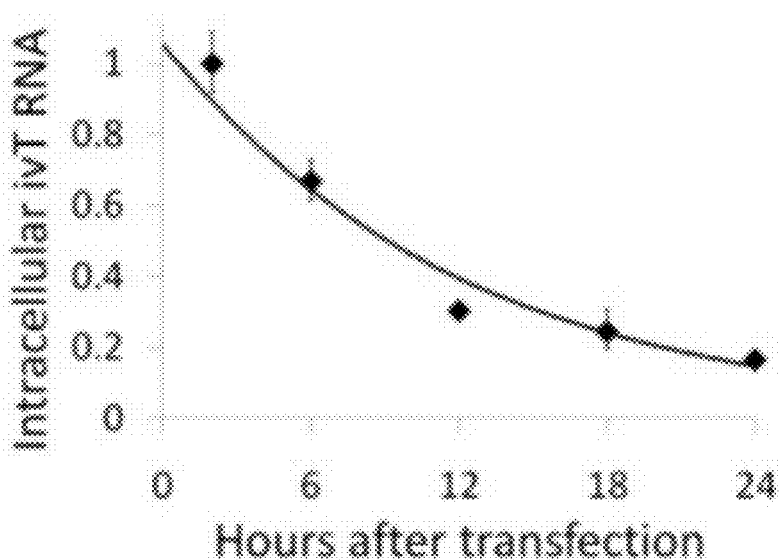

FIG. 2B presents a more thorough measurement of HUSK ivT RNA intracellular stability. Briefly, MRC-5 fibroblasts pre-transfected with an siRNA cocktail targeting IFNB1, EIF2AK2, STAT2, and TLR3 (see text below and methods) were co-transfected with 0.5 µg HUSK ivT RNA encoding LIN28 and additional siRNA at time 0. After the cells had attached, 200 µg/mL RNAse A was added to the culture medium to degrade extracellular RNA. Cells were lysed at the indicated times, and the amount of LIN28-encoding HUSK ivT RNA was measured by RT-PCR using primers specific to the exogenous transcript. An exponential regression (black line, $R^2=0.96$) is shown. GAPDH was used as an endogenous control. Error bars show the standard deviation of replicate samples.

To compare the translation efficiency of HUSK ivT-RNA to that of the corresponding full-length transcript without HBB UTRs or a modified Kozak consensus sequence, MRC-5 fibroblasts were transfected with either capped, poly(A)-tailed HUSK Transcript A/OCT4 or full-length endogenous Transcript A/OCT4, encoded protein was extracted after 12 hours and was analyzed by western blot. The results showed that 12 hours after electroporation, cells transfected with HUSK Transcript A contained approximately twice as much of the encoded protein as the cells transfected with the full-length transcript, indicating that transfecting cells with ivT-RNA based on the HUSK design results in the generation of significantly more encoded protein per transcript than transfection with the full-length endogenous unmodified transcript.

Figure 3A:
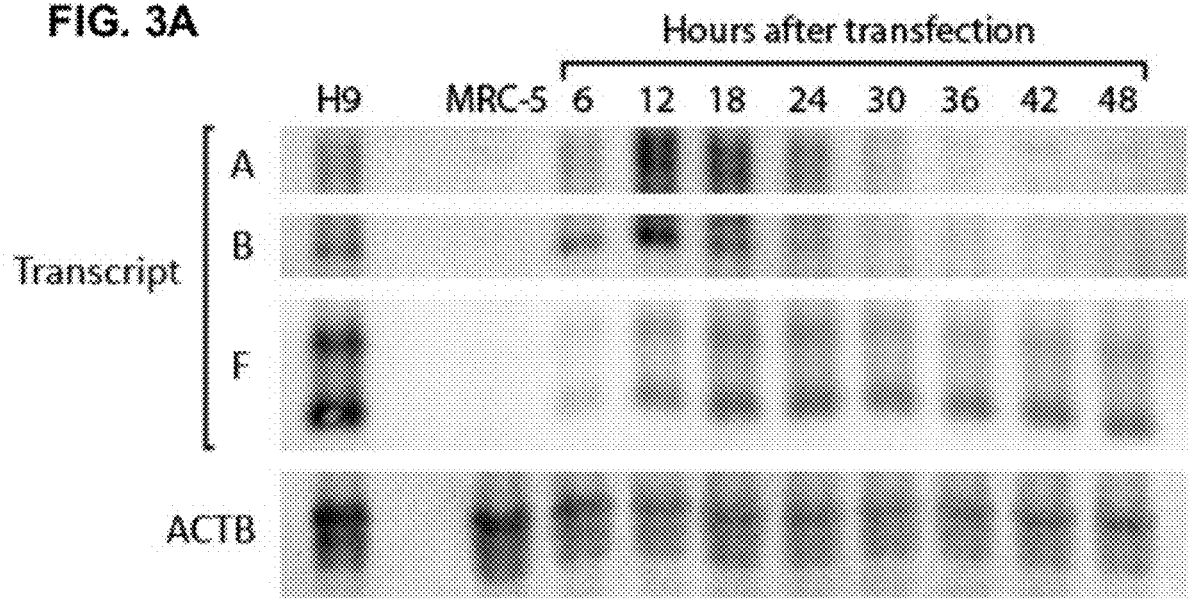
Figure 3B:
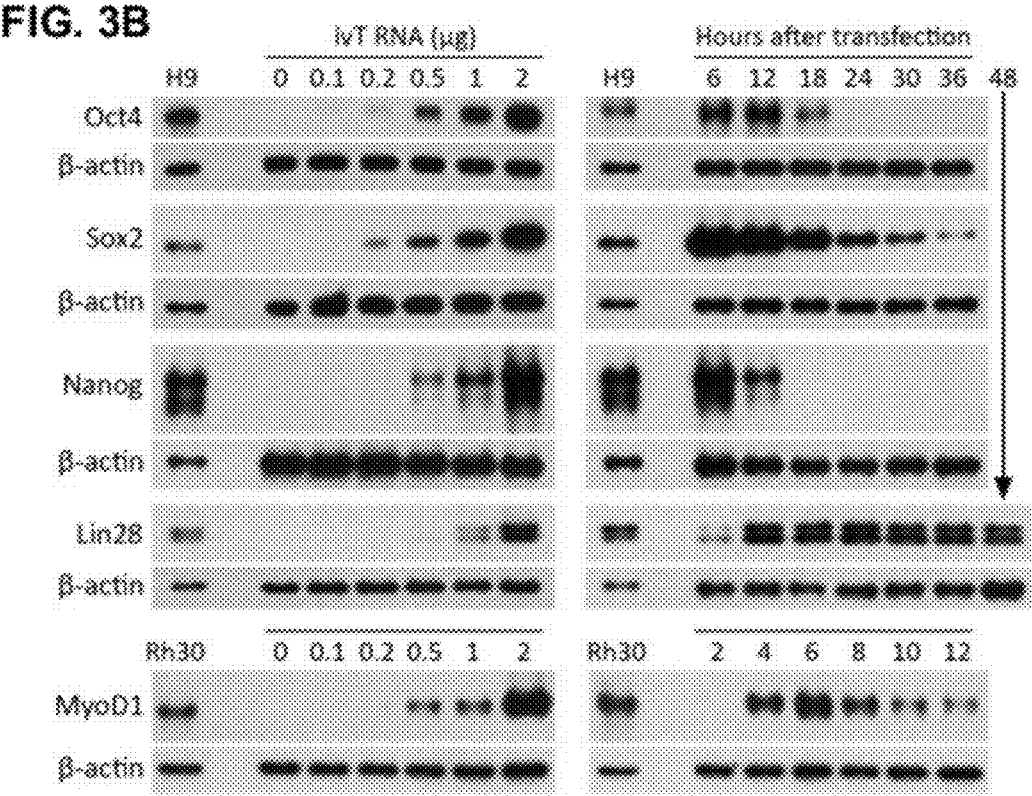

To understand how the concentration of encoded protein changes over time in cells transfected only one time with ivT-RNA, cells were transfected with HUSK Transcript A/OCT4, Transcript B/SOX2 or Transcript F/LIN28. Protein was extracted every 6 hours for 48 hours and was analyzed by western blot. The levels of the encoded protein in cells transfected with either HUSK Transcript A or B increased rapidly, peaked approximately 12 hours after transfection, and then decreased rapidly to levels that were barely detectable after 30 hours. FIG. 3A. By contrast, the level of the protein encoded by HUSK Transcript F increased rapidly, reaching its maximum value approximately 18-24 hours after transfection, and then remained fairly constant through 48 hours, showing that the protein encoded by HUSK Transcript F/LIN28 was significantly more stable than proteins encoded by HUSK Transcripts A/OCT4 and B/SOX2. Further analysis revealed that the protein encoded by HUSK Transcript F/LIN28 had an intracellular half-life of approximately 3 days when transfected under these conditions (not shown.) FIG. 3B provides an example of a more detailed protein expression analysis and includes data showing the dose-response of protein expression after transfection with HUSK ivT-RNA of the invention. Briefly, MRC-5 fibroblasts were transfected with the indicated HUSK ivT RNA, and whole-cell lysates were prepared at the indicated times. Alternatively, MRC-5 fibroblasts were transfected with the indicated amount of HUSK ivT RNA, and whole-cell lysates were prepared at the time of peak protein expression. The encoded proteins were then detected by western blot.

Suppressing the Innate-immune Response Rescues Cells from ivT-RNA Transfection

Figure 4A:
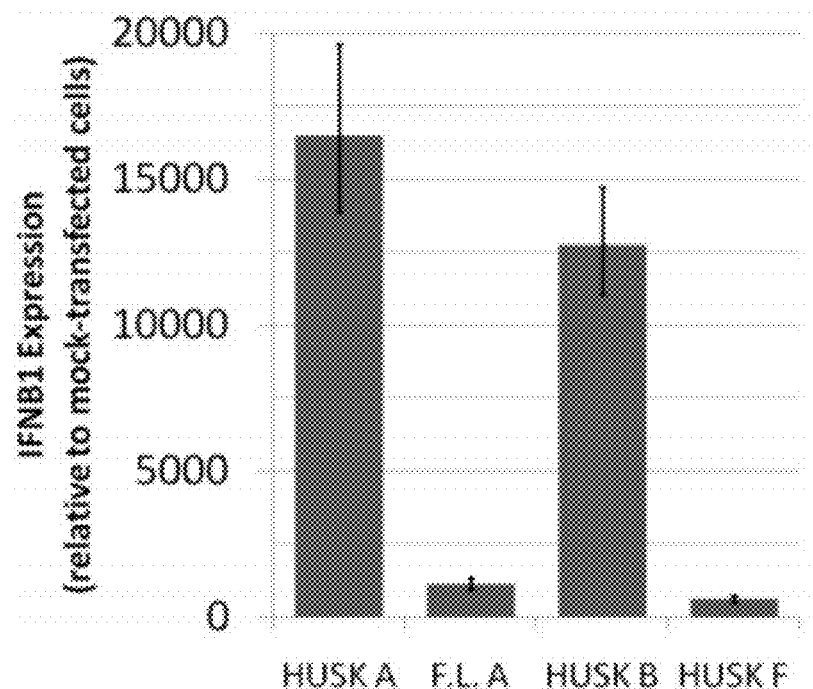
Figure 4B:
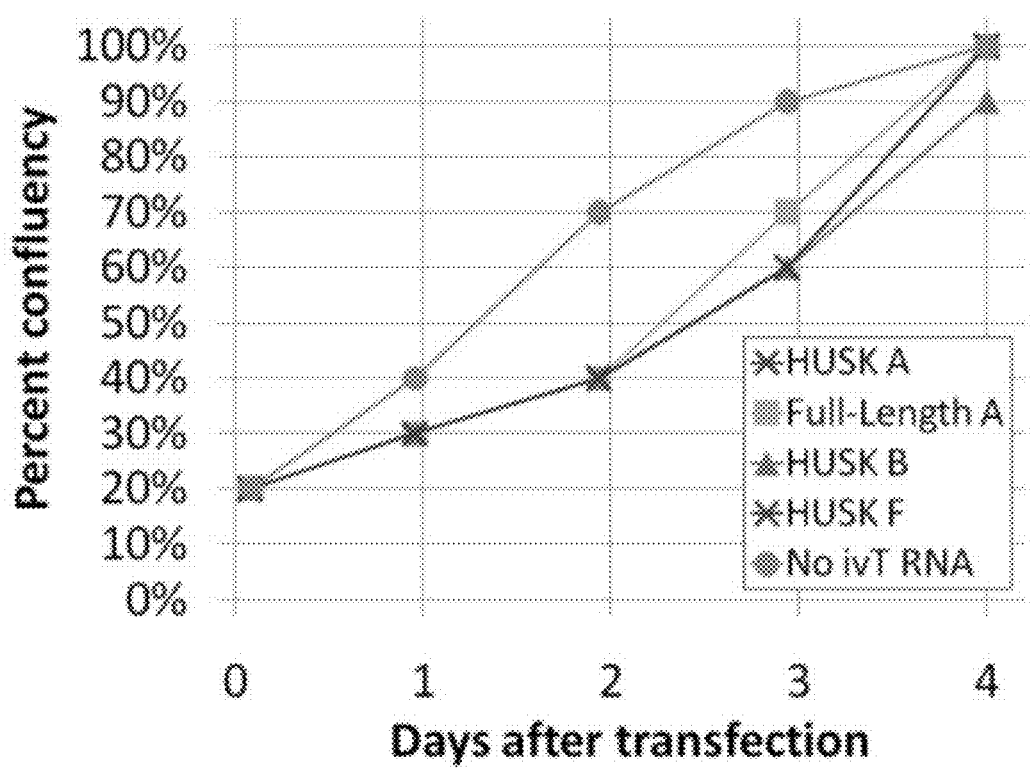

MRC-5 fibroblasts that were transfected with m7G capped, poly(A)-tailed HUSK ivT-RNA mounted an innate immune response as expected[54]. While mock-transfected cells recovered quickly, achieving a normal population-doubling time within 24 hours, cells transfected with HUSK ivT-RNA failed to proliferate for approximately 36 hours; they then recovered, achieving a normal doubling time only 48 hours after transfection. The duration of the cytostatic effect of HUSK ivT-RNA transfection corresponded roughly to the measured intracellular lifetime of the HUSK ivT-RNA (FIG. 2A); transfection with transcripts encoding proteins with both short (less than 24 h) and long (greater than 48 h) lifetimes yielded similar results (FIG. 4B). These results show that reduced cell proliferation is a reaction to the HUSK ivT-RNA itself, and not to the encoded protein.

Figure 5:
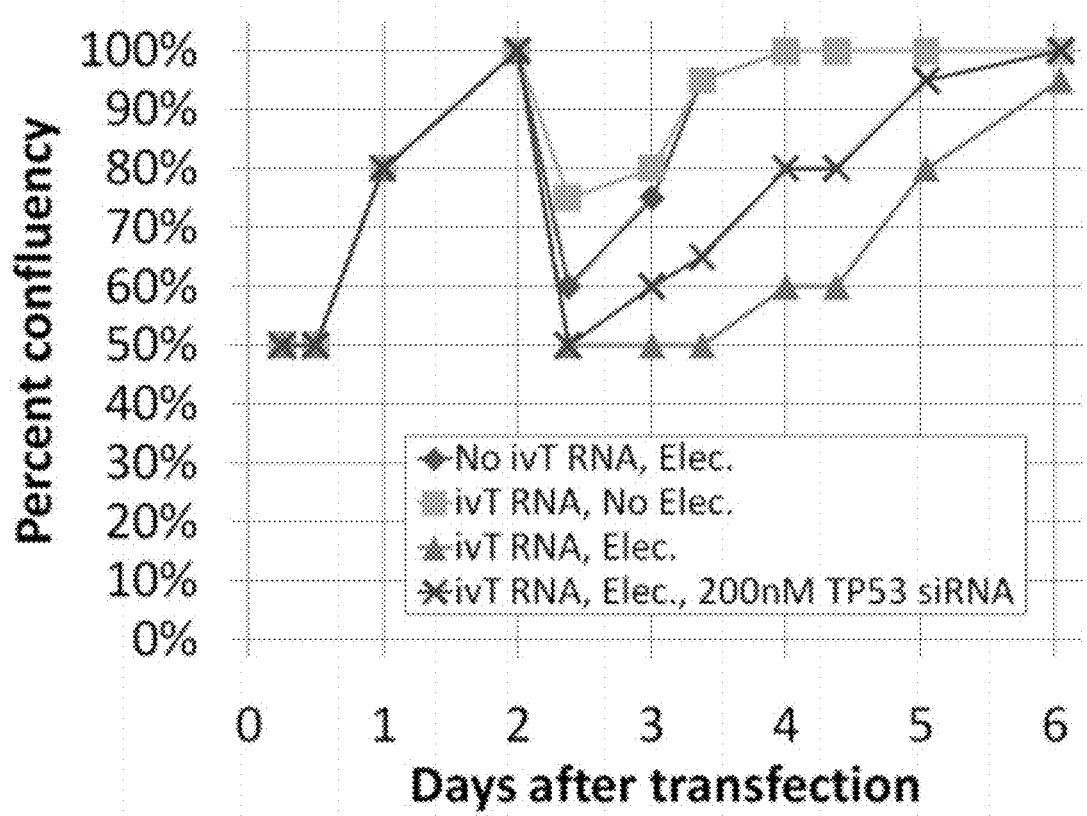

It was discovered that siRNA-mediated knockdown of p53 increased the rate of recovery of cells transfected with ivT-RNA, showing that p53-mediated cell-cycle arrest and/or -apoptosis contributed to the observed cytostatic effect of HUSK ivT-RNA transfection (FIG. 5). The cytostatic effect of HUSK ivT-RNA transfection determined in MRC-5 fibroblasts electroporated in Opti-MEM (Invitrogen) containing 200 nM TP53 siRNA is indicated on the figure. The cells were plated in 10 cm dishes at a density of $2.5 \times 10^6$ cells per dish on day 0. Two days later, the cells were suspended by trypsinization and electroporated with 3.5 μg HUSK ivT RNA or 3.5 μg HUSK ivT RNA and 200 nM TP53 siRNA as indicated. Only the cells that received siRNA on day 0 received additional siRNA on day 2. The confluency of each dish was monitored for several days. Cells that were not transfected with HUSK ivT RNA (squares, diamonds) recovered quickly after the second electroporation approaching confluency at day 3.5, while cells that were transfected with HUSK ivT RNA (triangles) exhibited delayed growth, and only approached confluency at day 6. Interestingly, cells transfected with TP53 siRNA (crosses) showed an increased rate of recovery after HUSK ivT-RNA delivery, approaching confluency at day 5, showing that the cytostatic effect of HUSK ivT-RNA transfection may be due in part to activation of a p53-dependent pathway. TP53 is the name of the human gene that encodes the protein known as p53. Data points are connected for clarity.

Several innate-immune pathways activated by exogenous RNA transfection are known. Toll-like receptor 3 (TLR3),[53, 54] toll-like receptor 7 (TLR7),[55] and retinoic-acid receptor responder (tazarotene induced) 3 (RARRES3)[56-58] are the three pattern-recognition receptors (PRRs) for which RNA is a known pathogen-associated molecular pattern (PAMP) in humans. Once exogenous RNA is detected by these receptors, they initiate cascades of intracellular signaling that upregulate interferon-β (IFNB1), a cytokine that is secreted into the culture media where it binds to cell-membrane-associated receptors. These receptors in turn initiate signaling cascades that lead to a full innate-immune response characterized by growth inhibition, eukaryotic translation initiation factor 2-alpha kinase 2 (EIF2AK2)-mediated translation inhibition[59, 60], upregulation of PRRs which hypersensitizes the cells to PAMPs, and upregulation of type I interferons which are secreted by the cells; all of which amplify the immune response. In addition, many interferon-stimulated genes (ISGs, also known as interferon-responsive genes or IRGs) such as OAS1, OAS2, OAS3, OASL, ISG20, and IFIT1 become upregulated in response to exposure to type I interferons. If uncontrolled, the innate-immune response can lead to apoptosis.

Figure 6:
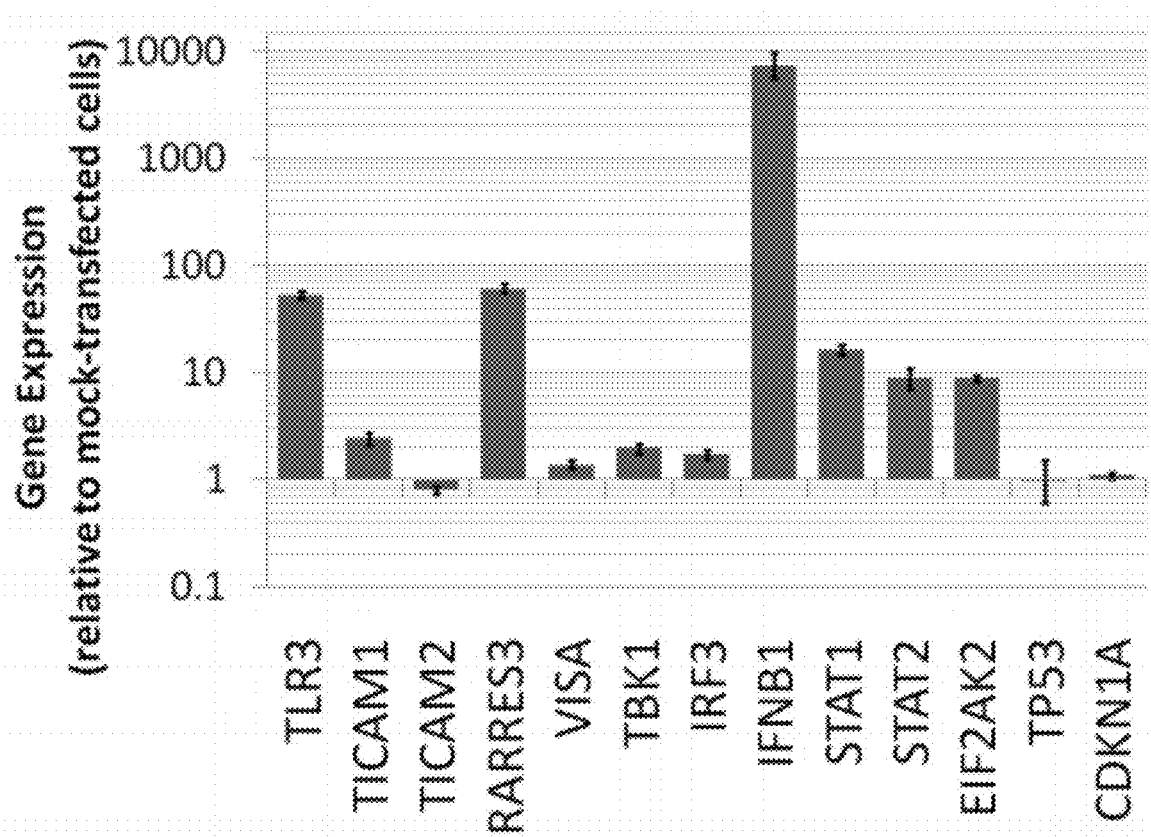

Quantitative RT-PCR conducted to measure IFNB1 expression revealed that IFNB1 was 7500-fold over expressed in cells transfected with HUSK ivT-RNA compared to mock-transfected cells 24 hours after transfection. There was also a >50-fold over expression of TLR3 and RARRES3, >10-fold over expression of signal transducer and activator of transcription 1 (STAT1), and a >5-fold over expression of signal transducer and activator of transcription 2 (STAT2) and EIF2AK2, indicating a type I-interferon response and hypersensitization of the cells to exogenous RNA (FIG. 6).

To determine whether the innate-immune response elicited by HUSK ivT-RNA transfection was affected by the length or sequence of the RNA, cells were transfected with HUSK Transcript A, B, or F, or full-length unmodified endogenous Transcript A. IFNB1 expression was measured after 24 hours (FIG. 4A). Surprisingly, HUSK Transcript F and full-length Transcript A elicited 10-20-fold less IFNB1 over expression compared to mock-transfected cells than HUSK Transcript A or B. The observation that transfection with full-length endogenous Transcript A resulted in less IFNB1 over expression than transfection with HUSK Transcript A is likely explained by the shorter intracellular lifetime of the full-length transcript. However, the observation that transfection with HUSK Transcript F resulted in 20-fold less IFNB1 over expression than transfection with either HUSK Transcript A or B showed that the innate immune response is not caused primarily by the HBB UTRs, which were present in all three transcripts. Instead these data show that the strength of the innate immune response depends on the overall length of the RNA or on the sequence elements in the CDS.

Single-stranded RNA was shown to activate TLR3 based on the facts that toll-like receptor 7 (TLR7), the PRR for which single-stranded RNA is a known PAMP, was not expressed in MRC-5 fibroblasts (RT-PCR data not shown). By contrast TLR3 and RARRES3, the two PRRs for which double-stranded RNA is a known PAMP were expressed, also previous observations by others showed that ivT-RNA and mRNA can elicit a TLR3-dependent innate-immune response.[54, 61] Without being bound by theory, it is possible that long ssRNA molecules can possess significant secondary structure, which may bind to TLR3 and/or other dsRNA-specific PRRs thereby activating them. Longer ssRNA molecules with more secondary structure might elicit a stronger innate-immune response than shorter ssRNA molecules with less secondary structure. This hypothesis could explain the lower level of IFNB1 over expression that results from transfection with the HUSK Transcript F transcript compared to HUSK Transcript A, as HUSK Transcript A is approximately twice as long as HUSK Transcript F. Also, it is likely that the observed difference in IFNB1 over expression is due to specific sequence elements present in the three HUSK transcripts tested.

Figure 7A:
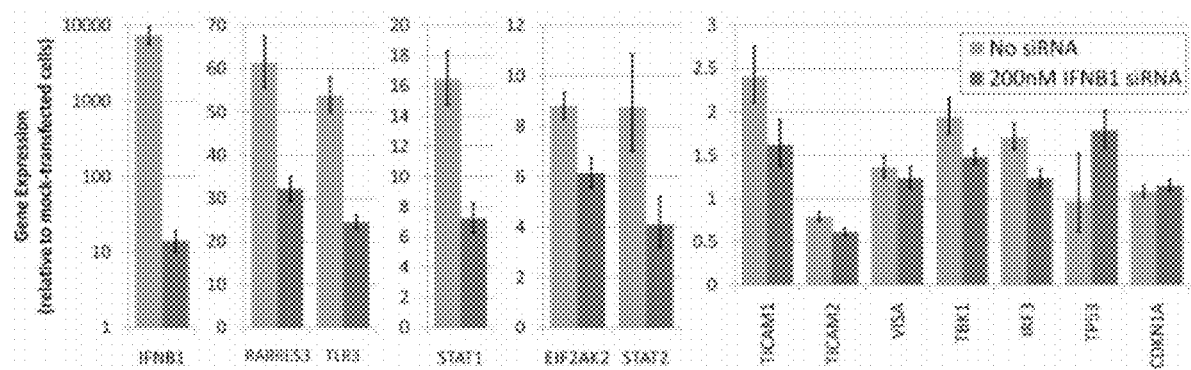
Figure 7B:
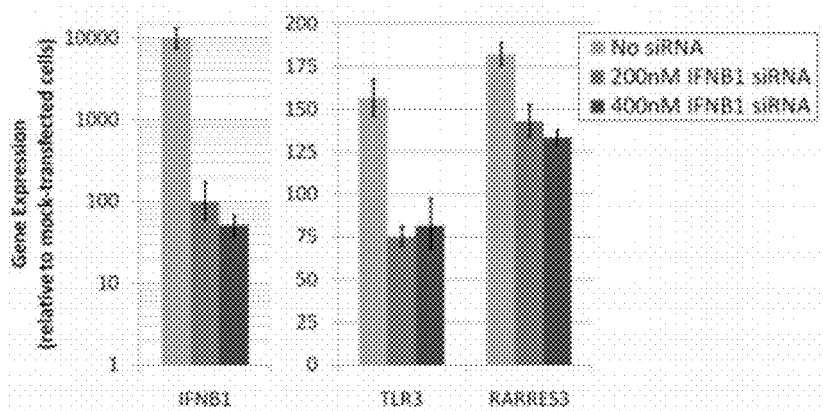

The innate immune response represents a significant obstacle to any strategy of extended transient transfection based on frequent, repeated delivery of exogenous RNA, a known PAMP. To disrupt the innate-immune response, siRNA targeting IFNB1 was introduced to the cells to knock down its expression. The IFNB1 siRNA was delivered to MRC-5 fibroblasts by electroporation, with or without HUSK ivT-RNA. While the cells that received no siRNA exhibited a 10,000-fold over expression of IFNB1 24 hours after HUSK ivT-RNA transfection compared to mock-transfected cells, the cells that received both siRNA and HUSK ivT-RNA exhibited only 50-100-fold over expression of IFNB1 compared to mock-transfected cells, corresponding to a knockdown efficiency of 99-99.5% (FIG. 7B).

To give the RNAi machinery more time to locate and bind the siRNA before HUSK ivT-RNA transfection, cells were electroporated with siRNA, allowed to grow for 48 hours, and then electroporated again with both siRNA and HUSK ivT-RNA. Routine experimentation will determine if a shorter or longer interval between siRNA administration and the first transfection can be used. In this experiment, cells that received no siRNA showed a 7500-fold over expression of IFNB1 relative to mock-transfected cells, while the cells that received siRNA showed a 15-fold over expression of IFNB1 relative to mock-transfected cells, corresponding to a knockdown efficiency of 99.8% (FIG. 7A). The differences in IFNB1 over expression in cells that received only HUSK ivT-RNA, were likely due to small variations in the extremely low level of IFNB1 endogenously expressed by MRC-5 cells. For this reason, levels of over expression should only be compared within and not between experiments, as each experiment has an independent mock-transfection control to which all expression data in that experiment are normalized.

Figure 9A:
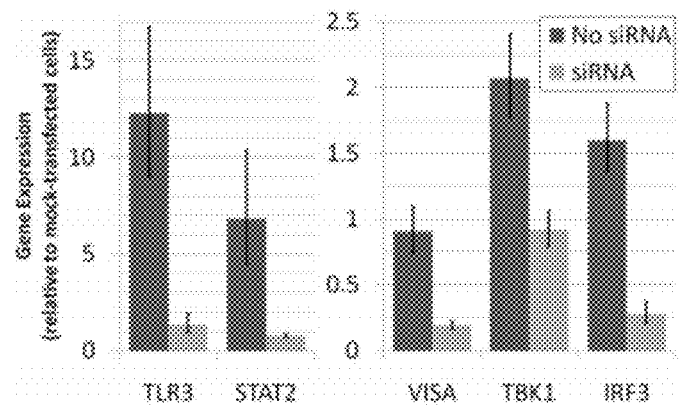
Figure 9B:
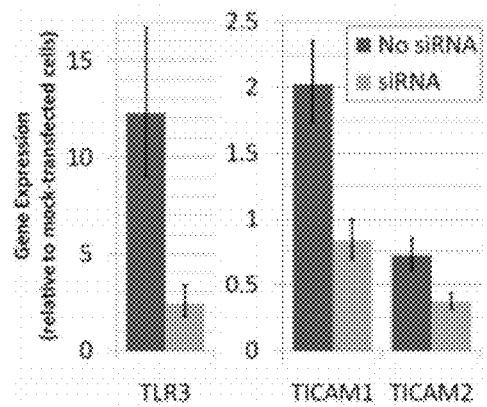
Figure 9C:
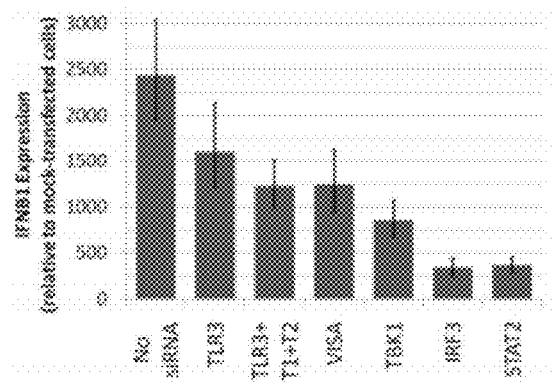
Figure 9D:
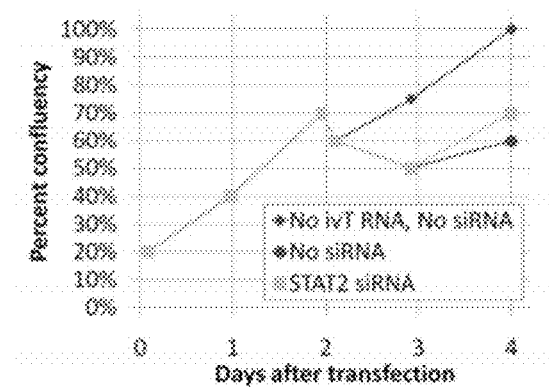
Figure 10A:
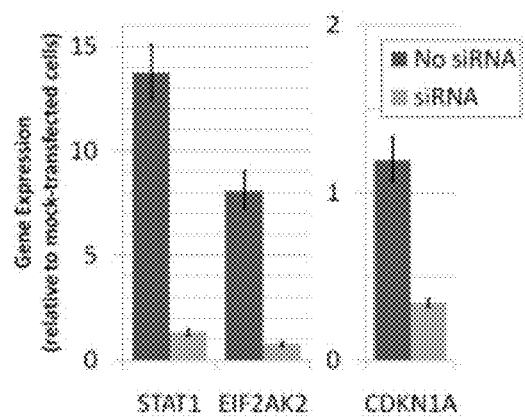
Figure 10B:
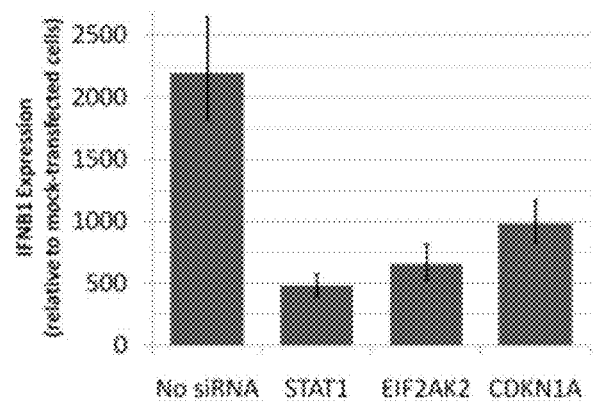

Knockdown efficiencies observed with electroporation in MRC-5 fibroblasts using commercially-available siRNAs from the same vendor targeting other known genes or mRNAs are typically between 80% and 90% (FIG. 9 and FIG. 10). The commercially-available siRNAs used are listed in Table A1 with their product numbers. siRNA vendors include: Applied Biosystems, Ambion, Promega, and Santa Cruz Biotechnology. All of the siRNAs that we used were "Silencer Select" siRNAs from Applied Biosystems.

The high efficiency of IFNB1 knockdown observed shows that enough IFNB1 mRNA was destroyed by the RNAi machinery to disrupt the interferon-β-mediated amplification of the innate-immune response elicited by HUSK ivT-RNA transfection. This is consistent with the observation that several other genes involved in the innate immune response, although still over expressed relative to mock-transfected cells, are significantly less over expressed in cells that received siRNA targeting IFNB1 than in cells that received no siRNA (FIG. 7). In particular, the PRRs TLR3 and RARRES3, which are 50-60-fold over expressed in cells that received only HUSK ivT-RNA, are 20-30-fold over expressed in cells that received both HUSK ivT-RNA and IFNB1 siRNA. In addition, STAT1, STAT2, and EIF2AK2 all showed a similar reduction in the level of over expression relative to mock-transfected cells when cells were co-transfected with HUSK ivT-RNA and IFNB1 siRNA.

Figure 8A:
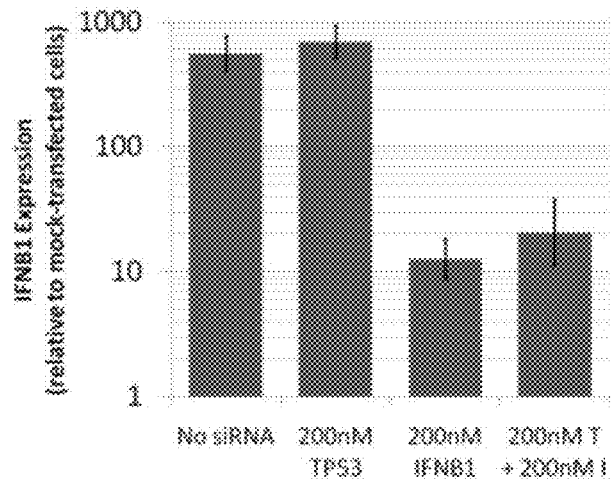
Figure 8B:
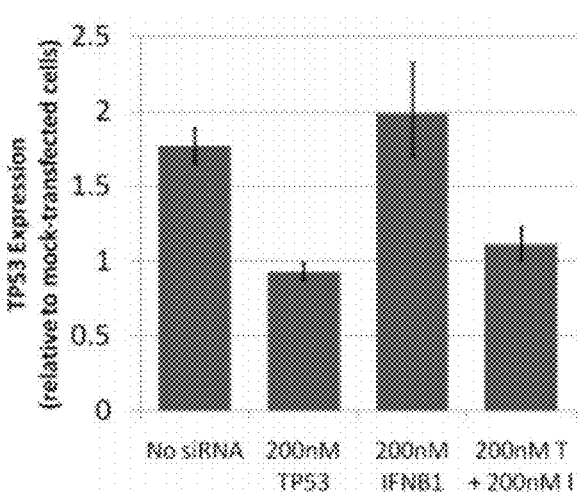
Figure 8C:
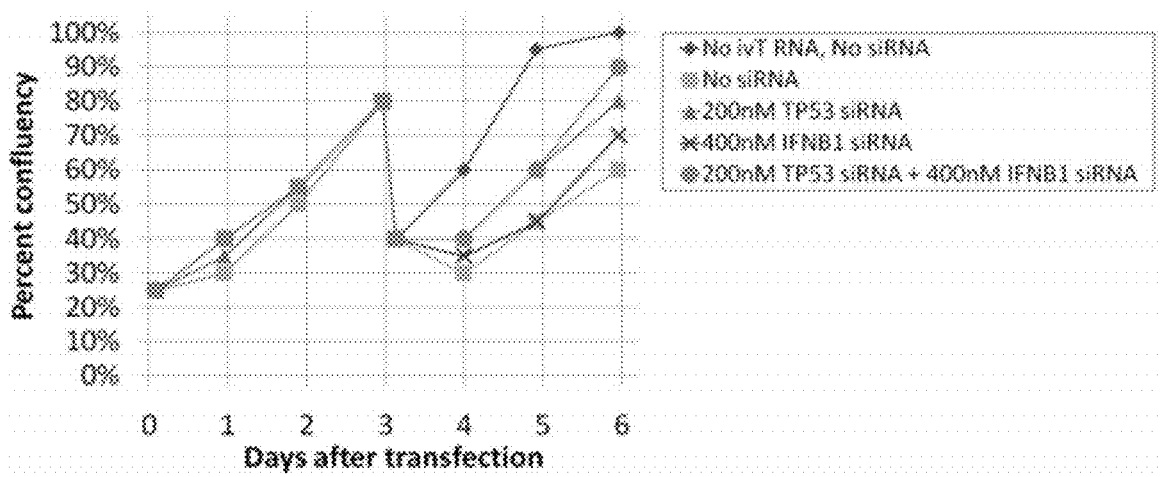

Although siRNA-mediated IFNB1 knockdown reduced the over expression of several proteins involved in the innate-immune response elicited by HUSK ivT-RNA transfection in MRC-5 cells, innate immunity was not completely inhibited in these cells as indicated by the remaining >20-fold over expression of the PRRs TLR3 and RARRES3 and >5-fold over expression of IFNB1, STAT1, and EIF2AK2. Experiments on IFNB1 knockdown appeared to have little or no effect on the inhibition of proliferation observed in ivT-RNA-transfected cells (FIG. 8), showing that in cells transfected with both HUSK ivT-RNA and IFNB1 siRNA, either the remaining low level of IFNB1 expression is sufficient to prevent the cells from proliferating or the cells are prevented from proliferating by a mechanism independent of interferon-β such as interferon-α signaling. Details are presented in Example 3.

The known proteins in the human innate immune response pathway include TP53, TLR3, TLR7, RARRES3, IFNA1, IFNA2, IFNA4, IFNA5, IFNA6, IFNA7, IFNA8, IFNA10, IFNA13, IFNA14, IFNA16, IFNA17, IFNA21, IFNK, IFNB1, IL6, TICAM1, TICAM2, MAVS, STAT1, STAT2, EIF2AK2, IRF3, TBK1, CDKN1A, CDKN2A, RNASEL, IFNAR1, IFNAR2, OAS1, OAS2, OAS3, OASL, RB1, ISG15, ISG20, IFIT1, IFIT2, IFIT3, and IFIT5, and biologically-active fragments, analogs and variants thereof. The mRNA and gene sequences encoding these innate immune response proteins that can be targeted with siRNA or antisense oligonucleotides are listed in Table 3 where they are identified by their official accession numbers. The full mRNA and gene sequences are readily available. A person of skill in the art can make antisense or siRNA to reduce expression of any of these proteins using routine experimentation as described below by interfering with the transcription of the gene or mRNA or both encoding the various target proteins. Other animals express closely related proteins with a high degree of sequence homology to the human proteins; these analogs can also be targeted for suppression. Any cells that mount an innate immune response can be similarly treated to human cells, and many of the siRNAs and antisense nucleotides that work in humans will work in other animal cells to suppress the response.

Figure 10C:
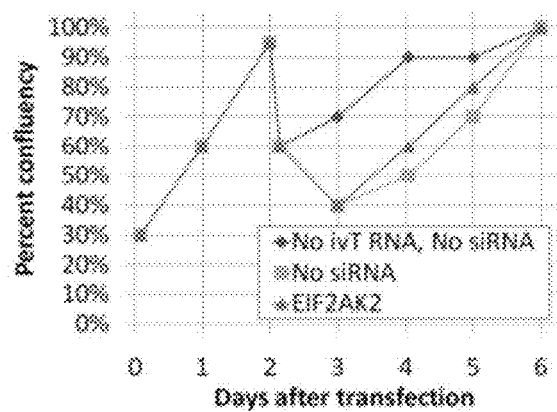

Although the innate-immune response is initiated and regulated by intra- and extracellular signaling pathways containing a great deal of redundancy, many viruses have evolved mechanisms to disrupt innate-immune signaling, enabling persistent infection (for a recent review of innate-immune disruption by Hepatitis C, a ssRNA virus, see Bode, 2007). To test whether RNAi knockdown of one or more of the factors involved in innate-immune signal transduction would inhibit the innate-immune response elicited by HUSK ivT-RNA transfection, various combinations of siRNAs targeting TLR3, TICAM1, TICAM2, VISA, TBK1, IRF3, STAT1, STAT2, EIF2AK2, TP53, and CDKN1A were delivered to cells by electroporation 48 hours before a second electroporation with HUSK ivT-RNA and additional siRNA. The levels of expression of IFNB1 and the genes targeted for knockdown were measured 24 hours after the second electroporation by quantitative RT-PCR (FIG. 9A-C; FIG. 10A, B). Transfections were split into two independent experiments to minimize sample-handling time. Transfected cells were monitored for several days, and estimates of confluency were made each day to determine if knocking down the selected genes had an effect on cell proliferation (FIG. 9D, FIG. 10C).

Although knocking down any of the selected genes resulted in a significant reduction of IFNB1 over expression, only knockdown of STAT2 or EIF2AK2 had an observed effect on cell proliferation. Therefore in an embodiment the knockdown cocktail includes siRNA or antisense oligonucleotides that reduce expression of STAT2 or EIF2AK2. The effect of knocking down either STAT2 or EIF2AK2 was characterized by a shortened recovery time after HUSK ivT-RNA transfection. In both cases, cells co-transfected with siRNA and HUSK ivT-RNA appeared to reach the same level of confluency as mock-transfected cells after approximately 36 hours, as opposed to the 48 hours required for the no-siRNA control. As opposed to TP53-knockdown, which resulted in an increased confluency in knockdown cells compared to the no-siRNA control only 24 hours after transfection (FIG. 5), the increased confluency of STAT2 and EIF2AK2 knockdown cells compared to the no-siRNA control was first observed 48 hours after transfection, showing that while STAT2 or EIF2AK2 knockdown alone may be insufficient to inhibit the innate-immune response elicited by HUSK ivT-RNA transfection, knocking down these genes may contribute to an increased rate of recovery after the HUSK ivT-RNA has been degraded by the cell.

Because the innate immune response is accompanied by an accumulation of inflammatory cytokines such as interferon-$\beta$ in the culture media, the culture media can be replaced at least once shortly after transfection (preferably between 15 minutes and 48 hours after transfection, more preferably between 2 and 12 hours after transfection) to remove these cytokines, thus further suppressing the innate immune response.

In addition to the use of small-molecule inhibitors and siRNA, antibodies against cytokines released after ivT-RNA transfection (such as the Type I interferons) as well as antibodies against the receptors for these cytokines (such as the interferon-alpha receptor) can be added to the culture media to suppress the innate-immune response elicited by ivT-RNA transfection (see LaFleur, et al. "Interferon-κ, a Novel Type I Interferon Expressed in Human Keratinocytes." J. of Biol. Chem. Vol. 276, No. 43. 2001). The antibodies can be used to suppress the immune response together with siRNA and antisense oligonucleotides or alone. In a preferred embodiment the antibodies are monoclonal antibodies, such as mouse anti-human IFN-α/β receptor chain 2 (CD118) (clone: MMHAR-2, IgG2a, PBL Biomedical Laboratories, New Brunswick, N.J.).

Extended Transient Transfection by Repeated Delivery of In Vitro-transcribed RNA Maintains a High Level of Encoded Protein Expression Through Multiple Cell Divisions The results described here show that increased quasi-stable expression of ivT-RNA-encoded protein (also referred to as transduced protein expression) was achieved with frequent, repeated transfection of cultured cells with the appropriate HUSK ivT-RNA, at intervals for example about 24-48 hours apart. This range will vary based on the cell type, the protein being expressed, etc. It was further discovered that a normal rate of cell proliferation after repeated HUSK ivT-RNA transfection at 24 hour intervals compared to mock-transfected cells could be maintained if (1) the innate-immune response of MRC-5 human fibroblasts to exogenous RNA was suppressed by combined knockdown using an siRNAs cocktail targeting several proteins in the innate immune response pathway, preferably before the first transfection, and (2) transfection was accomplished using an electroporation protocol designed to minimize cellular stress.

In order to maintain the high level of expression that was initially achieved during the first 18-24 hours following the first transfection with HUSK Transcripts A and B through multiple generations of cells, i.e. multiple rounds of cell division, additional transfections were performed at intervals of for example 24 to 48 hours from the previous transfection. The amount of HUSK ivT-RNA-encoded protein expressed was further increased and stabilized over multiple rounds of cell division by repeating immune response suppression, preferably at least about every 48 hours. The repeated transfection method is referred to as extended transient transfection by repeated delivery of HUSK ivT-RNA and is described in more detail below. It should be noted that achieving long-term encoded protein expression through multiple rounds of cell division does not require that the cells be synchronized, although they may be. The frequency of immune suppression and transfection will vary for example based on the cell type and the protein being expressed.

Three methods were identified that each mitigate to some degree the innate-immune response elicited by HUSK ivT-RNA transfection as measured both by reduced IFNB1 expression and by shortened post-transfection recovery time: 1. TP53 knockdown, 2. Innate-immune-response-amplification disruption by IFNB1 knockdown, and 3. Innate-immune-response inhibition by knockdown of additional genes involved in innate-immune signal transduction including the proteins in the innate immune suppression pathway described herein. These three methods were combined to determine whether cells could be repeatedly transfected with HUSK ivT-RNA using a transfection frequency on the order of the intracellular lifetime of the respective encoded protein, to achieve a high level of expression sustained through multiple rounds of cell division. The preferred frequency of repeated transfection is approximately equal to the intracellular lifetime of the respective encoded protein. If a downstream target of the encoded protein is highly stable, then the frequency of transfection may be determined by the intracellular lifetime of the downstream protein, for example. This is particularly important where the goal is to change the transfected cell's phenotype.

Figure 11A:
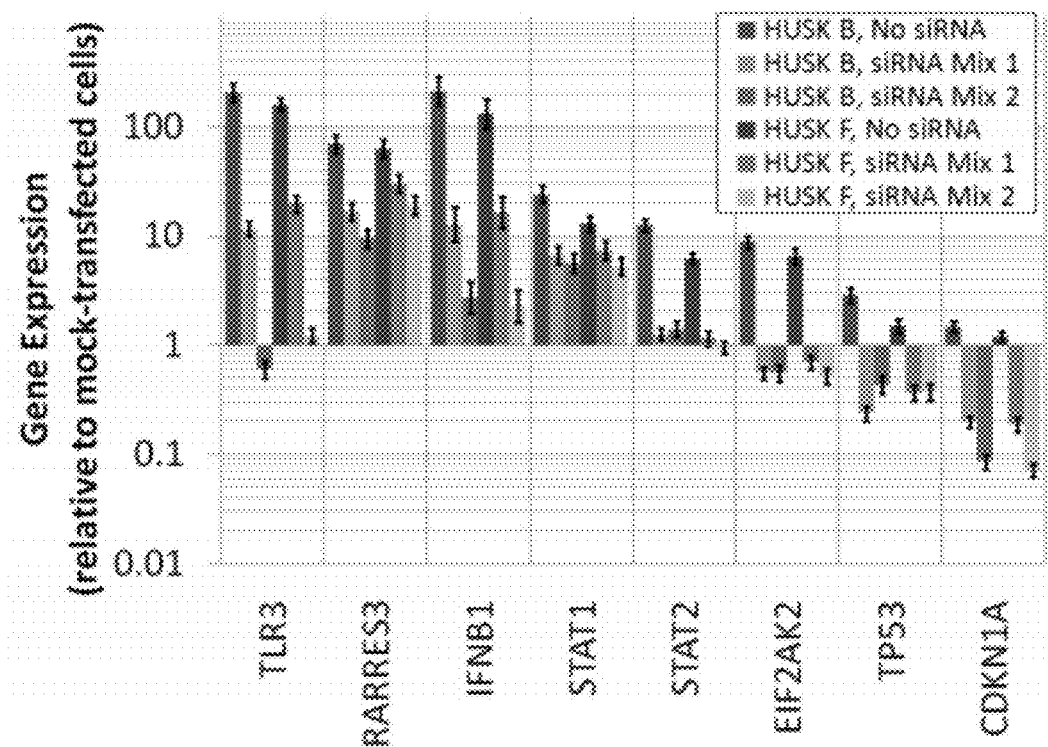

MRC-5 fibroblasts were transfected with siRNA Mix 1 (400 nM TP53, 200 nM STAT2, and 200 nM EIF2AK2) or siRNA Mix 2 (400 nM TP53, 200 nM STAT2, 200 nM EIF2AK2, 200 nM IFNB1, 200 nM TLR3, and 200 nM CDKN1A), and then repeatedly transfected with HUSK ivT-RNA over the course of several days. The expression of genes that were previously found to be >5-fold over expressed in ivT-RNA-transfected cells (TLR3, RARRES3, IFNB1, STAT1, STAT2, and EIF2AK2), as well as the expression of TP53 and CDKN1A were measured 24 hours after the first transfection with HUSK ivT-RNA to determine both the knockdown efficiency of each siRNA under these conditions, and the effectiveness of each siRNA mixture in inhibiting the innate-immune response elicited by HUSK ivT-RNA transfection (FIG. 11A).

FIGS. 13A-F show the response of downstream targets of the proteins encoded by various HUSK ivT RNAs after single and repeated transfections with the respective nucleic acids. Together these results show that repeated transfection with HUSK ivT RNA yields a high level of functional protein that can be sustained for many days.

In cells transfected with siRNA Mix 1, expression of all of the genes measured was reduced compared to mock-transfected cells, with several genes (TLR3, IFNB1, STAT2, and EIF2AK2) showing >90% knockdown. In cells transfected with siRNA Mix 2, expression of many of the genes measured was reduced further, and in these cells only RARRES3 and STAT1 (the two genes not targeted with siRNA) were >5-fold over expressed compared to mock-transfected cells, although both were significantly less over expressed than in cells that received no siRNA.

Figure 11B:
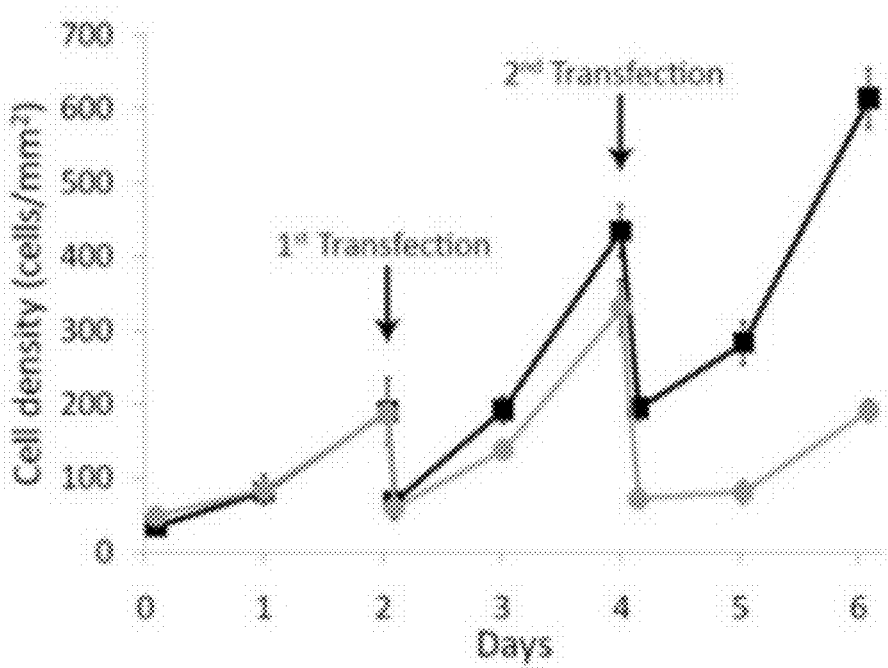
Figure 11C:
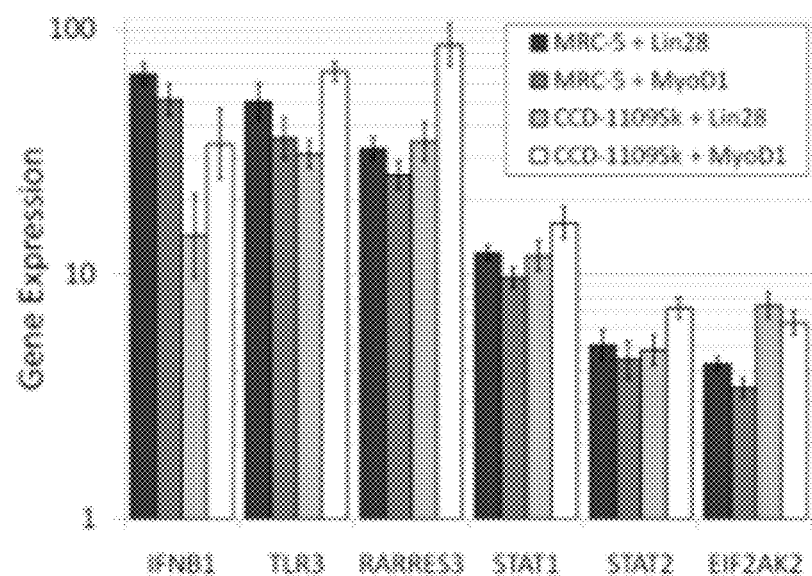
Figure 11D:
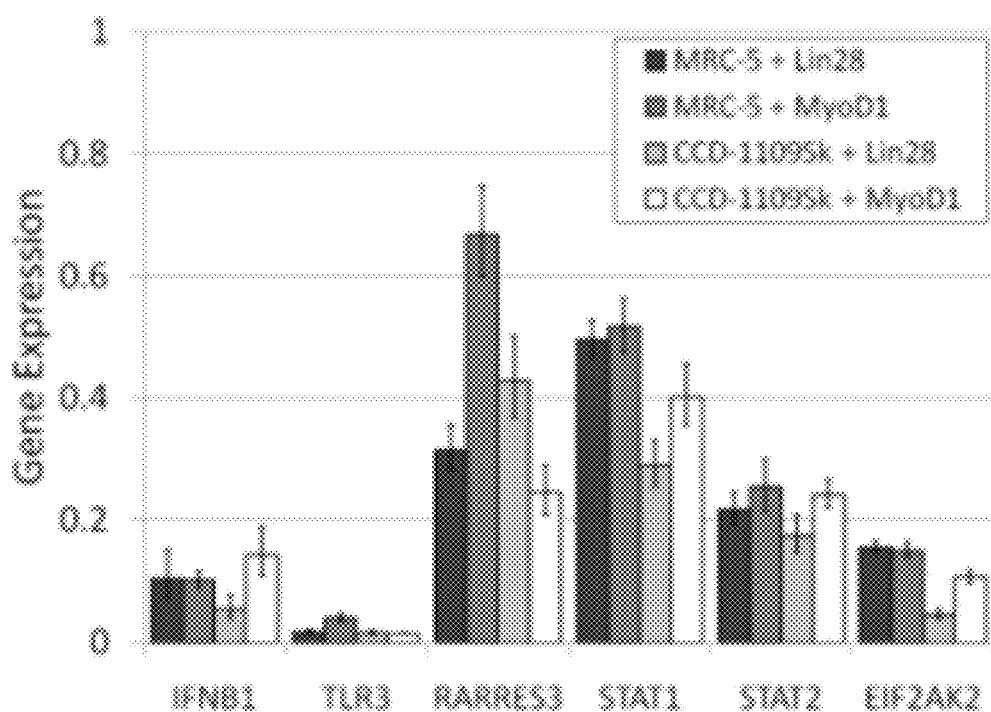

FIGS. 11B, 11C, and 11D and Table 1 describe a more thorough analysis of rescue by siRNA transfection from HUSK ivT-RNA transfection. FIG. 11B. MRC-5 fibroblasts were transfected twice with 0.5 μg Lin28-encoding HUSK ivT-RNA at a 48-hour interval. FIG. 11C shows cells were transfected as in (11B), but mock-transfected on day 2 and transfected on day 4 with 0.5 μg of either Lin28 or MyoD1-encoding HUsKe ivT-RNA. Gene expression was measured by RT-PCR 24 hours after the second transfection (day 5). Values are given relative to mock-transfected cells. FIG. 11D shows cells that were transfected as in (11B), but with a cocktail of siRNA targeting IFNB1, EIF2AK2, STAT2, and TLR3 on day 2, and 0.5 μg of either Lin28 or MyoD1-encoding HUSK ivT-RNA and additional siRNA on day 4. Gene expression was measured 24 hours after the second transfection (day 5). Values are given relative to cells that received no siRNA. These results showed that ivT-RNA transfection elicits an innate-immune response characterized by decreased proliferation and over expression of genes in the innate-immune pathway, and also that transfecting cells with a combination of siRNAs targeting genes in the innate-immune pathway not only reduced the over expression of the genes targeted by siRNA, but also reduced the over expression of other genes in the innate-immune pathway, indicating a general suppression of the innate-immune response. The data in Table 1 clearly demonstrate that simultaneously knocking down a small number of genes in the innate-immune pathway (specifically IFNB1, EIF2AK2, and STAT2) is sufficient to rescue cells from ivT-RNA transfection. Combined knockdown of these genes eliminated the reduction in proliferation caused by ivT-RNA transfection under these conditions, and therefore specifically enabled frequent, repeated transfection with ivT RNA, which the cells would not otherwise have survived.

Table 2 provides a table showing that combined knockdown of IFNB1, EIF2AK2, and STAT2 rescues cells transfected with ivT-RNA. MRC-5 fibroblasts were transfected as in FIG. 11B, but with siRNA on day 0, and 0.5 μg Lin28-encoding HUSK ivT-RNA and additional siRNA on days 2 and 4. Twenty-four hours after the second ivT-RNA transfection (day 5) samples of cells were trypsinized and counted. Values represent cell density relative to mock-transfected cells.

TABLE 2

| siRNA Mixture* | Relative Cell Density | s.e.m.† |
|---|---|---|
| No siRNA | 0.29 | 0.07 |
| I | 0.45 | 0.08 |
| E | 0.47 | 0.08 |
| T3 | 0.06 | 0.07 |
| S2 | 0.21 | 0.07 |
| S1 | 0.19 | 0.07 |
| TP | 0.20 | 0.07 |
| C | 0.34 | 0.07 |
| R | 0.05 | 0.07 |
| I + E | 0.65 | 0.09 |
| I + E + T3 | 0.67 | 0.09 |
| I + E + S2 | 0.95 | 0.11 |
| I + E + T3 + S2 | 0.98 | 0.09 |
| I + E + T3 + S1 + S2 | 0.95 | 0.11 |
| I + E + T3 + S2 + TP + C | 1.04 | 0.11 |
| I + E + T3 + S1 + S2 + TP + C + R | 0.84 | 0.09 |

*I = IFNB1, E = EIF2AK2, T3 = TLR3, S1 = STAT1, S2 = STAT2, TP = TP53, C = CDKN1A, R = RARRES3. Each siRNA was used at a concentration of 200 nM.
†Values represent the standard error of replicate samples.

As was shown in FIG. 3, transfection with HUSK Transcript B resulted in significant protein expression for approximately 18-24 hours, while transfection with HUSK Transcript F resulted in significant protein expression for more than 48 hours. Further analysis of the time-evolution of expression after transfection with HUSK Transcript F revealed that the protein encoded by this transcript reached approximately 50% of its peak level 3 days after transfection. Because transfection with HUSK ivT-RNA resulted in decreased proliferation, the duration of protein expression measured in these experiments may be significantly longer than it would have been had the cells been actively proliferating.

Figure 12A:
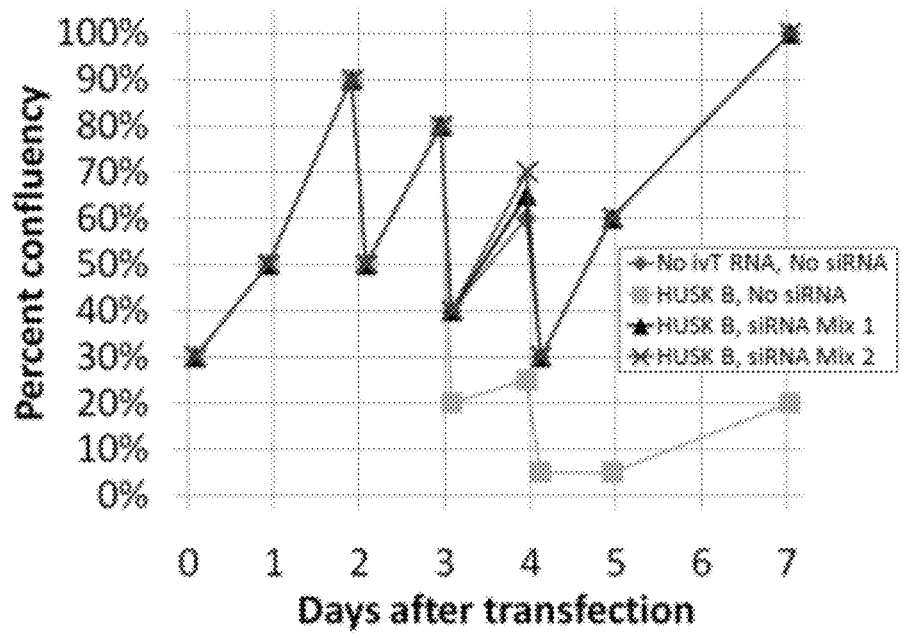
Figure 12B:
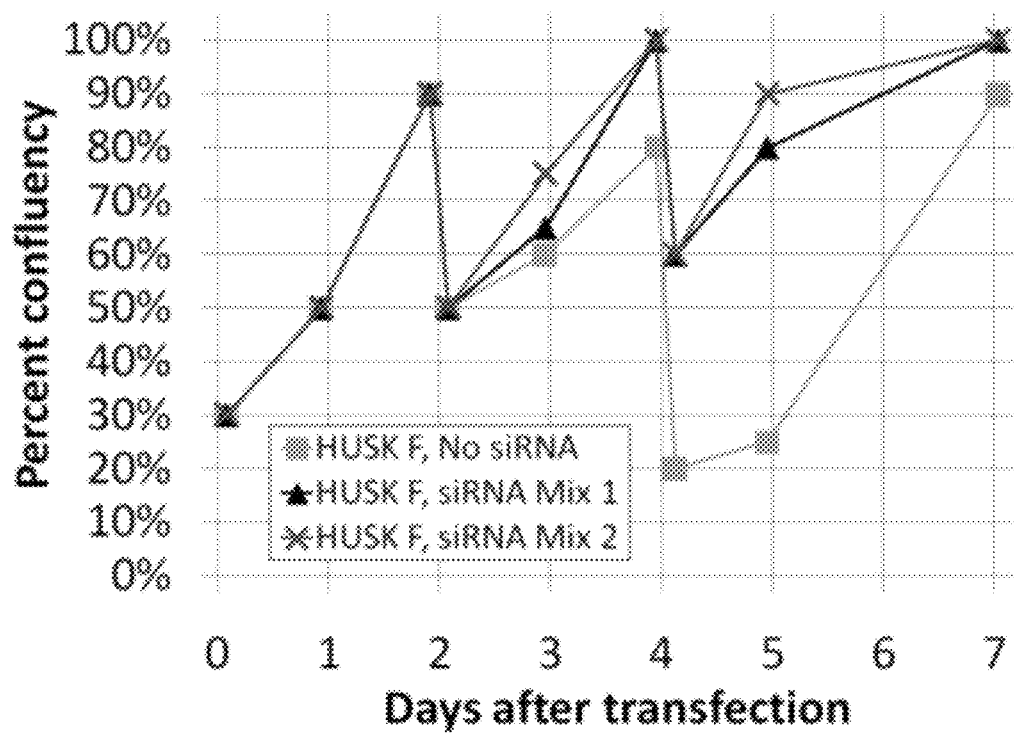

To achieve a sustained high level of protein, cells were transfected either with HUSK Transcript B, three times at 24-hour intervals, or with HUSK Transcript F, two times at a 48-hour interval. The confluency of each dish of transfected cells was monitored to determine the effect of co-transfection with HUSK ivT-RNA and siRNA Mix 1 or 2 on cell proliferation (FIG. 12). While cells recovered from the first transfection with HUSK ivT-RNA, many of the cells that did not receive siRNA died after the second HUSK ivT-RNA transfection, likely due to hypersensitization to exogenous RNA as indicated by >100-fold over expression of TLR3 and >50-fold over expression of RARRES3 compared to mock-transfected cells. Cells that received either siRNA Mix 1 or 2 exhibited high viability after every transfection, and the confluency of these cultures, an indication of proliferation, remained within 10% of that of the mock-transfected cells throughout the experiment. Interestingly, cells that were transfected with HUSK ivT-RNA and siRNA three times at 24-hour intervals recovered quickly enough that the confluency of these cultures decreased only by approximately 10% each day. Because of sample loss due to handling (trypsinizing, transferring into and out of the electroporation cuvette, etc.) and because after each transfection approximately 10-15% of the cells were reserved for protein and RNA analysis, the observed rate of recovery is likely high enough to allow an unlimited number of transfections at 24-hour intervals.

Whole-cell lysates were prepared every 12 hours after the first transfection with HUSK ivT-RNA (day 2), and the level of protein encoded by the HUSK ivT-RNA was assessed by western blot. Cells were transfected with only siRNA on day 0 and the first transfection with HUSK ivT-RNA occurred on day 2. ACTB was used as a loading control. The level of protein encoded by Transcript F reached approximately 50% of its peak level 3 days after a single transfection. By contrast, the cells transfected twice with Transcript F maintained a high level of protein expression through the third day after the first transfection, which increased slightly after the second transfection, and then fell to approximately 50% of its peak level on day 7, 5 days after the first transfection, and 3 days after the second (and last) transfection. This protein-expression profile, together with the fact that the transfected cells are proliferating rapidly (FIG. 12B), shows that an approximately steady-state level of the protein encoded by Transcript F was maintained through many cell divisions by repeated transfection even at 48-hour intervals.

By contrast the protein encoded by Transcript B however, although highly expressed 12 hours after each transfection, was barely detectable 24 hours after each transfection, showing that most of the protein produced as a result of each transfection was degraded by the time the following transfection was performed. Routine experimentation will determine the best protocol to achieve a desired level of protein-expression, such as more-frequent transfections, or transfection with a larger quantity of HUSK ivT-RNA.

For a protein with a half-life of 3 days (LIN28-TRANSCRIPT F), two transfections (48 hours) using this technique extended the effective protein half-life to 5 days, with a stable, high level of protein expression observed for the first 3 days after transfection. Repeated transfection with a less stable protein (intracellular lifetime of 18-24 hours, TRANSCRIPT B-SOX2) at intervals of 24 hours generated a high level of protein expression 12 hours after each transfection, which decreased before the next transfection, showing that more frequent transfections, may be required to achieve a stable level of expression of proteins with short intracellular lifetimes. Where the goal is to express one or more proteins at a level that induces a phenotypic change in the transfected cell, a high level of protein expression may only be required for a short time during each cell cycle to modify the epigenetic state of a target gene. Routine experimentation will show how to achieve level of stable protein expression sufficient to achieve gene activation.

Certain embodiments are directed to a method for suppressing the innate immune response of a cell to transfection with a nucleic acid, that can be either single or double-stranded DNA or DNA or DNA/RNA chimeras, by a. introducing to a cell an effective amount of an agent that reduces the expression of one or more proteins in the innate immune response pathway selected from the group consisting of TP53, TLR3, TLR7, RARRES3, IFNA1, IFNA2, IFNA4, IFNA5, IFNA6, IFNA7, IFNA8, IFNA10, IFNA13, IFNA14, IFNA16, IFNA17, IFNA21, IFNK, IFNB1, IL6, TICAM1, TICAM2, MAVS, STAT1, STAT2, EIF2AK2, IRF3, TBK1, CDKN1A, CDKN2A, RNASEL, IFNAR1, IFNAR2, OAS1, OAS2, OAS3, OASL, RB1, ISG15, ISG20, IFIT1, IFIT2, IFIT3, and IFIT5, or to a biologically-active fragment or analog thereof, hereafter "immune suppression proteins." In a preferred embodiment the agent is siRNA, antisense DNA or RNA, or a combination thereof. The embodiment can further include suppressing the innate immune response with antibodies that reduce the biological activity of one or more immune suppression proteins, or a protein or small molecule. By effective amount of siRNA or antisense oligonucleotide is meant an amount that reduces expression of the targeted protein. The accession numbers of the mRNAs and the genes encoding the human version of the immune suppression proteins are set forth in Table 3. As with the ivT-RNA encoded proteins, human immune suppression proteins have analogs in other animal species that have a sufficient amount of sequence homology to the human proteins such that they have the desired biological activity, and can therefore also be targeted for suppression. A person of skill in the art can make siRNA or antisense oligonucleotides to reduce expression of any of these proteins using routine experimentation as described in the relevant sections below.

Small inhibitory RNA targeting many of the immune suppression proteins, including those used, herein are available commercially. Compositions including mixtures of two or more siRNAs that block translation of the mRNA or gene encoding any of innate immune response proteins, including mixtures of commercially-available siRNAs, come within the scope of the present invention. Preferred compositions include the siRNA mixtures 1 and 2 described below, and a mixture of siRNAs targeting IFNB1, EIF2AK2, and STAT2.

Immunosuppressant drugs may be used to reduce the immune response elicited by ivT-RNA transfection. Although most act to prevent the activation of specific immune cells (lymphocytes, etc.), several of these drugs act on pathways that are active to some degree in a wide variety of cell types. The use of immunosuppressants may be particularly important when using the extended transient transfection method in vivo. Common immunosuppressants include: Tacrolimus, Cyclosporin, Pimecrolimus, Abetimus, Gusperimus, Thalidomide, Lenalidomide, Anakinra, Sirolimus, Deforolimus, Everolimus, Temsirolimus, and Zotarolimus. Certain embodime are directed to methods of suppressing the immune response in a cell transfected with a nucleic acid that include contacting the cell with one of these immunosuppressants.

An inhibitor of the protein encoded by EIF2AK2 called "RNA-Dependent Protein Kinase Inhibitor" is sold by EMD Biosciences (RNA-Dependent Protein Kinase Inhibitor, Catalog Number 527450) and may also be used suppress the innate immune response, alone or in combination with the above-described siRNAs and antisense oligonucleotides. In addition, an inhibitor of type I-interferon signaling such as B18R (sold as "Recombinant B18R protein, Vaccinia Virus-Encoded Neutralizing Type I Interferon Receptor; Type I IFN inhibitor by eBioscience, Inc., Catalog Number 14-8185) may also be used to suppress the innate immune response, alone or in combination with the above-described siRNAs, antisense oligonucleotides, and RNA-Dependent Protein Kinase Inhibitor.

TABLE 3

| Innate Immune Response Protein | mRNA Accession Number | NCBI GeneID |
| --- | --- | --- |
| TP53 | NM_000546, NM_001126112, NM_001126113, NM_001126114, NM_001126115, NM_001126116, NM_001126117 | 7157 |
| TLR3 | NM_003265 | 7098 |
| TLR7 | NM_016562 | 51284 |
| RARRES3 | NM_004585 | 5920 |
| IFNA1 | NM_024013 | 3439 |
| IFNA2 | NM_000605 | 3440 |
| IFNA4 | NM_021068 | 3441 |
| IFNA5 | NM_002169 | 3442 |
| IFNA6 | NM_021002 | 3443 |
| IFNA7 | NM_021057 | 3444 |
| IFNA8 | NM_002170 | 3445 |
| IFNA10 | NM_002171 | 3446 |
| IFNA13 | NM_006900 | 3447 |
| IFNA14 | NM_002172 | 3448 |
| IFNA16 | NM_002173 | 3449 |
| IFNA17 | NM_021268 | 3451 |

TABLE 3-continued

| Innate Immune Response Protein | mRNA Accession Number | NCBI GeneID |
| --- | --- | --- |
| IFNA21 | NM_002175 | 3452 |
| IFNK | NM_020124 | 56832 |
| IFNB1 | NM_002176 | 3456 |
| IL6 | NM_000600 | 3569 |
| TICAM1 | NM_182919 | 148022 |
| TICAM2 | NM_021649 | 353376 |
| MAVS | NM_020746 | 57506 |
| STAT1 | NM_007315, NM_139266 | 6772 |
| STAT2 | NM_005419 | 6773 |
| EIF2AK2 | NM_002759, NM_001135651, NM_001135652 | 5610 |
| IRF3 | NM_001571 | 3661 |
| TBK1 | NM_013254 | 29110 |
| CDKN1A | NM_000389, NM_078467 | 1026 |
| CDKN2A | NM_000077, NM_058195, NM_058197 | 1029 |
| RNASEL | NM_021133 | 6041 |
| IFNAR1 | NM_000629 | 3454 |
| IFNAR2 | NM_000874, NM_207584, NM_207585 | 3455 |
| OAS1 | NM_016816, NM_002534, NM_001032409 | 4938 |
| OAS2 | NM_016817, NM_002535, NM_001032731 | 4939 |
| OAS3 | NM_006187 | 4940 |
| OASL | NM_003733, NM_198213 | 8638 |
| RB1 | NM_000321 | 5925 |
| ISG15 | NM_005101 | 9636 |
| ISG20 | NM_002201 | 3669 |
| IFIT1 | NM_001548 | 3434 |
| IFIT2 | NM_001547 | 3433 |
| IFIT3 | NM_001549, NM_001031683 | 3437 |
| IFIT5 | NM_012420 | 24138 |

In another preferred embodiment immune suppression is repeated at least about every 48 hours. The siRNA or antisense oligonucleotides can be accomplished via electroporation, lipid-mediated transfection, ballistic transfection, magnetofection, peptide-mediated transfection, microinjection, or a combination thereof. Other embodiments are directed to methods for transfecting a cell with a nucleic acid including single or double-stranded DNA or RNA or chimeras thereof by a.) suppressing the innate immune response of the cell, and b.) introducing the nucleic acid into the cell.

In an embodiment the nucleic acid molecule encodes a protein or biologically-active fragment or analog thereof. In an embodiment where the nucleic acid is a DNA molecule, it may be one that encodes a desired mRNA, siRNA, or shRNA (short hairpin RNA which is an siRNA precursor), or an lnRNA (long noncoding RNA that can turn on a gene). The nucleic acid can be a single-stranded DNA or RNA molecule, and a double stranded DNA or RNA molecule or a single or double stranded DNA/RNA chimera Between steps a and b, the cell is incubated for a time and under conditions that allow suppression of the innate immune response and translation of the encoded protein or RNA, respectively. In the preferred embodiment the nucleic acid is single stranded ivT-RNA, preferably HUSK ivT-RNA. Steps a and b can be sequential or simultaneous. In a preferred embodiment the cell undergoes repeated immune suppression and transfection as often as needed to maintain expression of the encoded protein, or targeted protein at the desired level. In another embodiment when step a.) is performed for the first time, it is performed from up to about 24-72 hours before step b.). In a preferred embodiment the frequency of transfection is about equal to the intracellular life-time of the encoded protein. In another embodiment the transfecting step a.) is accomplished using electroporation, lipid-mediated transfection, ballistic transfection, magnetofection, peptide-mediated transfection, microinjection or combinations thereof.

The methods and constructs of the present invention can be used in vivo or in vitro. If in vivo, the preferred construct contains RNA so that there is no permanent genetic modification of the cell, preferably HUSK ivT-RNA.

The transfected cell can be an animal cell, preferably a human cell, or a bacterial, yeast, fungi, and plants. Repeated transfection with the HUSK ivT-RNA will increase and sustain expression of the encoded protein. Like animal cells, bacteria yeast and fungi mount an immune response to transfection with long nucleotides, however, the immune response proteins are different from the response in animals. The new methods of suppressing the immune response and repeated transfection will also work in these organisms by targeting the immune response proteins as described.

The results of the experiments to date showed that one siRNA transfection suppressed the immune response for about 48 hours. The duration of suppression may vary based on the cell type being transfected. Therefore routine experimentation will determine the optimum siRNA treatment schedule. In certain embodiments, the siRNA or antisense transfection step is repeated as often as needed to maintain the desired level of target protein (innate immune response protein) suppression. This is typically at least once every 48 hours. Suppression of the innate immune response of cells to be transfected with ivT-RNA can be repeated with each subsequent ivT-RNA transfection, or less frequently if ivT-RNA transfection is more frequent than every 48 hours.

Certain other embodiments are directed to a cell in which the innate immune response to transfection with a nucleic acid such as in vitro-transcribed RNA is suppressed, and to cells that are both immune suppressed and transfected with a nucleic acid.

In addition to the use of small-molecule inhibitors and siRNA, antibodies against cytokines released after ivT-RNA transfection (such as the Type I interferons) as well as antibodies against any of the innate immune response proteins or against the receptors for these cytokines (such as the interferon-alpha receptor) can be added to the culture media to suppress the innate-immune response elicited by ivT-RNA transfection (see LaFleur, et al. "Interferon-κ, a Novel Type I Interferon Expressed in Human Keratinocytes." J. of Biol. Chem. Vol. 276, No. 43. 2001).

In certain other embodiments, the methods for suppressing the innate immune response combined with nucleic acid delivery involve suppressing the immune response genetically for example by transient or stable DNA transfection or viral transduction of shRNA or by the use of cells derived from knockout animals or animals with a mutation in one or more genes in the innate immune response pathway or any combination thereof. Cells that have been genetically transformed can be used for screening different ivT RNAs to find the ivT RNAs necessary to generate different desired phenotypic changes, for example.

Phenotypic Changes Due to Expression of ivT-RNA-encoded Proteins

FIGS. 13A-F show the response of downstream targets of the proteins encoded by various HUSK ivT RNAs after single and repeated transfections with the respective nucleic acids. Together these results show that repeated transfection with HUSK ivT RNA yields a high level of functional protein that can be sustained for many days.

Figure 13A:
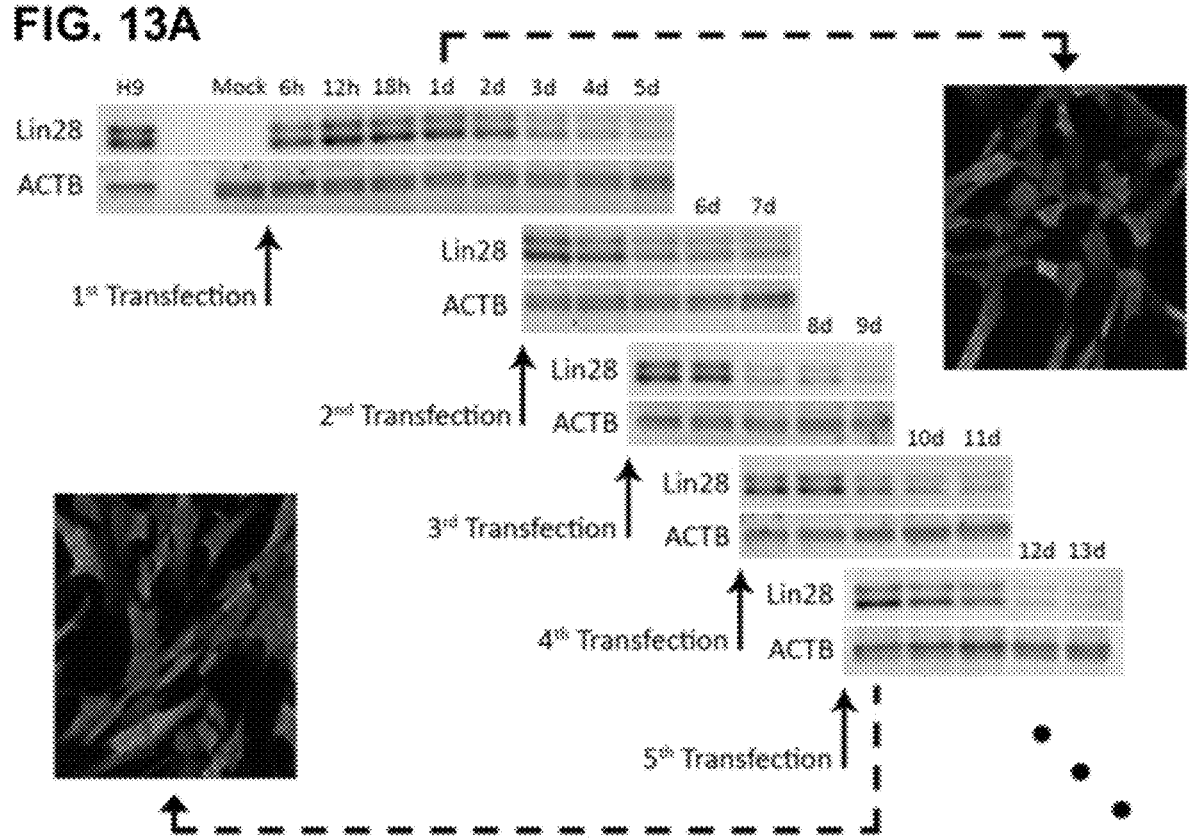
FIG. 13C shows the amount of HMGA2 expression by cells that were transfected with siRNA targeting let7a miRNA and the indicated HUSK ivT-RNA of the invention. HMGA2 expression was measured by RT-PCR, and is shown relative to cells that received no RNA.
FIG. 13D shows the amount of HMGA2 expression by cells were transfected with HUSK ivT-RNA encoding Sox2 (black squares), Lin28 (black circles) or both Sox2 and Lin28 (open triangles), three times at 24-hour intervals. HMGA2 expression was measured by RT-PCR at the indicated times, and is shown relative to mock-transfected cells.
FIG. 13E shows CCD-1109Sk adult dermal fibroblasts cultured with or without 5-aza-dC that were transfected with HUSK ivT-RNA encoding MyoD1. The expression of CDH15 and DES were measured by RT-PCR at the indicated times.
FIG. 13F shows the level of MyoD1 protein measured by western blot in whole-cell lysates that were collected from samples transfected as in (13E).
Figure 13B:
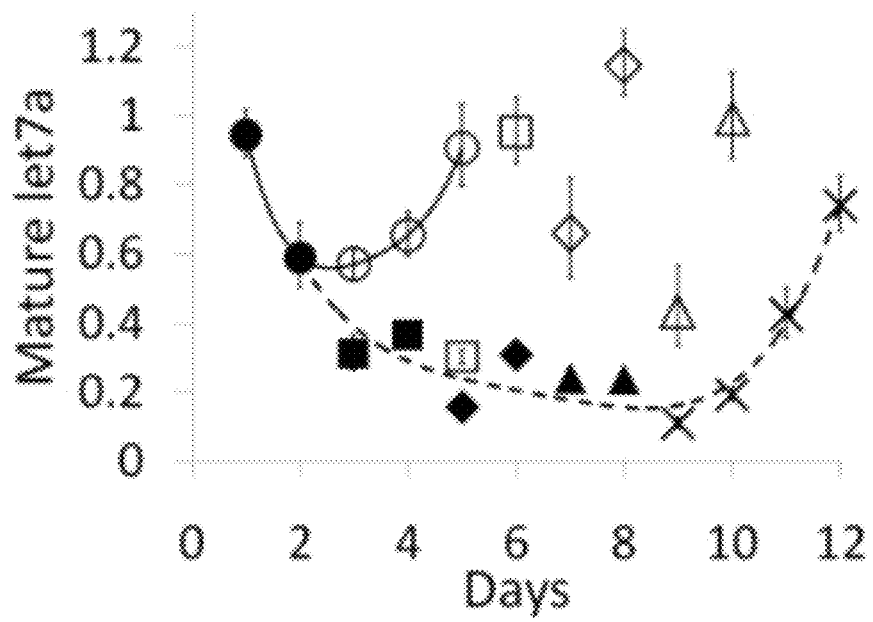

More specifically, FIG. 13A shows the response of MRC-5 fibroblasts that were pre-transfected with a cocktail of siRNAs targeting IFNB1, EIF2AK2, STAT2, and TLR3 before being transfected five times with 0.5 µg Lin28-encoding HUSK ivT RNA and additional siRNA at 48-hour intervals. Cells were lysed at the indicated times, and the amount of Lin28 protein in each sample was assessed by western blot. ACTB was used as a loading control. As can be seen in the figure, a high level of expression of Lin28 protein was sustained in the cells for more than 10 days after the first transfection. FIG. 13B shows the level of mature let7a miRNA relative to the level in mock-transfected cells measured 18 hours after transfection. Smoothed lines are drawn through data points corresponding to cells that were transfected once (solid line) and five times (dashed line). U47 RNA was used as an endogenous control. Error bars show the standard error of replicate samples. These data clearly demonstrate that the encoded protein (in this case Lin28) produced by the cell from the transfected HUSK ivT RNA retains its expected biological functionality, and is highly active. let7a miRNA is a known target of Lin28 protein. As expected, expressing Lin28 protein by ivT-RNA transfection caused a decrease in let7a miRNA.

Figure 13C:
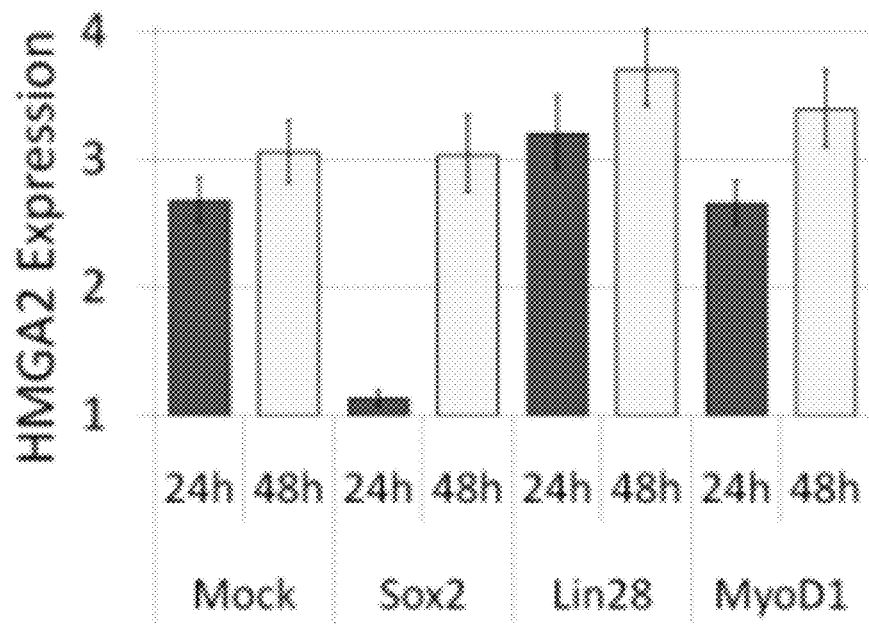
Figure 13D:
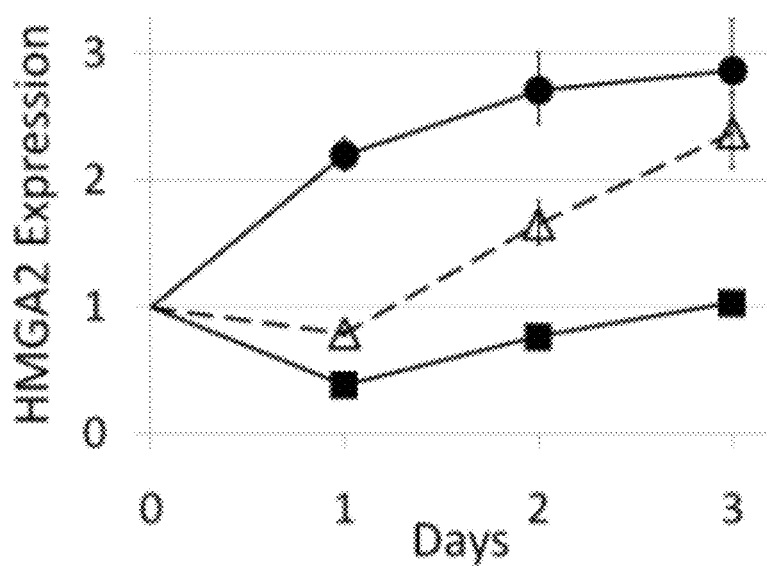

FIG. 13C shows the amount of HMGA2 expression by cells that were transfected with siRNA targeting let7a miRNA and the indicated HUSK ivT RNA of the invention. HMGA2 expression was measured by RT-PCR, and is shown relative to cells that received no RNA. Because Sox2 protein is known to cause the downregulation of HMGA2, the reduction of HMGA2 seen 24 hours after cells were transfected with HUSK ivT RNA encoding Sox2 shows that the Sox2 protein produced from the HUSK ivT RNA retained its biological activity as a transcriptional suppressor, and was highly active. FIG. 13D further shows the amount of HMGA2 expression by cells that were transfected with HUSK ivT RNA encoding Sox2 (black squares), Lin28 (black circles) or both Sox2 and Lin28 (open triangles), three times at 24-hour intervals. HMGA2 expression was measured by RT-PCR at the indicated times, and is shown relative to mock-transfected cells. Because HMGA2 is a known target of let7 miRNA, and let7 miRNA is a known target of Lin28 protein, the increase in HMGA2 expression seen in cells transfected with HUSK ivT RNA encoding Lin28 shows that transfection with HUSK ivT RNA encoding a single protein is sufficient to cause changes in the expression of both direct targets and downstream targets, demonstrating the utility of HUSK ivT-RNA transfection in regulating the gene expression pattern of a cell.

Figure 13E:
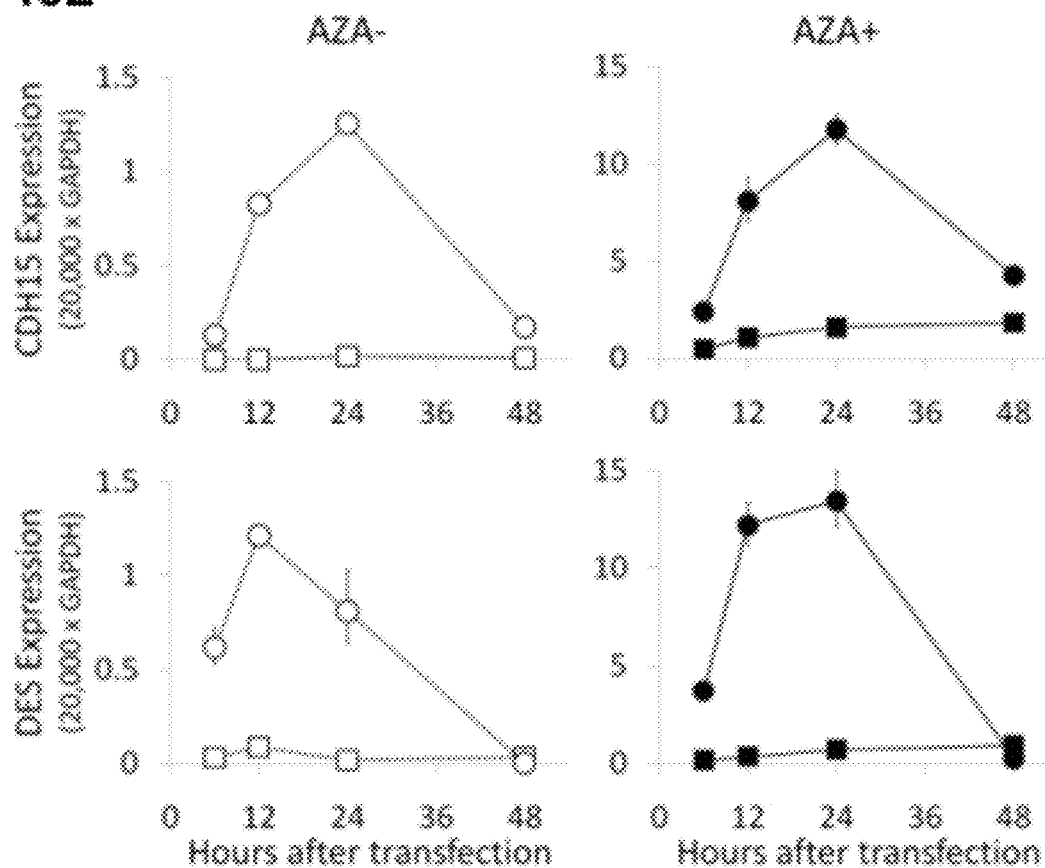
Figure 13F:
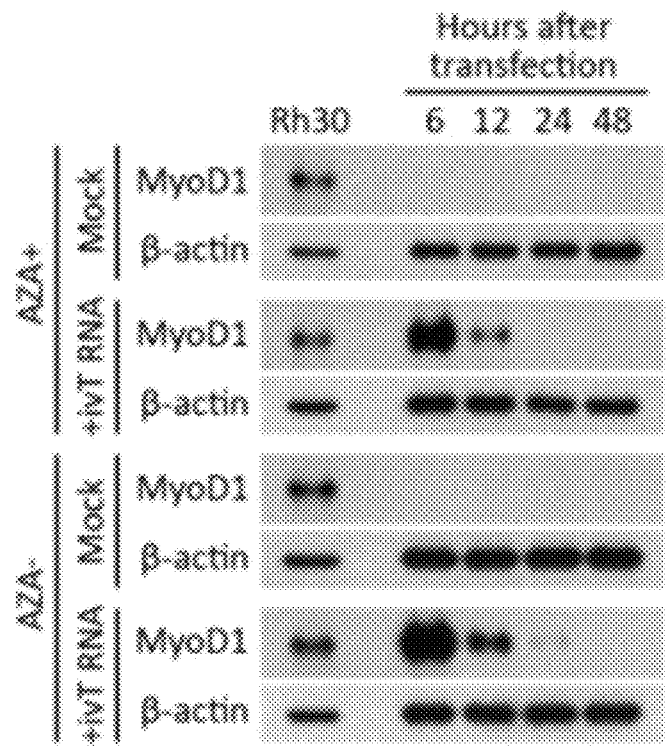

FIG. 13E shows CCD-1109Sk adult dermal fibroblasts cultured with or without 5-aza-dC that were transfected with HUSK ivT RNA encoding MyoD1. The expression of CDH15 and DES were measured by RT-PCR at the indicated times. These results show that cells transfected with HUSK ivT RNA encoding MyoD1 produce MyoD1 protein that maintains its biological activity as a transcriptional activator. In addition, these results demonstrate the utility of combining HUSK ivT-RNA transfection with small molecules such as the demethylating agent 5-aza-dC to enhance the effect of the encoded protein, as the expression of CDH15 and DES (two targets of MyoD1) is enhanced by approximately 10 fold in cells exposed to 5-aza-dC compared to cells not exposed to this chemical. FIG. 13F shows the level of MyoD1 protein measured by western blot in whole-cell lysates that were collected from samples transfected as in (13E). These results show that while the protein encoded by a HUSK ivT RNA may degrade quickly, the effect on downstream targets can persist long after the encoded protein has degraded (note that the expression of CDH15 peaks at 24 hours after transfection, hours after the MyoD1 protein has degraded). This result is important where the goal of transfection is to cause a phenotypic change in the cell, as is discussed below.

Table 4 lists the combinations of known protein factors and transduction methods that to date have been used to convert cells from one type to another. However, all of these cell-type-conversion methods relied on DNA vectors, and as a result the cells are likely unsafe for medical applications. By contrast, extended transient transfection by repeated delivery of HUSK ivT-RNA provides a safe alternative to these DNA-vector-based approaches to achieve phenotypic changes by increasing the expression of certain endogenous proteins known to affect or change cell type. Transfection with HUSK ivT-RNA and immune suppression can be done in vitro or in vivo.

Certain embodiments of the invention are directed to a method for changing the phenotype of a cell by extended transient transfection by repeated delivery of HUSK ivT-RNA encoding particular proteins known to cause a phenotypic change in the cell. For example, adult hippocampal stem cells can be made to differentiate into oligodendrocytes by repeated transfection in combination with suppression of the innate immune response with HUSK ivT-RNA encoding the factor Ascl1. In another example pancreatic exocrine cells can be made to trans-differentiate into insulin-producing beta cells by repeated transfection with suppression of the innate immune response with HUSK ivT-RNA encoding the factors Ngn3, and Pdx1. The new technology described herein lets the user add the desired relative amounts of one or more respective HUSK ivT-RNAs to achieve the desired levels of encoded protein expression to cause the desired phenotypic change. Other examples are listed in the Table 2. Where more than one protein needs to be expressed, there is an option of encoding several proteins in a single transcript or in different transcripts, which may provide finer control of the relative amounts of protein expression.

Other examples wherein a cell is caused to differentiate, transdifferentiate, or dedifferentiate by increasing expression of one or more proteins encoded by ivT RNA using repeated transfection and immune suppression include examples wherein:

1. the cell is an adult hippocampal stem cell, the encoded protein is Ascl1 and the phenotypic change is differentiation of the stem cell to an oligodendrocyte;
2. the cell is a neural stem cell, the cell is transfected with different ivT RNAs each encoding Oct4, Klf4 or c-Myc protein at each transfection step, and the phenotypic change is dedifferentiation of the neural stem cell to a pluripotent stem cell.
3. the cell is a non-insulin-producing pancreatic exocrine cell, the cell is transfected with different ivT RNAs each encoding Ngn3, Pdx1, and Mafa protein at each transfection step, and the phenotypic change is transdifferentiation of the non-insulin-producing pancreatic exocrine cell to an insulin-producing beta islet cell;
4. the cell is a fibroblast or keratinocyte, the cell is transfected with different ivT RNAs each encoding Oct4, Sox2, Klf4, and c-Myc protein at each transfection step, and the phenotypic change is dedifferentiation of the fibroblast to a pluripotent stem cell.
5. the cell is a member selected from the group comprising a fibroblast, chondroblast, smooth muscle cell, and retinal pigmented epithelial cell, the encoded protein is MyoD, and the desired phenotypic change is transdifferentiation of the cell to a myoblast.

6. the cell is a fibroblast, the encoded proteins are PU.1, and C/EBPα/β, and the desired phenotypic change is transdifferentiation of the fibroblast to a macrophage.

In other embodiments, the desired phenotypic change is proliferation, attachment, migration, or growth of a process such as an axon.

to increasing cell proliferation of a cell transfected with a nucleic acid by suppressing one or more of the following: CDKN1A, CDKN2A, RB1, and TP53. In other embodiments the methods for changing a cell's phenotype further include contacting the cell with histone deacetylase inhibitors (valproic acid or trichostatin A), a demethylating agent

TABLE 4

| Conversion Type | Factors | Transduction Method | Starting Cell Type | Target Cell Type | References |
|---|---|---|---|---|---|
| Differentiation | Ascl1 | retrovirus | adult hippocampal stem cell could be xenografts | oligodendrocyte | 67 |
| Transdifferentiation | MyoD | retrovirus | fibroblast, chondroblast, smooth muscle cell, retinal pigmented epithelial cell | myoblast | 68 |
| | PU.1, C/EBPα/β | retrovirus | fibroblast | macrophage | 69 |
| | Ngn3, Pdx1, Mafa | adenovirus | pancreatic exocrine cell | β-cell | 70 |
| Dedifferentiation | Oct4 | retrovirus | neural stem cell Invasive, brain sample | pluripotent stem cell | 71 |
| | Oct4, (Klf4 or c-Myc) | retrovirus | neural stem cell | pluripotent stem cell | 72 |
| | Oct4, Sox2, Klf4, c-Myc | retrovirus | Fibroblast Customized for each patient | pluripotent stem cell | 73, 74, 75, 76 |

Both Jessberger, et al. and Zhou et al. describe cell-type-conversion experiments conducted in vivo. The HUSK ivT-RNA transcripts of the present invention can be used in vivo and would not have the risk of causing permanent genetic alterations of the cell.

In addition to expressing defined factors by HUSK ivT-RNA transfection, establishing a new gene-expression program in a cell can be enhanced by inhibiting the expression of certain factors that are expressed by the current cell type, but not the target cell type. For example, the histone deacetylase inhibitors valproic acid and trichostatin A have been shown to increase induction of pluripotent stem cells, i.e. their dedifferentiation into a desired target cell type. (see Huangfu, et al. "Induction of pluripotent stem cells by defined factors is greatly improved by small-molecule compounds." Nat. Biotech. 2008). The demethylating agent 5-aza-2'-deoxycytidine has been shown to enhance dedifferentiation of a somatic cell into a pluripotent stem cell. (See Mikkelsen, et al. "Dissecting direct reprogramming through integrative genomic analysis." Nature. 2008), and the G9a histone methyltransferase inhibitor BIX-01294 has been shown to facilitate the dedifferentiation of neural stem cells to pluripotent stem cells. (see Shi, et al. "A Combined Chemical and Genetic Approach for the Generation of Induced Pluripotent Stem Cells." Cell Stem Cell. Vol. 2. 2008.) In addition, the targets of these small molecules and other targets that inhibit the desired phenotypic change can be directly inhibited by the use of siRNA and antisense oligonucleotides. We have shown for example that siRNA targeting the G9a histone methyltransferase can be used to significantly reduce the expression of this protein alone or in combination with an siRNA cocktail designed to suppress the innate immune response and ivT-RNA transfection.

As described above, active proliferation is important to minimize the cytotoxicity associated with frequent transfections. To this end, reducing the expression of several genes known to suppress proliferation (including CDKN1A, CDKN2A, RB1, and TP53) using antisense oligonucleotides or siRNA will also improve expression of ivT-RNA encoded proteins and cell viability. Certain embodiments are directed such as 5-aza-2'-deoxycytidine, or the G9a histone methyltransferase inhibitor BIX-01294 to optimize the desired phenotypic change.

The future of medicine will be characterized by therapies based on techniques for controlling cell type. Replacing cells, tissues, and organs lost to disease or injury requires methods of generating new tissue-specific cells in vitro for implantation into damaged areas of the body. Transfecting cells with DNA, RNA or proteins provides a means not only for generating these tissue-specific cells by directing the differentiation of stem cells in vitro, but also for unraveling the molecular pathways that control cell-type specification and maintenance by selectively over expressing the various proteins involved in these processes. While transforming cells by DNA transfection is a simple method of achieving stable gene expression, the safety issues that arise from altering cell type by genetic modification will likely limit the use of this technique in regenerative-medicine applications. Controlling cell type by transient transfection with HUSK ivT-RNA offers an improvement over earlier methods as these molecules, once they have performed their function, are metabolized by the cell, leaving it genetically indistinguishable from the donor. Transfection with RNA in particular offers two critical advantages: 1. RNA can be easily synthesized in vitro for any protein of reasonable length and a known sequence, and 2. Many copies of a protein can be synthesized by the cell from each RNA molecule, minimizing the amount of material that must be delivered, thus minimizing cellular stress.

Protein Variants.

While the invention will be typically drawn to using ivT-RNA made from mRNA encoding the endogenous proteins of interest, particularly those that cause a desired phenotypic change, it may be advantageous to use ivT-RNA that is translated into biologically-active protein variants of these endogenous protein that provide useful and novel characteristics. Certain protein variants or encoded proteins include fused proteins, for example, that could be engineered for increased stability or to include a fluorescent tag such as green fluorescent protein (GFP) to enable the real-time visualization of the encoded protein by fluorescence microscopy, among other possible characteristics. Thus the ivT-RNA can encode protein variants that are substantially homologous to the respective endogenous proteins. For the purpose of this invention, analogs of a protein include substantially homologous proteins that are naturally occurring and retain the desired biological activity.

As used herein, two proteins (or a region of the proteins) are substantially homologous when the amino acid sequences are at least about 70-75%, typically at least about 80-85%, and most typically at least about 90-95%, 97%, 98% or 99% or more homologous. A substantially homologous amino acid sequence, will be encoded by a nucleic acid sequence hybridizing to the corresponding nucleic acid sequence, or portion thereof, under stringent conditions as more fully described below.

The ivT-RNA can include a coding sequence for the endogenous protein that has conservative amino acid substitutions such as Aromatic Phenylalanine Tryptophan Tyrosine Hydrophobic Leucine Isoleucine Valine Polar Glutamine Asparagine Basic Arginine Lysine Histidine Acidic Aspartic Acid Glutamic Acid Small Alanine Serine Threonine Methionine Glycine A variant polypeptide can differ in amino acid sequence by one or more substitutions, deletions, insertions, inversions, fusions, and truncations or a combination of any of these. Variant polypeptides can be fully functional or can lack function in one or more activities.

Fully functional variants typically contain only conservative variations or variations in non-critical residues or in non-critical regions. Functional variants can also contain substitution of similar amino acids, which results in no change or an insignificant change in function. Alternatively, such substitutions may positively or negatively affect function to some degree.

Substantial homology can be to the entire mRNA encoding the endogenous protein of interest or to mRNA encoding a biologically-active fragment or variant thereof. Accordingly, a fragment can comprise any length that retains one or more of the biological activities of the protein. Fragments can be discrete (not fused to other amino acids or polypeptides) or can be within a larger polypeptide.

Antisense Nucleic Acids

Other embodiments of the present invention are directed to the use of antisense nucleic acids (either DNA or RNA) or small inhibitory RNA (siRNA) to reduce or inhibit expression of certain proteins associated with the innate immune response, including TP53, TLR3, TLR7, RARRES3, IFNA1, IFNA2, IFNA4, IFNA5, IFNA6, IFNA7, IFNA8, IFNA10, IFNA13, IFNA14, IFNA16, IFNA17, IFNA21, IFNK, IFNB1, IL6, TICAM1, TICAM2, MAVS, STAT1, STAT2, EIF2AK2, IRF3, TBK1, CDKN1A, CDKN2A, RNASEL, IFNAR1, IFNAR2, OAS1, OAS2, OAS3, OASL, RB1, ISG15, ISG20, IFIT1, IFIT2, IFIT3, and IFIT5, or a biologically-active fragment or variant or analog thereof, hereafter "immune suppression proteins." The mRNA and gene sequences encoding the targeted immune suppression proteins are set forth herein by accession numbers. Based on these known sequences, antisense DNA or RNA that hybridize sufficiently to the respective gene or mRNA encoding the immune suppression proteins to turn off expression can be readily designed and engineered using methods known in the art.

Antisense oligonucleotides have been employed as therapeutic moieties in the treatment of disease states in animals and man. Antisense oligonucleotide drugs, including ribozymes, have been safely and effectively administered to humans and numerous clinical trials are presently underway.

It is thus established that oligonucleotides can be useful therapeutic modalities that can be configured to be useful in treatment regimes for treatment of cells, tissues and animals, especially humans. See for example Agrawal, S, and Zhao, Q. (1998) Curr. Opi. Chemical Biol. Vol. 2, 519-528; Agrawal, S. and Zhang, R. (1997) CIBA Found. Symp. Vol. 209, 60-78; and Zhao, Q, et al., (1998), Antisense Nucleic Acid Drug Dev. Vol 8, 451-458; the entire contents of which are hereby incorporated by reference as if fully set forth herein. Anderson, K. O., et al., (1996) Antimicrobial Agents Chemother. Vol. 40, 2004-2011, and U.S. Pat. No. 6,828,151 by Borchers, et al.

Methods of making antisense-nucleic acids are well known in the art. As used herein, the terms "target nucleic acid" encompass nucleic acids encoding the immune suppression proteins (including pre-mRNA and mRNA) and to the gene encoding the proteins, and also cDNA derived from such RNA. The specific hybridization of a nucleic acid oligomer compound with its target nucleic acid interferes with the normal function of the target nucleic acid, thereby reducing translation of the ivT-RNA, for example. This modulation of function of a target nucleic acid by compounds which specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, and catalytic activity which may be engaged in or facilitated by the RNA. The overall effect of such interference with target nucleic acid function is modulation of the expression of the respective protein. In the context of the present invention, "modulation" means reducing or inhibiting in the expression of the gene or mRNA for the immune suppression proteins. In one embodiment the antisense oligonucleotide is cDNA.

The targeting process includes determining the site or sites within the target gene or mRNA encoding the immune suppression proteins for the antisense interaction to occur such that the desired inhibitory effect is achieved. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene. However routine experimentation will determine the optimal sequence of the antisense or siRNA.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, antisense nucleic acids are chosen which are sufficiently complementary to the target, i.e., to hybridize with sufficient specificity to the target, to give the desired effect of inhibiting gene expression and transcription or mRNA translation.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of a nucleic acid is capable of hydrogen bonding with a nucleotide at the same position of a DNA or RNA molecule, then the nucleic acid and the DNA or RNA are considered to be complementary to each other at that position. The nucleic acid and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the nucleic acid and the DNA or RNA target. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays or cell culturing are performed.

Various conditions of stringency can be used for hybridization as is described below. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1 6.3.6, which is incorporated by reference. Aqueous and nonaqueous methods are described in that reference and either can be used. Specific hybridization conditions referred to herein are as follows: 1) low stringency hybridization conditions in 6.times.sodium chloride/sodium citrate (SSC) at about 45° C., followed by two washes in 0.2.times.SSC, 0.1% SDS at least at 50.degree C. (the temperature of the washes can be increased to 55° C. for low stringency conditions); 2) medium stringency hybridization conditions in 6.times.SSC at about 45° C., followed by one or more washes in 0.2.times.SSC, 0.1% SDS at 60° C.; 3) high stringency hybridization conditions in 6.times.SSC at about 45° C., followed by one or more washes in 0.2.times.SSC, 0.1% SDS at 65° C.; and preferably 4) very high stringency hybridization conditions are 0.5M sodium phosphate, 7% SDS at 65° C., followed by one or more washes at 0.2.times.SSC, 1% SDS at 65° C. Very high stringency conditions (4) are the preferred conditions and the ones that should be used unless otherwise specified.

Nucleic acids in the context of this invention include "oligonucleotides," which refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. DNA/RNA chimeras are also included.

While antisense nucleic acids are a preferred form of antisense compound, the present invention comprehends other oligomeric antisense compounds, including but not limited to oligonucleotide mimetics. The antisense compounds in accordance with this invention preferably comprise from about 8 to about 50 nucleobases (i.e. from about 8 to about 50 linked nucleosides). Particularly preferred antisense compounds are antisense nucleic acids comprising from about 12 to about 30 nucleobases. Antisense compounds include ribozymes, external guide sequence (EGS) nucleic acids (oligozymes), and other short catalytic RNAs or catalytic nucleic acids which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure; however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides. Preferred modified oligonucleotide backbones include, for example, phosphorothioates, chiral phosphorothioates, phosphorodithioates, phosphotriesters, aminoalkyl-phosphotriesters, methyl and other alkyl phosphonates including 3-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference. Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene(methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$OCH$_3$, O($CH_2$).sub.nNH$_2$, $O(CH_2)_nCH_3$, $O(CH_2)_nONH_2$, and $O(CH_2)_nON[(CH_2)$.sub. $nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy(2'—O—$CH_2CH_2OCH_3$, also known as 2'—O—(2-methoxyethyl) or 2'-MOE) (Martin et al., Helv. Chim. Acta, 1995, 78, 486-504) i.e., an alkoxy-alkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylamino-ethoxyethoxy (also known in the art as 2'-O-dimethylamino-ethoxyethyl or 2'-DMAEOE), i.e., 2'—O—$CH_2$—O—$CH_2$—$N(CH_2)_2$, also described in examples hereinbelow.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy(2'—O—$CH_3$), 2'-aminopropoxy (2'—$OCH_2CH_2CH_2NH_2$), 2'-allyl (2'—$CH_2$—CH=$CH_2$), 2'-O-allyl (2'-O—$CH_2$—CH=$CH_2$) and 2'-fluoro(2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine. (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C.ident.O—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deaza-guanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, poly ethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et. al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid; e.g., di hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyl-oxycholesterol moiety (Crooke et al., J. Pharmacol. Exp. Ther., 1996, 277, 923-937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above, or the may be made of DNA and RNA (hence a DNA/RNA chimera). Such compounds have also been referred to in the art as hybrids or gapmers. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The compounds of the invention may also be admixed, encapsulated, conjugated or otherwise associated with other molecules, molecule structures or mixtures of compounds, as for; example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare nucleic acids such as the phosphorothioates and alkylated derivatives. The antisense compounds of the invention are synthesized in vitro and do not include antisense compositions of biological origin, or genetic vector constructs designed to direct the in vivo synthesis of antisense molecules.

Small Inhibitory RNA

It has been shown that when short (18-30 bp) RNA duplexes are introduced into mammalian cells in culture, sequence-specific inhibition of target mRNA can be realized without inducing an interferon response. Certain of these short dsRNAs, referred to as small inhibitory RNAs ("siRNAs"), can act catalytically at sub-molar concentrations to cleave greater than 95% of the target mRNA in the cell. A description of the mechanisms for siRNA activity, as well as some of its applications are described in Provost et al., Ribonuclease Activity and RNA Binding of Recombinant Human Dicer, E.M.B.O. J., 2002 Nov. 1; 21(21): 5864-5874; Tabara et al., The dsRNA Binding Protein RDE-4 Interacts with RDE-1, DCR-1 and a DexH—box Helicase to Direct RNAi in C. elegans, Cell 2002, Jun. 28; 109(7):861-71; Ketting et al., Dicer Functions in RNA Interference and in Synthesis of Small RNA Involved in Developmental Timing in C. elegans; Martinez et al, Single-Stranded Antisense siRNAs Guide Target RNA Cleavage in RNAi, Cell 2002, Sep. 6; 110(5):563; Hutvagner & Zamore, A microRNA in a multiple-turnover RNAi enzyme complex, Science 2002, 297:2056.

US Patent Application 20040023390 (the entire contents of which are hereby incorporated by reference as if fully set forth herein) teaches that double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shut-down of protein synthesis and even cell death through apoptosis. Recent work shows that RNA fragments are the sequence-specific mediators of RNAi (Elbashir et al., 2001). Interference of gene expression by these small inhibitory RNA (siRNA) is now recognized as a naturally occurring strategy for silencing genes in C. elegans, Drosophila, plants, and in mouse embryonic stem cells, oocytes and early embryos (Cogoni et al., 1994; Baulcombe, 1996; Kennerdell, 1998; Timmons, 1998; Waterhouse et al., 1998; Wianny and Zernicka-Goetz, 2000; Yang et al., 2001; Svoboda et al., 2000).

As used herein RNAi is the process of RNA interference. A typical mRNA produces approximately 5,000 copies of a protein. RNAi is a process that interferes with or significantly reduces the number of protein copies made by an mRNA of the targeted protein, preferably an immune suppression protein. For example, a double-stranded short interfering RNA (siRNA) molecule is engineered to complement and match the protein-encoding nucleotide sequence of the target mRNA to be interfered with, or a biologically-active fragment of the protein. Following intracellular delivery, the siRNA molecule associates with an RNA-induced silencing complex (RISC). The siRNA-associated RISC binds the target mRNA through a base-pairing interaction and degrades it. The RISC remains capable of degrading additional copies of the targeted mRNA. Other forms of RNA can be used such as short hairpin RNA and longer RNA molecules. Longer molecules cause cell death, for example by instigating apoptosis and inducing an interferon response. Cell death was the major hurdle to achieving RNAi in mammals because dsRNAs longer than 30 nucleotides activated defense mechanisms that resulted in non-specific degradation of RNA transcripts and a general shutdown of the host cell. Using from about 20 to about 29 nucleotide siRNAs to mediate gene-specific suppression in mammalian cells has apparently overcome this obstacle. These siRNAs are long enough to cause gene suppression but not of a length that induces an interferon response.

Antibodies

"Antibody" or "antibodies" include intact molecules as well as fragments thereof that are capable of specifically binding to an epitope of a protein of interest. As used herein, "specific binding" refers to the property of the antibody, to: (1) to bind to a target protein, with an affinity of at least 1×107 M−1, and (2) preferentially at least two-fold, 50-fold, 100-fold, 1000-fold, or more greater than its affinity for binding to a non-specific antigen (e.g., BSA, casein). In a preferred embodiment, the interaction, e.g., binding, between an antibody occurs with high affinity (e.g., affinity constant of at least 107 M 1, preferably, between 108 M−1 and 1010, or about 109 M−1) and specificity.

The term "epitope" refers to an antigenic determinant on an antigen to which an antibody binds. Epitopes usually consist of chemically active surface groupings of molecules such as amino acids or sugar side chains, and typically have specific three-dimensional structural characteristics, as well as specific charge characteristics. Epitopes generally have at least five contiguous amino acids.

The terms "antibody" and "antibodies" include polyclonal antibodies, monoclonal antibodies, humanized or chimeric antibodies, single chain Fv antibody fragments, Fab fragments, and F(ab)$_2$ fragments. Polyclonal antibodies are heterogeneous populations of antibody molecules that are specific for a particular antigen, while monoclonal antibodies are homogeneous populations of antibodies to a particular epitope contained within an antigen. Monoclonal antibodies are particularly useful.

Antibody fragments that have specific binding affinity for the polypeptide of interest can be generated by known techniques. Such antibody fragments include, but are not limited to, F(ab')$_2$ fragments that can be produced by pepsin digestion of an antibody molecule, and Fab fragments that can be generated by deducing the disulfide bridges of F(ab') 2 fragments. Alternatively, Fab expression libraries can be constructed. See, for example, Huse et al. (1989) Science 246:1275-1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778.

Once produced, antibodies or fragments thereof can be tested for recognition of the target polypeptide by standard immunoassay methods including, for example, enzyme-linked immunosorbent assay (ELISA) or radioimmunoassay assay (RIA). See, Short Protocols in Molecular Biology eds. Ausubel et al., Green Publishing Associates and John Wiley & Sons (1992). Suitable antibodies typically have equal binding affinities for recombinant and native proteins.

The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition.

The term "recombinant" antibody, as used herein, refers to antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created or isolated by any other means that involves splicing of human immunoglobulin gene sequences to other DNA sequences. Such recombinant antibodies include humanized, CDR grafted, chimeric, deimmunized, in vitro generated (e.g., by phage display)

antibodies, and may optionally include constant regions derived from human germline immunoglobulin sequences.

Human monoclonal antibodies (mAbs) directed against human proteins can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856 859; Green, L. L. et al. 1994 Nature Genet. 7:13 21; Morrison, S. L. et al. 1994 Proc. Natl. Acad. Sci. USA 81:6851 6855; Bruggeman et al. 1993 Year Immunol 7:33 40; Tuaillon et al. 1993 PNAS 90:3720 3724; Bruggeman et al. 1991 Eur J Immunol 21:1323 1326).

Antibodies or fragments thereof useful in the present invention may also be recombinant antibodies produced by host cells transformed with DNA encoding immunoglobulin light and heavy chains of a desired antibody. Recombinant antibodies may be produced by known genetic engineering techniques. For example, recombinant antibodies may be produced by cloning a nucleotide sequence, e.g., a cDNA or genomic DNA sequence, encoding the immunoglobulin light and heavy chains of the desired antibody from a hybridoma cell that produces an antibody useful in this invention. The nucleotide sequence encoding those polypeptides is then inserted into expression vectors so that both genes are operatively linked to their own transcriptional and translational expression control sequences. The expression vector and expression control sequences are chosen to be compatible with the expression host cell used. Typically, both genes are inserted into the same expression vector. Prokaryotic or eukaryotic host cells may be used.

Expression in eukaryotic host cells is preferred because such cells are more likely than prokaryotic cells to assemble and secrete a properly folded and immunologically active antibody. However, any antibody produced that is inactive due to improper folding may be renaturable according to well known methods (Kim and Baldwin, "Specific Intermediates in the Folding Reactions of Small Proteins and the Mechanism of Protein Folding," Ann. Rev. Biochem. 51, pp. 459 89 (1982)). It is possible that the host cells will produce portions of intact antibodies, such as light chain dimers or heavy chain dimers, which also are antibody homologs according to the present invention.

Chimeric antibodies, including chimeric immunoglobulin chains, can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science 240:1041 1043); Liu et al. (1987) PNAS 84:3439 3443; Liu et al., 1987, J. Immunol. 139:3521 3526; Sun et al. (1987) PNAS 84:214 218; Nishimura et al., 1987, Canc. Res. 47:999 1005; Wood et al. (1985) Nature 314:446 449; and Shaw et al., 1988, J. Natl Cancer Inst. 80:1553 1559).

An antibody or an immunoglobulin chain can be humanized by methods known in the art. Once the murine antibodies are obtained, the variable regions can be sequenced. The location of the CDRs and framework residues can be determined (see, Kabat, E. A., et al. (1991) Sequences of Proteins of Immunological Interest, Fifth Edition, U.S. Department of Health and Human Services, NIH Publication No. 91 3242, and Chothia, C. et al. (1987) J. Mol. Biol. 196:901 917, which are incorporated herein by reference). The light and heavy chain variable regions can, optionally, be ligated to corresponding constant regions The invention is illustrated herein by the experiments described above and by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

EXAMPLES

Example 1

Materials and Methods

Mouse embryonic fibroblast (MEF) derivation. Mouse embryonic fibroblasts were derived from E13 CF-1 mice (Charles River Laboratories). Animals were administered 250 mg/kg Avertin® (2,2,2-tribromoethanol) by interperitoneal injection, and euthanized by cervical dislocation. Uterine horns from each animal were removed from the peritoneum, placed in a 10 cm Petri dish and rinsed with PBS. Embryonic sacs were cut, and embryos removed, rinsed with PBS, and counted. Visceral tissue was separated and discarded, and embryos were rinsed again with PBS. Remaining tissue was minced with dissecting scissors, 2 mL trypsin was added, and tissue was further minced until no large pieces remained. An additional 5 mL trypsin was added, and dishes were placed in a 37 C, 5% $CO_2$ incubator for 20-30 minutes. MEF Media media (see Appendix C) supplemented with penicillin and streptomycin was added, and cells were cultured in T75 flasks (approximately 3 embryos per flask). The following day, cells from a total of 6 mice were pooled into two groups, MEF1 and MEF2, and were frozen in MEF Media supplemented with 10% DMSO and stored in liquid nitrogen. A sample from each group was tested for mycoplasmal contamination (test M-250, Bionique® Testing, Inc.). Both samples tested negative for mycoplasmal contamination by both DNA fluorochrome staining and live-culture methods.

Fibroblast culture. Primary human fibroblasts from normal fetal lung tissue (MRC-5) were obtained from the ATCC and were cultured according to their recommendations.

Denaturing formaldehyde-agarose gel electrophoresis. Transcripts were analyzed both before and after poly(A) tailing by denaturing formaldehyde-agarose gel electrophoresis to ensure that they were the expected size and to measure the length of the poly(A) tail. Three volumes of Formaldehyde Load Dye were added to each sample, and the samples were denatured at 70 C for 15 min, then loaded into the wells of a 1.5% formaldehyde-agarose gel (Northern-Max® Kit, Ambion). An RNA ladder (Millennium Markers™, Ambion) was used for size comparison.

Lipid-mediated transfection. ivT-RNA was delivered to MRC-5 fibroblasts by lipid-mediated transfection (TransIT®, Mirus) following the manufacturer's instructions.

Electroporation. Cells were trypsinized, washed once in Opti-MEM® (Invitrogen), and resuspended in a total volume of 50 µL Opti-MEM® in a standard electroporation cuvette with a 2 mm gap. A 150 µF capacitor charged to between 110V and 145V was discharged into the cuvette to electroporate the cells. Warm media was added, and the cells were plated in 10 cm dishes or multi-well plates.

Quantitative RT-PCR. Primers and molecular-beacon probes were designed to detect HUSK Transcripts A-F. Amplicons were designed to span the stop codon to prevent the coamplification of endogenous transcripts. Standard curves were generated to assess the efficiency of each reaction. TaqMan® Gene Expression Assays (Applied Biosystems, Table A.1) were used to measure levels of endogenous mRNA. RNA was extracted from cells and purified (RNeasy mini kit, Qiagen) before RT-PCR (iScript™ One-Step RT-PCR Kit, Bio-Rad). The RT-PCR protocol includes a 50° C., 10 min reverse transcription step, followed by an initial denaturation step of 95° C. for 5 min, and 45 cycles of 95° C. for 15 sec and 55° C. for 30 sec.

siRNA-mediated knockdown. Cells were electroporated (see protocol above) in Opti-MEM® containing siRNA (Applied Biosystems, Table A.1) at various concentrations. Table A.1 lists several siRNA molecules that were purchased through commercial vendors. Mixtures of these siRNAs that suppress innate immune response proteins come within the scope of this invention.

Immunocytochemistry. Cells were rinsed in PBS and fixed for 10 minutes in 4% paraformaldehyde. Cells were then permeabilized in 0.1% Triton X-100 and blocked for 30 min in 2% skim milk. After blocking, cells were incubated with primary antibodies overnight at 4 C, washed three times in 0.05% Tween® 20, and incubated with FITC- and CY3-conjugated secondary antibodies for 1 hour at room temperature. Cells were washed three times in 0.05% Tween® 20, incubated with Hoechst 33342 for one minute, rinsed, mounted in 50% glycerol in PBS, and imaged by fluorescence microscopy.

Polyacrylamide gel electrophoresis (PAGE) and western blot. Whole-cell lysates (Qproteome Mammalian Protein Prep Kit, Qiagen) were separated on a 12% polyacrylamide gel (ProSieve® 50, Lonza) under reducing, denaturing conditions. Proteins were transferred onto a PVDF membrane (Immobilon™-FL, Millipore) in CAPS buffer, pH 11. The membrane was blocked in 3% BSA in TBST and probed with appropriate antibodies. Quantum-dot-conjugated secondary antibodies Qdot® (Invitrogen) were used for multiplexed probing. β-actin (Abcam 8226) was used as a loading control.

Example 2

A. ivT-template Assembly and In Vitro Transcription

Recombinant T7 bacteriophage RNA polymerase is widely used for in vitro transcription from a DNA template containing the minimal T7 promoter sequence, TAATAC-GACTCACTATAGGG (SEQ ID NO: 22), with the last three bases (GGG) encoding the first three nucleotides of the transcript (also GGG). Several commercial in vitro-transcription kits are available that use this enzyme together with buffers and additives designed to produce high yields of full-length transcripts. Linearized plasmids, PCR products, and single-stranded oligonucleotides can be used as T7 RNA-polymerase templates, although the T7 promoter must be double-stranded. For this study, to simplify the template synthesis procedure while minimizing sequence errors, the in vitro-transcription template was designed as a blunt-ended PCR product to be produced by a high-fidelity DNA polymerase from reverse-transcribed poly(A)+ mRNA. Choosing a PCR product facilitates the production of large quantities of template without the need for bacterial cloning, and eliminates the linearization step required when using a plasmid template. Amplifying reverse-transcribed poly(A)+ mRNA ensures that the sequences of the ivT-template components will match those of mature endogenous transcripts.

To produce dsDNA templates for T7 in vitro-transcription reactions, a sticky-end ligation was designed to combine the HBB UTRs with an arbitrary CDS using the two restriction endonucleases, NheI (recognition site: G/CTAG\C) and AgeI (recognition site: A/CCGG\T), which are active in the same buffer, allowing a combined digestion. Primers containing the T7 promoter, a Kozak sequence with strong consensus, and the restriction enzyme recognition sites were designed to facilitate the incorporation of these elements into the ivT-template components during PCR. Five adenosine residues were included on the 5' ends of the HBB 5'-UTR reverse primer and the HBB 3'-UTR forward primer to facilitate digestion. The HBB UTR primer sequences are shown below with the T7 promoter and restriction-enzyme recognition sites underlined.

A list of restriction enzymes for use in the present invention include: AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BseRI, BseYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdeI, DpnI, DpnII, DraI, DraIII, DrdI, EaeI, EagI, EarI, EciI, EcoNI, EcoO109I, EcoP15I, EcoRI, EcoRV, FatI, FauI, Fnu4HI, FokI, FseI, FspI, HaeII, HaeIII, HgaI, HhaI, HincII, HindIII, HinfI, HinP1I, HpaI, HpaII, HphI, Hpy166II, Hpy188I, Hpy188III, Hpy99I, HpyAV, HpyCH4III, HpyCH4IV, HpyCH4V, KasI, KpnI, MboI, MboII, MfeI, MluI, MlyI, MmeI, MnlI, MscI, MseI, MslI, MspA1I, MspI, MwoI, NaeI, NarI, NciI, NcoI, NdeI, NgoMIV, NheI, NlaIII, NlaIV, NmeAIII, NotI, NruI, NsiI, NspI, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, TaqaI, TfiI, TliI, TseI, Tsp45I, Tsp509I, TspMI, TspRI, Tth111I, XbaI, XcmI, XhoI, XmaI, XmnI, and ZraI.

A diagram of the basic assembled HBB-UTR-stabilized Kozak+ (HUSK) in vitro-transcription template is shown below.

```
HBB 5'-UTR Forward Primer:
                                    SEQ ID NO: 23
TAATACGACTCACTATAGGGACATTTGCTTCTGACACAACTGTG HBB 5'-UTR Reverse Primer:
                                    SEQ ID NO: 16
AAAAAGCTAGCTGTTTGAGGTTGCTAGTGAACACAGTTGTG
Product Length: 75 bp HBB 3'-UTR Forward Primer:
                  SEQ ID NO: 17
AAAAAACCGGTGCTCGCTTTCTTGCTGTC HBB 3'-UTR Reverse Primer:
                                    SEQ ID NO: 18
GCAATGAAAATAAATGTTTTTTATTAGGCAGAATCCAGATG
Product Length: 143 bp (the drawing below discloses SEQ ID NOS: 19-21, respectively, in order
of appearance).

T7 Promoter      ↓            ▼ NheI    CDS    ▼       HBB 3'-UTR
TAATACGACTCACTATAGGGACATTT•••CAAACAGCTAGCCACCATG•••ACCGGTGCTCGC•••CATTGC
                     HBB 5'-UTR         ▲ Kozak      AgeI▲
```

B. Coding Sequences and Untranslated Regions for the HUSK ivT-RNA Templates

Human embryonic stem (hES) cell culture. H9 human embryonic stem cells were obtained from the National Stem Cell Bank at passage 24, and were cultured on irradiated mouse embryonic fibroblasts (MEFs) derived from E13 CF-1 mice (Charles River Laboratories) as described[1] (see Methods). The hES cells grew as large colonies of compact cells with little cytoplasm. Cells grown on MEFs were stained with antibodies against the pluripotency markers Oct4 and Nanog. hES-cell colonies contained many brightly stained cells, while the MEFs were not stained. After several passages, some cells were plated on dishes coated with BME basement membrane matrix (Trevigen), and were cultured in media conditioned for 24 hours on irradiated MEFs and supplemented with 4 ng/mL bFGF (Invitrogen) and 10 μM of the ROCK inhibitor Y-27632 (Cayman Chemical)[50]. Cells grown in conditioned media with Y-27632 exhibited very low levels of the spontaneous differentiation observed in cells grown on MEFs or in conditioned media without Y-27632.

Total RNA was extracted from H9 hES cells cultured in conditioned media on BME-coated plates using RNeasy mini kits (Qiagen) with an on-column DNAseI digestion. Poly(A)+ mRNA was enriched using poly(dT) latex beads Oligotex Qiagen), quantitated (Quant-iT™, Invitrogen) and stored at 4 C in 5 mM Tris-HCl, pH 7.5. Poly(A)+ mRNA Transcripts of interest and β-globin were reverse transcribed in separate reactions using an RNase H— reverse transcriptase (MonsterScript™, Epicentre®) and primers designed to anneal to the 3' ends of the HBB 3'-UTR and the CDSs of the seven genes selected for this study (Table B.1). Template components were amplified using a high-fidelity polymerase (Phusion™ Hot Start, NEB) and ligated with E. coli DNA ligase (NEB). Ligation products were amplified and gel purified (Gel Extraction Kit, Qiagen) in preparation for in vitro transcription.

The HBB 3'-UTRs and the seven CDSs were then amplified using a high-fidelity polymerase (Phusion™ Hot-Start, NEB) to minimize sequence errors (Tables B.2-B.4). The HBB 5'-UTR primers span the entire PCR product, eliminating the need for a cDNA template in the HBB 5'-UTR amplification reaction. The primers were designed to attach the T7 promoter sequence to the 5' end of the HBB 5'-UTR and restriction-enzyme recognition sequences to the 3' end of the HBB 5'-UTR, the 5' end of the HBB 3'-UTR, and both ends of the CDSs. The reaction products were separated on a 1.5% (CDSs) or a 3% (HBB UTRs) agarose gel, the appropriate bands were excised, and the DNA extracted (Gel Extraction Kit, Qiagen).

The PCR products were digested using NheI and Age I restriction enzymes (Table B.5), purified (Gel Extraction Kit, Qiagen), and ligated to form the complete ivT templates (Table B.6). The ligation reactions were separated on a 1.5% agarose gel, the appropriate bands were excised, and the DNA extracted. Extracted DNA was amplified using the HBB 5'-UTR Forward Primer and the HBB 3'-UTR Reverse Primer to obtain microgram-quantities of the assembled ivT templates (Table B.7)

A large-scale amplification was then performed to produce the quantity of each template required for in vitro transcription (Table B.8). Completed amplification reactions were subjected to two sequential gel purifications to remove nonspecific products.

C. HUSK ivT-RNA Transcript Synthesis

A high-fidelity polymerase was used in all stages of the dsDNA template synthesis to minimize sequence errors. Denaturing formaldehyde-agarose gel electrophoresis was performed to confirm that the transcripts transcribed from the HUSK ivT-RNA templates had the expected size before polyadenylation, that they were undegraded, and that the polyadenylation reaction added a poly(A) tail of sufficient length to promote efficient translation. Although full-length transcripts were produced from each template, completed reactions also contained large amounts of low-molecular-weight products, identified as a combination of prematurely terminated and degraded transcripts. Reducing the temperature of the in vitro-transcription reaction dramatically increased the fraction of full-length transcripts produced.

Several reports indicate that modifying the ivT reaction by adding single-strand binding protein (SSB)[51] or by reducing the reaction temperature[52] can reduce premature termination and increase the fraction of full-length transcripts produced. There was a significant reduction in T7 RNA-polymerase processivity at temperatures lower than 37° C. But the specificity of the reaction is increased, and a yield equivalent to that obtained at 37° C. can be obtained at 10 C by increasing the duration of the reaction from 1 hour to 20 hours.

Each HUSK ivT template was added to a T7 ivT reaction (mScript™ mRNA Production System, Epicentre®, Table B.9), and the resulting RNA was purified (RNeasy Mini Kit, Qiagen), quantitated, capped, and polyadenylated (mScript, Epicentre®, Tables B.10 and B.11). Capped, poly(A)+ HUSK ivT-RNA was synthesized using the mScript mRNA Production System (Epicentre®). The temperature and duration of the in vitro-transcription reaction were optimized for specificity and yield based on routine experimentation for the given cell and protein. The capped, poly(A)+ HUSK ivT-RNA was purified, quantitated, and stored at 4 C in RNase-free water with an RNase inhibitor (SUPERaseIn™, Ambion). 1 µg of each transcript both before and after poly(A) tailing was analyzed by denaturing formaldehyde-agarose gel electrophoresis (see Methods) to confirm that each transcript had the expected size before poly(A) tailing, to assess the level of degradation, and to measure the length of the poly(A) tail. The duration of the polyadenylation reaction was adjusted to yield a poly(A) tail of approximately 150 nucleotides, a length that can be varied as needed based on the experimental conditions and the encoded protein.

In addition to the seven HUSK transcripts, full-length endogenous, unmodified Transcript A was synthesized using a template containing the complete sequence of the endogenous mRNA (endogenous UTRs and an unmodified Kozak sequence). In all reactions low-molecular-weight products appeared after polyadenylation (dim features below dark bands). The polyadenylation reaction contains an RNase inhibitor, showing that the polyadenosine polymerase itself may possess a low level of RNase activity.

Example 3 siRNA Knockdown of IFNB1 Expression siRNA targeting IFNB1 was used to knock down its expression in order to suppress the innate immune response. The siRNA was delivered to MRC-5 fibroblasts by electroporation, with or without ivT-RNA. Mock-transfected cells that received no siRNA exhibited a 10,000-fold over expression of IFNB1 at 24 hours after HUSK ivT-RNA transfection. By contrast, cells that received both anti-IFNB1 siRNA and HUSK ivT-RNA exhibited only 50-100-fold over expression of IFNB1, corresponding to a knockdown efficiency of 99-99.5% (FIG. 7B). To give the RNAi machinery more time to locate and bind the siRNA before HUSK ivT-RNA transfection, cells were electroporated with siRNA, allowed to grow for 48 hours, and then electroporated with both siRNA and HUSK ivT-RNA. In this experiment, the cells that received no siRNA showed a 7500-fold over expression of IFNB1 relative to mock-transfected cells, while the cells that received siRNA showed a 15-fold over expression of IFNB1 relative to mock-transfected cells, corresponding to a knockdown efficiency of 99.8% (FIG. 7A). The differences in IFNB1 over expression in cells that received only HUSK ivT-RNA measured in these two experiments and in those described elsewhere in this text were likely due to small variations in the extremely low level of IFNB1 endogenously expressed by MRC-5 cells. For this reason, levels of over expression were only compared within and not between experiments, as each experiment has an independent mock-transfection control to which all expression data in that experiment are normalized.

Because knockdown efficiencies observed with electroporation in MRC-5 fibroblasts using siRNAs from the same vendor targeting other genes are typically between 80% and 90% (FIG. 9 and FIG. 10), the high efficiency of IFNB1 knockdown observed in these experiments showed that enough IFNB1 mRNA was destroyed by the RNAi machinery to disrupt the interferon-β-mediated amplification of the innate-immune response elicited by HUSK ivT-RNA transfection. This hypothesis is supported by the observation that several other genes involved in the innate immune response, although still over expressed relative to mock-transfected cells, are significantly less over expressed in cells that received siRNA targeting IFNB1 than in cells that received no siRNA (FIG. 7A). In particular, the PRRs TLR3 and RARRES3, which are 50-60-fold over expressed in cells that received only HUSK ivT-RNA are 20-30-fold over expressed in cells that received both HUSK ivT-RNA and IFNB1 siRNA. In addition, STAT1, STAT2, and EIF2AK2 all showed a similar reduction in the level of over expression relative to mock-transfected cells when cells were co-transfected with HUSK ivT-RNA and IFNB1 siRNA.

Although siRNA-mediated IFNB1 knockdown reduced the over expression of several genes involved in the innate-immune response elicited by HUSK ivT-RNA transfection in MRC-5 cells, innate immunity was not completely inhibited in these cells as indicated by the remaining >20-fold over expression of the PRRs TLR3 and RARRES3 and >5-fold over expression of IFNB1, STAT1, and EIF2AK2. In fact, IFNB1 knockdown appears to have had little or no effect on the inhibition of proliferation observed in ivT-RNA-transfected cells (FIG. 8), showing that in cells transfected with both HUSK ivT-RNA and IFNB1 siRNA, either the remaining low level of IFNB1 expression is sufficient to prevent the cells from proliferating or the cells are prevented from proliferating by a mechanism independent of interferon-β signaling.

TABLE A.1

TaqMan Gene Expression Assays and siRNAs.

|    | Gene    | TaqMan Assay   | siRNAs Product Numbers |
|----|---------|----------------|------------------------|
| 1  | TP53    | Hs00153340_m1  | s605, s607             |
| 2  | TLR3    | Hs00152933_m1  | s235                   |
| 3  | TLR7    | Hs00152971_m1  | s27842                 |
| 4  | RARRES3 | Hs00184937_m1  | s11818                 |
| 5  | IFNB1   | Hs02621180_s1  | s7187, s7189           |
| 6  | TICAM1  | Hs00706140_s1  | s45113                 |
| 7  | TICAM2  | Hs01934488_s1  | s51478                 |
| 8  | MAVS    | Hs00325038_m1  | s33178                 |
| 9  | STAT1   | Hs00234829_m1  | s277                   |
| 10 | STAT2   | Hs00237139_m1  | s13529, s13530         |
| 11 | EIF2AK2 | Hs00169345_m1  | s11185, s11187         |
| 12 | IRF3    | Hs00155574_m1  | s7509                  |
| 13 | TBK1    | Hs00179410_m1  | s762                   |
| 14 | CDKN1A  | Hs00355782_m1  | s415                   |
| 15 | CDKN2A  | Hs00233365_m1  | s223102, s223103       |
| 16 | RNASEL  | Hs00221692_m1  | s12064, s12065         |
| 17 | IFNAR1  | Hs00265057_m1  | s782                   |
| 18 | IFNAR2  | Hs00174198_m1  | s223909                |
| 19 | OAS1    | Hs00242943_m1  | s224141                |
| 20 | OAS2    | Hs00942643_m1  | s9794                  |
| 21 | OAS3    | Hs00196324_m1  | s9798                  |
| 22 | OASL    | Hs00388714_m1  | s16432                 |
| 23 | RB1     | Hs00153108_m1  | s524                   |
| 24 | ISG20   | Hs00158122_m1  | s7524, s7525           |
| 25 | IFIT1   | Hs00356631_g1  | s7152                  |
| 26 | IFIT2   | Hs00533665_m1  | s7147                  |
| 27 | EHMT2   | Hs00198710_m1  | s21468                 |

TaqMan Assays and Silencer Select siRNAs were purchased from Applied Biosystems, Inc.

TABLE B.1

Reverse transcription.

| Component | Final concentration | Volume/ μL | Reaction conditions |
|---|---|---|---|
| mRNA Template | 500 ng | 7.8 | 1: 65 C.-1 min |
| 2 μM ivT Reverse Primer | 0.25 μM | 2.5 | 2: 60 C.-45 min |
| 1:10 10 mM dNTP Mix (Promega) | 200 μM | 4 | 3: 90 C.-5 min |
| MonsterScript Reverse Transcriptase | 1:20 | 1 | 4: 4 C.-hold |
| 5X MonsterScript Buffer | 1X | 4 | |
| H2O | | 0.7 | |
| | | 20 Total | |

TABLE B.2

CDS amplification.

| Component | Final concentration | Volume/ μL | Reaction conditions |
|---|---|---|---|
| 5X Phusion HF Buffer | 1X | 5 | 1: 98 C.-1 min |
| 10 mM dNTP Mix | 200 μM | 0.5 | 2: 98 C.-15 sec x35 cycles |
| 5 μM CDS Forward Primer | .5 μM | 2.5 | 3: 72 C.-4 min |
| 5 μM CDS Reverse Primer | .5 μM | 2.5 | 4: 72 C.-10 min |
| Gene-Specific RT Reaction | 25 ng | 1 | 5: 4 C.-hold |
| Phusion Hot-Start DNA Polymerase | 0.5 U | 0.25 | |
| DMSO | 5% | 1.25 | |
| H2O | | 12 | |
| | | 25 Total | |

TABLE B.3

HBB 5'-UTR amplification.

| Component | Final concentration | Volume/ μL | Reaction conditions |
|---|---|---|---|
| 5X Phusion HF Buffer | 1X | 5 | 1: 98 C.-1 min |
| 10 mM dNTP Mix | 200 μM | 0.5 | 2: 98 C.-15 sec x45 cycles |
| 5 μM HBB 5-UTR Forward Primer | .5 μM | 2.5 | 3: 70 C.-20 sec |
| 5 μM HBB 5-UTR Reverse Primer | .5 μM | 2.5 | 4: 70 C.-2 min |
| Phusion Hot-Start DNA Polymerase | 0.5 U | 0.25 | 5: 4 C.-hold |
| DMSO | 5% | 1.25 | |
| H2O | | 13 | |
| | | 25 Total | |

TABLE B.4

HBB 3'-UTR amplification.

| Component | Final concentration | Volume/ μL | Reaction conditions |
|---|---|---|---|
| 5X Phusion HF Buffer | 1X | 5 | 1: 98 C.-1 min |
| 10 mM dNTP Mix | 200 μM | 0.5 | 2: 98 C.-15 sec x45 cycles |
| 5 μM HBB 3-UTR Forward Primer | .5 μM | 2.5 | 3: 68 C.-20 sec |
| 5 μM HBB 3-UTR Reverse Primer | .5 μM | 2.5 | 4: 68 C.-2 min |
| HBB RT Reaction | 25 ng | 1 | 5: 4 C.-hold |
| Phusion Hot-Start DNA Polymerase | 0.5 U | 0.25 | |
| DMSO | 5% | 1.25 | |
| H2O | | 12 | |
| | | 25 Total | |

TABLE B.5 ivT-template-component digestion.

| Component | Final concentration | Volume/ μL | Reaction conditions |
|---|---|---|---|
| 10X NEBuffer 1 | 1X | 5 | 1: 37 C.-1 hr |
| 100X BSA | 1X | 0.5 | 2: 65 C.-20 min |
| CDS or HBB UTR PCR Product | 0.25-1.5 μg | 30 | |
| NheI | 2.5 U | 0.25 | |
| AgeI | 2.5 U | 0.5 | |
| H2O | | 13.75 | |
| | | 50 Total | |

TABLE B.6 ivT-template-component ligation.

| Component | Final concentration | Volume/ μL | Reaction conditions |
|---|---|---|---|
| 10X *E. coli* DNA Ligase Buffer | 1X | 5 | 1: 16 C.-18 hr |
| Digested CDS PCR Product | 10-50 nM | 30 | 2: 65 C.-20 min |
| Digested HBB 5-UTR PCR Product | 50 nM | 5 | |
| Digested HBB 3-UTR PCR Product | 25 nM | 5 | |
| *E. coli* DNA Ligase | 5 U | 0.5 | |
| H2O | | 4.5 | |
| | | 50 Total | |

TABLE B.7

Ligation-product amplification.

| Component | Final concentration | Volume/ μL | Reaction conditions | |
|---|---|---|---|---|
| 5X Phusion HF Buffer | 1X | 5 | 1: 98 C.-1 min | |
| 10 mM dNTP Mix | 200 μM | 0.5 | 2: 98 C.-15 sec | x35 cycles |
| 5 μM HBB 5-UTR Forward Primer | .5 μM | 2.5 | 3: 68 C.-5 min | |
| 5 μM HBB 3-UTR Reverse Primer | .5 μM | 2.5 | 4: 68 C.-10 min | |
| HBB-UTR-Stabilized Template | .5 ng | 2.5 | 5: 4 C.-hold | |
| Phusion Hot-Start DNA Polymerase | 0.5 U | 0.25 | | |
| DMSO | 5% | 1.25 | | |
| H2O | | 10.5 | | |
| | | 25 | Total | |

TABLE B.8

Large-scale amplification.

| Component | Final concentration | Volume/ μL | Reaction conditions | |
|---|---|---|---|---|
| 5X Phusion HF Buffer | 1X | 5 | 1: 98 C.-1 min | |
| 10 mM dNTP Mix | 200 μM | 0.5 | 2: 98 C.-15 sec | x30 cycles |
| 5 μM HBB 5-UTR Forward Primer | .5 μM | 2.5 | 3: 68 C.-5 min | |
| 5 μM HBB 3-UTR Reverse Primer | .5 μM | 2.5 | 4: 68 C.-10 min | |
| HBB-UTR-Stabilized Template | 10 ng | 0.5 | 5: 4 C.-hold | |
| Phusion Hot-Start DNA Polymerase | 0.5 U | 0.25 | | |
| DMSO | 5% | 1.25 | | |
| H2O | | 12.5 | | |
| | | 25 | Total | |

TABLE B.9

In vitro transcription.

| Component | Volume/ μL | Reaction conditions |
|---|---|---|
| RNase-Free Water | 0.8 | 1: 10 C.-20 hr |
| mScript 10X Transcription Buffer | 2 | |
| NTP Solution | 7.2 | |
| 100 mM DTT | 2 | |
| mScript T7 Enzyme Mix | 2 | |
| T7 Template | 6 | |
| | 20 | Total |

TABLE B.10 m7G capping.

| Component | Volume/ μL | Reaction conditions |
|---|---|---|
| 10X ScriptCap Capping Buffer | 10 | 1: 37 C.-1 hr |
| 20 mM GTP | 5 | |
| 20 mM SAM | 1 | |
| SUPERaseIn | 5 | |
| mScript Capping Enzyme | 4 | |
| mScript 2'-O-Methyltransferase | 4 | |

TABLE B.10-continued m7G capping.

| Component | Volume/ μL | Reaction conditions |
|---|---|---|
| Heat-Denatured RNA | 71 | |
| | 100 | Total |

TABLE B.11

Poly(A) tailing.

| Component | Volume/ μL | Reaction conditions |
|---|---|---|
| mScript 10X Tailing Buffer | 12 | 1: 37 C.-40 min |
| SUPERaseIn | 1 | |
| 20 mM ATP | 6 | |
| mScript Poly(A) Polymerase | 5 | |
| 5'-Capped ivT-RNA | 100 | |
| | 124 | Total |

TABLE B.11-continued

Poly(A) tailing.

| Component | Final concentration |
|---|---|
| MEF Media | |
| DMEM | |
| Fetal bovine serum (FBS), heat-inactivated at 56 C. for 30 min | 10% |
| Non-essential amino acids 100X solution | 1X |
| hES-Cell Media[1] | |
| DMEM/F12 | |
| Knockout Serum Replacer | 20% |
| L-glutamine | 1 mm |
| β-mercaptoethanol | 7 μL/L |
| Non-essential amino acids 100X solution | 1X |
| bFGF | 4 ng/mL |
| MEF-Conditioned Media | |
| hES-Cell Media -bFGF conditioned for 24 hours on irradiated MEF1 (8000 rad) | |
| bFGF | 4 ng/mL |
| Y-27632 | 10 μM |
| MRC-5 Fibroblast Media | |
| MEM | |
| Fetal bovine serum (FBS) | 10% |

REFERENCES

1. Thomson, J. A. et al. Embryonic stem cell lines derived from human blastocysts. *Science* 282, 1145-1147 (1998).
2. Freed, C. R. et al. Transplantation of embryonic dopamine neurons for severe Parkinson's disease. *N Engl J Med* 344, 710-719 (2001).
3. Olanow, C. W. et al. A double-blind controlled trial of bilateral fetal nigral transplantation in Parkinson's disease. *Ann Neurol* 54, 403-414 (2003).
4. Keirstead, H. S. et al. Human embryonic stem cell-derived oligodendrocyte progenitor cell transplants remyelinate and restore locomotion after spinal cord injury. *J Neurosci* 25, 4694-4705 (2005).
5. Cummings, B. J. et al. Human neural stem cells differentiate and promote locomotor recovery in spinal cord-injured mice. *Proc Natl Acad Sci USA* 102, 14069-14074 (2005).
6. Iwanami, A. et al. Transplantation of human neural stem cells for spinal cord injury in primates. *J Neurosci Res* 80, 182-190 (2005).
7. Shapiro, A. M. et al. Islet transplantation in seven patients with type 1 diabetes mellitus using a glucocorticoid-free immunosuppressive regimen. *N Engl J Med* 343, 230-238 (2000).
8. Ryan, E. A. et al. Clinical outcomes and insulin secretion after islet transplantation with the Edmonton protocol. *Diabetes* 50, 710-719 (2001).
9. Shin, S., Dalton, S. & Stice, S. L. Human motor neuron differentiation from human embryonic stem cells. *Stem Cells Dev* 14, 266-269 (2005).
10. Li, X. J. et al. Specification of motoneurons from human embryonic stem cells. *Nat Biotechnol* 23, 215-221 (2005).
11. Schulz, T. C. et al. Differentiation of human embryonic stem cells to dopaminergic neurons in serum-free suspension culture. *Stem Cells* 22, 1218-1238 (2004).
12. Perrier, A. L. et al. Derivation of midbrain dopamine neurons from human embryonic stem cells. *Proc Natl Acad Sci USA* 101, 12543-12548 (2004).
13. Stewart, R., Christie, V. B. & Przyborski, S. A. Manipulation of human pluripotent embryonal carcinoma stem cells and the development of neural subtypes. *Stem Cells* 21, 248-256 (2003).
14. Kehat, I. et al. Human embryonic stem cells can differentiate into myocytes with structural and functional properties of cardiomyocytes. *J Clin Invest* 108, 407-414 (2001).
15. Rassoulzadegan, M. et al. RNA-mediated non-mendelian inheritance of an epigenetic change in the mouse. *Nature* 441, 469-474 (2006).
16. Kouskouti, A. & Talianidis, I. Histone modifications defining active genes persist after transcriptional and mitotic inactivation. *EMBO J* 24, 347-357 (2005).
17. Lande-Diner, L. et al. Role of DNA methylation in stable gene repression. *J Biol Chem* 282, 12194-12200 (2007).
18. Okitsu, C. Y. & Hsieh, C. L. DNA methylation dictates histone H3K4 methylation. *Mol Cell Biol* 27, 2746-2757 (2007).
19. Weiss, A., Keshet, I., Razin, A. & Cedar, H. DNA demethylation in vitro: involvement of RNA. *Cell* 86, 709-718 (1996).
20. Cervoni, N. & Szyf, M. Demethylase activity is directed by histone acetylation. *J Biol Chem* 276, 40778-40787 (2001).
21. Swigut, T. & Wysocka, J. H3K27 demethylases, at long last. *Cell* 131, 29-32 (2007).
22. Farthing, C. R. et al. Global mapping of DNA methylation in mouse promoters reveals epigenetic reprogramming of pluripotency genes. *PLoS Genet.* 4, e1000116 (2008).
23. Meissner, A. et al. Genome-scale DNA methylation maps of pluripotent and differentiated cells. *Nature* 454, 766-770 (2008).
24. Hajkova, P. et al. Chromatin dynamics during epigenetic reprogramming in the mouse germ line. *Nature* 452, 877-881 (2008).
25. Peters, A. H. et al. Loss of the Suv39h histone methyltransferases impairs mammalian heterochromatin and genome stability. *Cell* 107, 323-337 (2001).
26. Sinkkonen, L. et al. MicroRNAs control de novo DNA methylation through regulation of transcriptional repressors in mouse embryonic stem cells. *Nat Struct Mol Biol* 15, 259-267 (2008).
27. Bruniquel, D. & Schwartz, R. H. Selective, stable demethylation of the interleukin-2 gene enhances transcription by an active process. *Nat Immunol* 4, 235-240 (2003).
28. Meehan, R. R., Lewis, J. D., McKay, S., Kleiner, E. L. & Bird, A. P. Identification of a mammalian protein that binds specifically to DNA containing methylated CpGs. *Cell* 58, 499-507 (1989).
29. Meehan, R. R., Lewis, J. D. & Bird, A. P. Characterization of MeCP2, a vertebrate DNA binding protein with affinity for methylated DNA. *Nucleic Acids Res* 20, 5085-5092 (1992).
30. Lewis, J. D. et al. Purification, sequence, and cellular localization of a novel chromosomal protein that binds to methylated DNA. *Cell* 69, 905-914 (1992).
31. Smallwood, A., Esteve, P. O., Pradhan, S. & Carey, M. Functional cooperation between HP1 and DNMT1 mediates gene silencing. *Genes Dev* 21, 1169-1178 (2007).
32. Sawai, K., Ohno, K., Iijima, Y., Levin, B. & Meruelo, D. A novel method of cell-specific mRNA transfection. *Mol Genet Metab* 64, 44-51 (1998).

33. Bonehill, A. et al. Messenger RNA-electroporated dendritic cells presenting MAGE-A3 simultaneously in HLA class I and class II molecules. *J Immunol* 172, 6649-6657 (2004).
34. Van Tendeloo, V. F. et al. Highly efficient gene delivery by mRNA electroporation in human hematopoietic cells: superiority to lipofection and passive pulsing of mRNA and to electroporation of plasmid cDNA for tumor antigen loading of dendritic cells. *Blood* 98, 49-56 (2001).
35. Ponsaerts, P. et al. Highly efficient mRNA-based gene transfer in feeder-free cultured H9 human embryonic stem cells. *Cloning Stem Cells* 6, 211-216 (2004).
36. Paterson, B. M. & Rosenberg, M. Efficient translation of prokaryotic mRNAs in a eukaryotic cell-free system requires addition of a cap structure. *Nature* 279, 692-696 (1979).
37. Melton, D. A. et al. Efficient in vitro synthesis of biologically-active RNA and RNA hybridization probes from plasmids containing a bacteriophage SP6 promoter. *Nucleic Acids Res* 12, 7035-7056 (1984).
38. Stepinski, J., Waddell, C., Stolarski, R., Darzynkiewicz, E. & Rhoads, R. E. Synthesis and properties of mRNAs containing the novel "anti-reverse" cap analogs 7-methyl (3'-O-methyl)GpppG and 7-methyl (3'-deoxy)GpppG. *RNA* 7, 1486-1495 (2001).
39. Mockey, M. et al. mRNA transfection of dendritic cells: synergistic effect of ARCA mRNA capping with Poly(A) chains in cis and in trans for a high protein expression level. *Biochem Biophys Res Commun* 340, 1062-1068 (2006).
40. Cheung, C. Y., Murthy, N., Stayton, P. S. & Hoffman, A. S. A pH-sensitive polymer that enhances cationic lipid-mediated gene transfer. *Bioconjug Chem* 12, 906-910 (2001).
41. Gonzalez, G., Pfannes, L., Brazas, R. & Striker, R. Selection of an optimal RNA transfection reagent and comparison to electroporation for the delivery of viral RNA. *J Virol Methods* 145, 14-21 (2007).
42. Malone, R. W., Felgner, P. L. & Verma, I. M. Cationic liposome-mediated RNA transfection. *Proc Natl Acad Sci USA* 86, 6077-6081 (1989).
43. Prasad, T. K., Rangaraj, N. & Rao, N. M. Quantitative aspects of endocytic activity in lipid-mediated transfections. *FEBS Lett* 579, 2635-2642 (2005).
44. Zabner, J., Fasbender, A. J., Moninger, T., Poellinger, K. A. & Welsh, M. J. Cellular and molecular barriers to gene transfer by a cationic lipid. *J Biol Chem* 270, 18997-19007 (1995).
45. Zohra, F. T., Chowdhury, E. H., Tada, S., Hoshiba, T. & Akaike, T. Effective delivery with enhanced translational activity synergistically accelerates mRNA-based transfection. *Biochem Biophys Res Commun* 358, 373-378 (2007).
46. Kozak, M. Point mutations define a sequence flanking the AUG initiator codon that modulates translation by eukaryotic ribosomes. *Cell* 44, 283-292 (1986).
47. Yu, J. & Russell, J. E. Structural and functional analysis of an mRNP complex that mediates the high stability of human beta-globin mRNA. *Mol Cell Biol* 21, 5879-5888 (2001).
48. Jiang, Y., Xu, X. S. & Russell, J. E. A nucleolin-binding 3' untranslated region element stabilizes beta-globin mRNA in vivo. *Mol Cell Biol* 26, 2419-2429 (2006).
49. Russell, J. E. & Liebhaber, S. A. The stability of human beta-globin mRNA is dependent on structural determinants positioned within its 3' untranslated region. *Blood* 87, 5314-5323 (1996).
50. Watanabe, K. et al. A ROCK inhibitor permits survival of dissociated human embryonic stem cells. *Nat Biotechnol* 25, 681-686 (2007).
51. Ben Aziz, R. & Soreq, H. Improving poor in vitro transcription from G,C-rich genes. *Nucleic Acids Res* 18, 3418 (1990).
52. Krieg, P. A. Improved synthesis of full-length RNA probe at reduced incubation temperatures. *Nucleic Acids Res* 18, 6463 (1990).
53. Alexopoulou, L., Holt, A. C., Medzhitov, R. & Flavell, R. A. Recognition of double-stranded RNA and activation of NF-kappaB by Toll-like receptor 3. *Nature* 413, 732-738 (2001).
54. Kariko, K., Ni, H., Capodici, J., Lamphier, M. & Weissman, D. mRNA is an endogenous ligand for Toll-like receptor 3. *J Biol Chem* 279, 12542-12550 (2004).
55. Diebold, S. S., Kaisho, T., Hemmi, H., Akira, S. & Reis e Sousa, C Innate antiviral responses by means of TLR7-mediated recognition of single-stranded RNA. *Science* 303, 1529-1531 (2004).
56. Yoneyama, M. et al. The RNA helicase RIG-I has an essential function in double-stranded RNA-induced innate antiviral responses. *Nat Immunol* 5, 730-737 (2004).
57. Hornung, V. et al. 5'-Triphosphate RNA is the ligand for RIG-I. *Science* 314, 994-997 (2006).
58. Saito, T., Owen, D. M., Jiang, F., Marcotrigiano, J. & Gale, M., Jr. Innate immunity induced by composition-dependent RIG-I recognition of hepatitis C virus RNA. *Nature* 454, 523-527 (2008).
59. Das, H. K. et al. Protein synthesis in rabbit reticulocytes. Purification and characterization of a double-stranded RNA-dependent protein synthesis inhibitor from reticulocyte lysates. *J Biol Chem* 256, 6491-6495 (1981).
60. Levin, D. H., Petryshyn, R. & London, I. M. Characterization of purified double-stranded RNA-activated eIF-2 alpha kinase from rabbit reticulocytes. *J Biol Chem* 256, 7638-7641 (1981).
61. Kariko, K., Buckstein, M., Ni, H. & Weissman, D. Suppression of RNA recognition by Toll-like receptors: the impact of nucleoside modification and the evolutionary origin of RNA. *Immunity* 23, 165-175 (2005).
62. Desrosiers, R., Friderici, K. & Rottman, F. Identification of methylated nucleosides in messenger RNA from Novikoff hepatoma cells. *Proc Natl Acad Sci USA* 71, 3971-3975 (1974).
63. Furuichi, Y. et al. Methylated, blocked 5 termini in HeLa cell mRNA. *Proc Natl Acad Sci USA* 72, 1904-1908 (1975).
64. Reik, W. Stability and flexibility of epigenetic gene regulation in mammalian development. *Nature* 447, 425-432 (2007).
65. Bird, A. DNA methylation patterns and epigenetic memory. *Genes Dev* 16, 6-21 (2002).
66. Bode, J. G., Brenndorfer, E. D. & Haussinger, D. Subversion of innate host antiviral strategies by the hepatitis C virus. *Arch Biochem Biophys* 462, 254-265 (2007).
67. Jessberger, et al. "Directed differentiation of hippocampal stem/progenitor cells in the adult brain." Nat. Neurosci. Vol. 11. 2008.
68. Choi, et al. "MyoD converts primary dermal fibroblasts, chondroblasts, smooth muscle, and retinal pigmented epithelial cells into striated mononucleated myoblasts and multinucleated myotubes." PNAS. Vol. 87. 1990.
69. Feng, et al. "PU.1 and C/EBPα/β convert fibroblasts into macrophage-like cells." PNAS. Vol. 105. 2008.

70. Zhou et al. "In vivo reprogramming of adult pancreatic exocrine cells to β-cells." Nature. Vol. 455. 2008.
71. Kim, et al. "Oct4-Induced Pluripotency in Adult Neural Stem Cells." Cell. Vol. 136. 2009.
72. Kim, et al. "Pluripotent stem cells induced from adult neural stem cells by reprogramming with two factors." Nature. Vol. 454. 2008.
73. Okita, et al. "Generation of germline-competent induced pluripotent stem cells." Nature. Vol. 448. 2007.
74. Wernig, et al. "In vitro reprogramming of fibroblasts into a pluripotent ES-cell-like state." Nature. Vol. 448. 2007.
75. Maherali, et al. "Directly Reprogrammed Fibroblasts Show Global Epigenetic Remodeling and Widespread Tissue Contribution." Cell Stem Cell. Vol. 1. 2007.

What is claimed is:

1. An in vitro method for suppressing the innate immune response of a cell to transfection with a nucleic acid comprising steps of:
introducing to the cell an effective amount of B18R, alone or in combination with one or more siRNA, antisense oligonucleotides, or a combination thereof that reduces the activity of one or more proteins in the innate immune response pathway selected from the group consisting of TP53, TLR3, TLR7, RARRES3, IFNA1, IFNA2, IFNA4, IFNA5, IFNA6, IFNA7, IFNA8, IFNA10, IFNA13, IFNA14, IFNA16, IFNA17, IFNA21, IFNK, IFNB1, IL6, TICAM1, TICAM2, MAVS, STAT1, STAT2, EIF2AK2, IRF3, TBK1, CDKN1A, CDKN2A, RNASEL, IFNAR1, IFNAR2, OAS1, OAS2, OAS3, OASL, RB1, ISG15, ISG20, IFIT1, IFIT2, IFIT3; and
introducing a nucleic acid molecule into the cell, wherein the nucleic acid molecule encodes a protein that changes the phenotype of the cell in that the cell differentiates, dedifferentiates, or transdifferentiates, and wherein the nucleic acid molecule is selected from the group consisting of a single-stranded RNA molecule, a double-stranded RNA molecule, or a single- or double-stranded DNA/RNA chimera.

2. The method of claim 1, wherein the cell is an animal cell and the siRNA or antisense oligonucleotides are specifically hybridizable to an RNA or DNA molecule encoding any of human TP53, TLR3, TLR7, RARRES3, IFNA1, IFNA2, IFNA4, IFNA5, IFNA6, IFNA7, IFNA8, IFNA10, IFNA13, IFNA14, IFNA16, IFNA17, IFNA21, IFNK, IFNB1, IL6, TICAM1, TICAM2, MAVS, STAT1, STAT2, ETF2AK2, IRF3, TBK1, CDKN1A, CDKN2A, RNASEL, IFNAR1, IFNAR2, OAS1, OAS2, OAS3, OASL, RB1, ISG15, IS020, IFIT1, IFIT2, IFIT3, and IFIT5.

3. The method of claim 1, wherein introducing the siRNA or antisense oligonucleotides is by electroporation, lipid-mediated transfection, ballistic transfection, magnetofection, peptide-mediated transfection, microinjection, or a combination thereof.

4. The method of claim 1, wherein the step of introducing the nucleic acid molecule is by transfection.

5. The method of claim 1, wherein the single-stranded RNA molecule is in vitro-transcribed RNA encoding the protein that changes the phenotype of the cell.

6. The method of claim 1, wherein the introduction to the cell of an effective amount of B18R, alone or in combination with one or more siRNA, antisense oligonucleotides, or a combination thereof and the introduction of the nucleic acid molecule into the cell are simultaneous.

7. The method of claim 1, wherein the introduction to the cell of an effective amount of B18R, alone or in combination with one or more siRNA, antisense oligonucleotides, or a combination thereof is repeated two or more times.

8. The method of claim 1, wherein the introduction of the nucleic acid molecule into the cell is repeated two or more times.

9. The method of claim 1, wherein the introduction to the cell of an effective amount of B18R, alone or in combination with one or more siRNA, antisense oligonucleotides, or a combination thereof is performed up to about 24-72 hours before the introduction of the nucleic acid molecule into the cell.

10. The method of claim 1, wherein the cell is an animal cell.

11. The method of claim 10, wherein the animal cell is a human cell.

12. The method of claim 1, wherein the nucleic acid molecule encodes a protein selected from the group consisting of OCT4, SOX2, KLF4, MYC, NANOG; LIN28, MYOD1, Ascl1, PU.1 C/EBPα; C/EBPβ, Ngn3, Pdxl, Mafa, and Esrrb.

13. The method of claim 10, wherein the animal is a mammal, the cell is an adult hippocampal stem cell, the encoded protein is Ascl 1 and the phenotypic change is differentiation of the cell to an oligodendrocyte.

14. The method of claim 10, wherein the animal is a mammal, the cell is a neural stem cell transfected with a plurality of different in vitro transcribed-RNAs each encoding Oct4, Klf4 or c-Myc protein, and the phenotypic change is dedifferentiation of the neural stem cell to a pluripotent stem cell.

15. The method of claim 10, wherein the animal is a mammal, the cell is a non-insulin-producing pancreatic exocrine cell transfected with a plurality of different in vitro-transcribed RNAs each encoding Ngn3, Pdxl, or Mafa protein, and the phenotypic change is transdifferentiation of the non-insulin-producing pancreatic exocrine cell to an insulin-producing beta islet cell.

16. The method of claim 10, wherein the animal is a mammal, the cell is a fibroblast transfected with a plurality of different in vitro-transcribed RNAs each encoding Oct4, Sox2, Klf4, and c-Myc protein, and the phenotypic change is dedifferentiation of the fibroblast to a pluripotent stem cell.

17. The method of claim 10, wherein the animal is a mammal, the cell is selected from a fibroblast, a chondroblast, a smooth muscle cell, and a retinal pigmented epithelial cell, the encoded protein is MyoD, and the phenotypic change is transdifferentiation of the cell to a myoblast.

18. The method of claim 10, wherein the animal is a mammal, the cell is a fibroblast transfected with a plurality of different in vitro-transcribed RNAs each encoding PU.1 or C/EBPα/β, and the desired phenotypic change is transdifferentiation of the fibroblast to a macrophage.

19. The method of claim 1, wherein the nucleic acid molecule is modified RNA.

20. The method of claim 1, wherein the one or more siRNA, antisense oligonucleotides, or a combination thereof targets the nucleic acids encoding a plurality of the proteins in the innate immune response pathway.

21. The method of claim 1, wherein the one or more siRNA, antisense oligonucleotides, or a combination thereof comprises a set of siRNAs, antisense oligonucleotides, or a combination thereof that individually target different proteins in the innate immune response pathway.

22. The method of claim 12, wherein the OCT4 is encoded by SEQ ID NO: 1; SOX2 is encoded by SEQ ID NO: 2, KLF4 is encoded by SEQ ID NO: 3, MYC is encoded by SEQ ID NO: 4, NANOG is encoded by SEQ ID NO: 5, LIN28 is encoded by SEQ ID NO: 6, MYOD1 is encoded by SEQ ID NO: 7, Ascl1 is encoded by SEQ ID NO: 8, PU.1 is encoded by SEQ ID NO: 9, C/EBPα is encoded by SEQ ID NO: 10, C/EBPβ is encoded by SEQ ID NO: 11, Ngn3 is encoded by SEQ ID NO: 12, Pdx1 is encoded by SEQ ID NO: 713, Mafa is encoded by SEQ ID NO: 14, and Esrrb is encoded by SEQ ID NO: 15.

* * * * *

SEQUENCE LISTING

```
<160> NUMBER OF SEQ ID NOS: 23

<210> SEQ ID NO 1
<211> LENGTH: 1411
<212> TYPE: DNA
<213> ORGANISM: Homo sapiens

<400> SEQUENCE: 1
ccttcgcaag ccctcatttc accaggcccc cggcttgggg cgccttcctt ccccatggcg      60
ggacacctgg cttcggattt cgccttctcg cccccctccag gtggtggagg tgatgggcca    120 gggggccgg agccgggctg ggttgatcct cggacctggc taagcttcca aggccctcct     180
ggagggccag gaatcgggcc gggggttggg ccaggctctg aggtgtgggg gattccccca    240
tgccccccgc cgtatgagtt ctgtgggggg atggcgtact gtgggcccca ggttggagtg    300
gggctagtgc cccaaggcgg cttggagacc tctcagcctg agggcgaagc aggagtcggg    360
gtggagagca actccgatgg ggcctcccg gagccctgca ccgtcacccc tggtgccgtg     420
aagctggaga aggagaagct ggagcaaaac ccggaggagt cccaggacat caaagctctg    480
cagaaagaac tcgagcaatt tgccaagctc ctgaagcaga gaggatcac cctgggatat     540 acacaggccg atgtggggct caccctgggg gttctatttg ggaaggtatt cagccaaacg    600
accatctgcc gctttgaggc tctgcagctt agcttcaaga acatgtgtaa gctgcggccc    660
ttgctgcaga agtgggtgga ggaagctgac aacaatgaaa atcttcagga gatatgcaaa    720
gcagaaaccc tcgtgcaggc ccgaaagaga aagcgaacca gtatcgagaa ccgagtgaga    780
ggcaacctgg agaatttgtt cctgcagtgc ccgaaaccca cactgcagca gatcagccac    840
atcgcccagc agcttgggct cgagaaggat gtggtccgag tgtggttctg taaccggcgc    900
cagaagggca agcgatcaag cagcgactat gcacaacgag aggattttga ggctgctggg    960
tctcctttct caggggacc agtgtccttt cctctgccc cagggcccca ttttggtacc     1020
ccaggctatg ggagccctca cttcactgca ctgtactcct cggtcccttt ccctgagggg   1080
gaagcctttc cccctgtctc cgtcaccact ctgggctctc ccatgcattc aaactgaggt    1140
gcctgccctt ctaggaatgg gggacagggg gaggggagga gctagggaaa gaaaacctgg   1200
agtttgtgcc agggtttttg ggattaagtt cttcattcac taaggaagga attgggaaca   1260
caaagggtgg gggcagggga gtttggggca actggttgga gggaaggtga agttcaatga   1320
tgctcttgat tttaatccca catcatgtat cacttttttc ttaaataaag aagcctggga   1380
cacagtagat agacacactt aaaaaaaaaa a                                   1411

<210> SEQ ID NO 2
<211> LENGTH: 2518
<212> TYPE: DNA
<213> ORGANISM: Homo sapiens

<400> SEQUENCE: 2
ctattaactt gttcaaaaaa gtatcaggag ttgtcaaggc agagaagaga gtgtttgcaa      60
aaggggggaa gtagtttgct gcctctttaa gactaggact gagagaaaga agaggagaga    120
```

```
gaaagaaagg gagagaagtt tgagcccag gcttaagcct ttccaaaaaa taataataac      180
aatcatcggc ggcggcagga tcggccagag gaggagggaa gcgctttttt tgatcctgat      240
tccagtttgc ctctctcttt ttttccccca aattattctt cgcctgattt tcctcgcgga      300
gccctgcgct cccgacaccc ccgcccgcct ccctcctcc tctcccccg cccgcgggcc       360 ccccaaagtc ccggccgggc cgagggtcgg cggccgccgg cgggccgggc ccgcgcacag      420
cgcccgcatg tacaacatga tggagacgga gctgaagccg ccgggccgc agcaaacttc       480 ggggggcggc ggcggcaact ccaccgcggc ggcggccggc ggcaaccaga aaaacagccc      540
ggaccgcgtc aagcggccca tgaatgcctt catggtgtgg tcccgcgggc agcggcgcaa      600
gatggcccag gagaaccccca agatgcacaa ctcggagatc agcaagcgcc tgggcgccga     660
gtggaaactt ttgtcggaga cggagaagcg gccgttcatc gacgaggcta agcggctgcg      720
agcgctgcac atgaaggagc acccggatta taaataccgg ccccggcgga aaaccaagac      780
gctcatgaag aaggataagt acacgctgcc cggcggctg ctggccccg gcggcaatag       840 catggcgagc ggggtcgggg tgggcgccgg cctgggcgcg ggcgtgaacc agcgcatgga     900
cagttacgcg cacatgaacg gctggagcaa cggcagctac agcatgatgc aggaccagct     960
gggctacccg cagcacccgg gcctcaatgc gcacggcgca gcgcagatgc agcccatgca     1020
ccgctacgac gtgagcgccc tgcagtacaa ctccatgacc agctcgcaga cctacatgaa     1080
cggctcgccc acctacagca tgtcctactc gcagcagggc accctggca tggctcttgg     1140 ctccatgggt tcggtggtca agtccgaggc cagctccagc cccctgtgg ttacctcttc     1200 ctcccactcc agggcgccct gccaggccgg ggacctccgg gacatgatca gcatgtatct     1260
ccccggcgcc gaggtgccgg aacccgccgc ccccagcaga cttcacatgt cccagcacta     1320
ccagagcggc ccggtgcccg gcacggccat taacggcaca ctgcccctct cacacatgtg     1380
agggccggac agcgaactgg aggggggaga aattttcaaa gaaaacgag ggaaatggga     1440 ggggtgcaaa agaggagagt aagaaacagc atggagaaaa cccggtacgc tcaaaaagaa     1500
aaaggaaaaa aaaaaatccc atcacccaca gcaaatgaca gctgcaaaag agaacaccaa     1560
tcccatccac actcacgcaa aaaccgcgat gccgacaaga aaactttat gagagagatc      1620 ctggacttct ttttgggga ctattttgt acagagaaaa cctggggagg gtggggaggg       1680 cggggggaatg gaccttgtat agatctggag gaaagaaagc tacgaaaaac ttttaaaag     1740 ttctagtggt acggtaggag ctttgcagga agtttgcaaa agtctttacc aataatattt     1800
agagctagtc tccaagcgac gaaaaaaatg ttttaatatt tgcaagcaac ttttgtacag    1860
tatttatcga gataaacatg gcaatcaaaa tgtccattgt ttataagctg agaatttgcc     1920
aatatttttc aaggagaggc ttcttgctga atttttgattc tgcagctgaa atttaggaca     1980
gttgcaaacg tgaaagaag aaaattattc aaatttggac atttttaattg tttaaaaatt     2040 gtacaaaagg aaaaaattag aataagtact ggcgaaccat ctctgtggtc ttgtttaaaa     2100
agggcaaaag ttttagactg tactaaattt tataacttac tgttaaaagc aaaaatggcc     2160
atgcaggttg acaccgttgg taattttataa tagcttttgt tcgatcccaa ctttccattt     2220
tgttcagata aaaaaaacca tgaaattact gtgtttgaaa tattttctta tggtttgtaa     2280
tatttctgta aatttattgt gatattttaa ggttttcccc cctttatttt ccgtagttgt     2340
attttaaaag attcggctct gtattatttg aatcagtctg ccgagaatcc atgtatatat    2400
ttgaactaat atcatcctta taacaggtac attttcaact taagttttta ctccattatg    2460
```

| | |
|---|---|
| cacagtttga gataaataaa tttttgaaat atggacactg aaaaaaaaaa aaaaaaaa | 2518 |

<210> SEQ ID NO 3
<211> LENGTH: 2949
<212> TYPE: DNA
<213> ORGANISM: Homo sapiens

<400> SEQUENCE: 3

| | |
|---|---|
| agtttcccga ccagagagaa cgaacgtgtc tgcgggcgcg cggggagcag aggcggtggc | 60 |
| gggcggcggc ggcaccggga gccgccgagt gaccctcccc cgcccctctg gcccccacc | 120 |
| ctcccacccg cccgtggccc cgcgcccatgg ccgcgcgcgc tccacacaac tcaccggagt | 180 |
| ccgcgccttg cgccgccgac cagttcgcag ctccgcgcca cggcagccag tctcacctgg | 240 |
| cggcaccgcc cgcccaccgc ccggccaca gccctgcgc ccacggcagc actcgaggcg | 300 |
| accgcgacag tggtggggga cgctgctgag tggaagagag cgcagcccgg ccaccggacc | 360 |
| tacttactcg ccttgctgat tgtctatttt tgcgtttaca acttttctaa gaacttttgt | 420 |
| atacaaagga actttttaaa aaagacgctt ccaagttata tttaatccaa agaagaagga | 480 |
| tctcggccaa tttggggttt tgggttttgg cttcgtttct tctcttcgtt gactttgggg | 540 |
| ttcaggtgcc ccagctgctt cgggctgccg aggaccttct gggcccccac attaatgagg | 600 |
| cagccacctg gcgagtctga catggctgtc agcgacgcgc tgctcccatc tttctccacg | 660 |
| ttcgcgtctg gccggcgggg aagggagaag acactgcgtc aagcaggtgc cccgaataac | 720 |
| cgctggcggg aggagctctc ccacatgaag cgacttcccc cagtgcttcc ggccgcccc | 780 |
| tatgacctgg cggcggcgac cgtggccaca gacctggaga cggcggagc cggtgcggct | 840 |
| tgcggcggta gcaacctggc gccctacct cggagagaga ccgaggagtt caacgatctc | 900 |
| ctggacctga actttattct ctccaattcg ctgacccatc ctccggagtc agtggccgcc | 960 |
| accgtgtcct cgtcagcgtc agcctcctct tcgtcgtcgc cgtcgagcag cggccctgcc | 1020 |
| agcgcgccct ccacctgcag cttcacctat ccgatccggg ccgggaacga cccgggcgtg | 1080 |
| gcgccgggcg gcacgggcgg aggcctcctc tatggcaggg agtccgctcc ccctccgacg | 1140 |
| gctcccttca acctggcgga catcaacgac gtgagcccct cgggcggctt cgtggccgag | 1200 |
| ctcctgcggc cagaattgga cccggtgtac attccgccgc agcagccgca gccgccaggt | 1260 |
| ggcgggctga tggcaagtt cgtgctgaag gcgtcgctga cgcccctgg cagcgagtac | 1320 |
| ggcagcccgt cggtcatcag cgtcagcaaa ggcagccctg acggcagcca cccggtggtg | 1380 |
| gtggcgccct acaacggcgg gccgccgcgc acgtgcccca agatcaagca ggaggcggtc | 1440 |
| tcttcgtgca cccacttggg cgctggaccc cctctcagca atggccaccg gccggctgca | 1500 |
| cacgacttcc ccctgggcg gcagctcccc agcaggacta ccccgaccct gggtcttgag | 1560 |
| gaagtgctga gcagcaggga ctgtcaccct gccctgccgc ttcctcccgg cttccatccc | 1620 |
| cacccggggc ccaattaccc atccttcctg cccgatcaga tgcagccgca agtcccgccg | 1680 |
| ctccattacc aagagctcat gccacccgt tcctgcatgc cagaggagcc caagccaaag | 1740 |
| aggggaagac gatcgtggcc ccggaaaagg accgccaccc acacttgtga ttacgcgggc | 1800 |
| tgcggcaaaa cctacacaaa gagttcccat ctcaaggcac acctgcgaac ccacacaggt | 1860 |
| gagaaacctt accactgtga ctgggacggc tgtggatgga aattcgcccg ctcagatgaa | 1920 |
| ctgaccaggc actaccgtaa acacacgggg caccgcccgt tccagtgcca aaatgcgac | 1980 |
| cgagcatttt ccaggtcgga ccacctcgcc ttacacatga gaggcattt ttaaatccca | 2040 |
| gacagtggat atgacccaca ctgccagaag agaattcagt atttttact tttcacactg | 2100 |

```
tcttcccgat gagggaagga gcccagccag aaagcactac aatcatggtc aagttcccaa    2160
ctgagtcatc ttgtgagtgg ataatcagga aaaatgagga atccaaaaga caaaaatcaa    2220
agaacagatg gggtctgtga ctggatcttc tatcattcca attctaaatc cgacttgaat    2280
attcctggac ttacaaaatg ccaaggggt gactggaagt tgtggatatc agggtataaa    2340
ttatatccgt gagttggggg agggaagacc agaattccct tgaattgtgt attgatgcaa    2400
tataagcata aaagatcacc ttgtattctc tttaccttct aaaagccatt attatgatgt    2460
tagaagaaga ggaagaaatt caggtacaga aaacatgttt aaatagccta atgatggtg    2520 cttggtgagt cttggttcta aaggtaccaa acaaggaagc caaagttttc aaactgctgc    2580
atactttgac aaggaaaatc tatatttgtc ttccgatcaa catttatgac ctaagtcagg    2640 taatataccct ggtttacttc tttagcattt ttatgcagac agtctgttat gcactgtggt    2700
ttcagatgtg caataatttg tacaatggtt tattcccaag tatgccttaa gcagaacaaa    2760 tgtgttttc tatatagttc cttgccttaa taaatatgta atataaattt aagcaaacgt    2820
ctattttgta tatttgtaaa ctacaaagta aaatgaacat tttgtggagt ttgtattttg    2880
catactcaag gtgagaatta agttttaaat aaacctataa tattttatct gaaaaaaaaa    2940
aaaaaaaaa                                                             2949

<210> SEQ ID NO 4
<211> LENGTH: 2377
<212> TYPE: DNA
<213> ORGANISM: Homo sapiens

<400> SEQUENCE: 4 accccccgagc tgtgctgctc gcggccgcca ccgccgggcc ccggccgtcc ctggctcccc      60
tcctgcctcg agaagggcag ggcttctcag aggcttggcg ggaaaaagaa cggagggagg     120
gatcgcgctg agtataaaag ccggttttcg gggctttatc taactcgctg tagtaattcc     180
agcgagaggc agagggagcg agcgggcggc cggctagggt ggaagagccg ggcgagcaga     240
gctgcgctgc gggcgtcctg ggaagggaga tccggagcga ataggggct tcgcctctgg      300 cccagccctc ccgctgatcc cccagccagc ggtccgcaac ccttgccgca tccacgaaac     360
tttgcccata gcagcgggcg ggcactttgc actggaactt acaacacccg agcaaggacg     420
cgactctccc gacgcgggga ggctattctg cccatttggg gacacttccc cgccgctgcc     480
aggacccgct tctctgaaag gctctccttg cagctgctta gacgctggat ttttttcggg    540
tagtggaaaa ccagcagcct cccgcgacga tgcccctcaa cgttagcttc accaacagga     600
actatgacct cgactacgac tcggtgcagc cgtatttcta ctgcgacgag gaggagaact     660
tctaccagca gcagcagcag agcgagctgc agccccggc gccagcgag gatatctgga      720 agaaattcga gctgctgccc acccccgcccc tgtcccctag ccgccgctcc gggctctgct    780
cgccctccta cgttgcggtc acacccttct cccttcgggg agacaacgac ggcggtggcg    840
ggagcttctc cacggccgac cagctggaga tggtgaccga gctgctggga ggagacatgg    900
tgaaccagag tttcatctgc gacccggacg acgagacctt catcaaaaac atcatcatcc    960
aggactgtat gtggagcggc ttctcggccg ccgccaagct cgtctcagag aagctggcct   1020
cctaccaggc tgcgcgcaaa gacagcggca gcccgaaccc cgccgcggc cacagcgtct    1080 gctccacctc cagcttgtac ctgcaggatc tgagcgccgc cgcctcagag tgcatcgacc   1140
cctcggtggt cttcccctac cctctcaacg acagcagctc gcccaagtcc tgcgcctcgc   1200
```

| | |
|---|---|
| aagactccag cgccttctct ccgtcctcgg attctctgct ctcctcgacg gagtcctccc | 1260 |
| cgcagggcag ccccgagccc ctggtgctcc atgaggagac accgcccacc accagcagcg | 1320 |
| actctgagga ggaacaagaa gatgaggaag aaatcgatgt tgtttctgtg gaaagaggc | 1380 |
| aggctcctgg caaaaggtca gagtctggat caccttctgc tggaggccac agcaaacctc | 1440 |
| ctcacagccc actggtcctc aagaggtgcc acgtctccac acatcagcac aactacgcag | 1500 |
| cgcctccctc cactcggaag gactatcctg ctgccaagag ggtcaagttg gacagtgtca | 1560 |
| gagtcctgag acagatcagc aacaaccgaa aatgcaccag ccccaggtcc tcggacaccg | 1620 |
| aggagaatgt caagaggcga acacacaacg tcttggagcg ccagaggagg aacgagctaa | 1680 |
| aacggagctt ttttgccctg cgtgaccaga tcccggagtt ggaaaacaat gaaaaggccc | 1740 |
| ccaaggtagt tatccttaaa aaagccacag catacatcct gtccgtccaa gcagaggagc | 1800 |
| aaaagctcat ttctgaagag gacttgttgc ggaaacgacg agaacagttg aaacacaaac | 1860 |
| ttgaacagct acggaactct tgtgcgtaag gaaaagtaag gaaaacgatt ccttctaaca | 1920 |
| gaaatgtcct gagcaatcac ctatgaactt gtttcaaatg catgatcaaa tgcaacctca | 1980 |
| caaccttggc tgagtcttga gactgaaaga tttagccata atgtaaactg cctcaaattg | 2040 |
| gactttgggc ataaaagaac ttttttatgc ttaccatctt ttttttttct ttaacagatt | 2100 |
| tgtatttaag aattgttttt aaaaaatttt aagatttaca caatgtttct ctgtaaatat | 2160 |
| tgccattaaa tgtaaataac tttaataaaa cgttttatagc agttacacag aatttcaatc | 2220 |
| ctagtatata gtacctagta ttataggtac tataaaccct aattttttt atttaagtac | 2280 |
| attttgcttt ttaaagttga tttttttcta ttgttttag aaaaaataaa ataactggca | 2340 |
| aatatatcat tgagccaaaa aaaaaaaaaa aaaaaaa | 2377 |

<210> SEQ ID NO 5
<211> LENGTH: 2098
<212> TYPE: DNA
<213> ORGANISM: Homo sapiens

<400> SEQUENCE: 5

| | |
|---|---|
| attataaatc tagagactcc aggattttaa cgttctgctg gactgagctg gttgcctcat | 60 |
| gttattatgc aggcaactca ctttatccca atttcttgat acttttcctt ctggaggtcc | 120 |
| tatttctcta acatcttcca gaaaagtctt aaagctgcct taacctttt tccagtccac | 180 |
| ctcttaaatt ttttcctcct cttcctctat actaacatga gtgtggatcc agcttgtccc | 240 |
| caaagcttgc cttgctttga agcatccgac tgtaaagaat cttcacctat gcctgtgatt | 300 |
| tgtgggcctg aagaaaacta tccatccttg caaatgtctt ctgctgagat gcctcacacg | 360 |
| gagactgtct ctcctcttcc ttcctccatg gatctgctta ttcaggacag ccctgattct | 420 |
| tccaccagtc ccaaaggcaa acaacccact tctgcagaga agagtgtcgc aaaaaaggaa | 480 |
| gacaaggtcc cggtcaagaa acagaagacc agaactgtgt tctcttccac ccagctgtgt | 540 |
| gtactcaatg atagatttca gagacagaaa tacctcagcc tccagcagat gcaagaactc | 600 |
| tccaacatcc tgaacctcag ctacaaacag gtgaagacct ggttccagaa ccagagaatg | 660 |
| aaatctaaga ggtggcagaa aaacaactgg ccgaagaata gcaatggtgt gacgcagaag | 720 |
| gcctcagcac ctacctaccc cagcctttac tcttcctacc accagggatg cctggtgaac | 780 |
| ccgactggga accttccaat gtggagcaac cagacctgga acaattcaac ctggagcaac | 840 |
| cagacccaga catccagtc ctggagcaac cactcctgga acactcagac ctggtgcacc | 900 |
| caatcctgga acaatcaggc ctggaacagt cccttctata actgtggaga ggaatctctg | 960 |

```
cagtcctgca tgcagttcca gccaaattct cctgccagtg acttggaggc tgccttggaa    1020
gctgctgggg aaggccttaa tgtaatacag cagaccacta ggtatttag tactccacaa    1080 accatggatt tattcctaaa ctactccatg aacatgcaac ctgaagacgt gtgaagatga    1140
gtgaaactga tattactcaa tttcagtctg acactggct gaatccttcc tctcccctcc    1200
tcccatccct cataggattt ttcttgtttg aaaccacgt gttctggttt ccatgatgcc    1260
catccagtca atctcatgga gggtggagta tggttggagc taatcagcg aggtttcttt    1320 tttttttttt ttcctattgg atcttcctgg agaaaatact ttttttttt ttttttttga    1380 aacggagtct tgctctgtcg cccaggctgg agtgcagtgg cgcggtcttg gctcactgca    1440
agctccgtct cccgggttca cgccattctc ctgcctcagc ctcccgagca gctgggacta    1500
caggcgcccg ccacctcgcc cggctaatat tttgtatttt tagtagagac ggggtttcac    1560
tgtgttagcc aggatggtct cgatctcctg accttgtgat ccacccgcct cggcctccct    1620
aacagctggg atttacaggc gtgagccacc gcgccctgcc tagaaaagac attttaataa    1680
ccttggctgc cgtctctggc tatagataag tagatctaat actagtttgg atatctttag    1740
ggtttagaat ctaacctcaa gaataagaaa tacaagtaca aattggtgat gaagatgtat    1800
tcgtattgtt tgggattggg aggctttgct tattttttaa aaactattga ggtaaagggt    1860
taagctgtaa catacttaat tgatttctta ccgttttgg ctctgttttg ctatatcccc    1920
taatttgttg gttgtgctaa tctttgtaga aagaggtctc gtatttgctg catcgtaatg    1980
acatgagtac tgctttagtt ggtttaagtt caaatgaatg aaacaactat ttttccttta    2040
gttgatttta ccctgatttc accgagtgtt tcaatgagta aatatacagc ttaaacat     2098

<210> SEQ ID NO 6
<211> LENGTH: 4014
<212> TYPE: DNA
<213> ORGANISM: Homo sapiens

<400> SEQUENCE: 6
gtgcggggga agatgtagca gcttcttctc cgaaccaacc ctttgccttc ggacttctcc      60 gggggccagca gccgcccgac caggggcccg ggccacggg ctcagccgac gaccatgggc     120
tccgtgtcca accagcagtt tgcaggtggc tgcgccaagg cggcagaaga ggcgcccgag     180
gaggcgccgg aggacgcggc ccgggcgcg gacgagcctc agctgctgca cggtgcgggc     240
atctgtaagt ggttcaacgt gcgcatgggg ttcggcttcc tgtccatgac cgcccgcgcc     300
ggggtcgcgc tcgacccccc agtggatgtc tttgtgcacc agagtaagct gcacatggaa     360
gggttccgga gcttgaagga gggtgaggca gtggagttca cctttaagaa gtcagccaag     420
ggtctggaat ccatccgtgt caccggacct ggtgagtat tctgtattgg gagtgagagg     480
cggccaaaag gaaagagcat gcagaagcgc agatcaaaag gagacaggtg ctacaactgt     540
ggaggtctag atcatcatgc caaggaatgc aagctgccac cccagcccaa gaagtgccac     600
ttctgccaga gcatcagcca tatggtagcc tcatgtccgc tgaaggccca gcagggccct     660
agtgcacagg gaaagccaac ctactttcga gaggaagaag aagaaatcca cagccctacc     720
ctgctcccgg aggcacagaa ttgagccaca atgggtgggg ctattctttt gctatcagg     780 aagttttgag gagcaggcag agtggagaaa gtgggaatag ggtgcattgg ggctagttgg     840
cactgccatg tatctcaggc ttgggttcac accatcaccc tttcttccct ctaggtgggg     900
ggaaagggtg agtcaaagga actccaacca tgctctgtcc aaatgcaagt gagggttctg     960
```

```
ggggcaacca ggagggggga atcacccctac aacctgcata ctttgagtct ccatccccag    1020
aatttccagc ttttgaaagt ggcctggata gggaagttgt tttccttta aagaaggata      1080 tataataatt cccatgccag agtgaaatga ttaagtataa gaccagattc atggagccaa    1140
gccactacat tctgtggaag gagatctctc aggagtaagc attgttttt ttcacatct      1200 tgtatcctca tacccacttt tgggataggg tgctggcagc tgtcccaagc aatgggtaat    1260
gatgatggca aaaagggtgt ttgggggaac agctgcagac ctgctgctct atgctcaccc    1320 ccgcccatt ctgggccaat gtgattttat ttatttgctc ccttggatac tgcaccttgg     1380
gtcccacttt ctccaggatg ccaactgcac tagctgtgtg cgaatgacgt atcttgtgca    1440
ttttaacttt ttttccttaa tataaatatt ctggttttgt atttttgtat attttaatct    1500
aaggccctca tttcctgcac tgtgttctca ggtacatgag caatctcagg atagccagc    1560 agcagctcca ggtctgcgca gcaggaatta cttttttgttg ttttttgccac cgtggagagc  1620 aactatttgg agtgcacagc ctattgaact acctcatttt tgccaataag agctggcttt    1680
tctgccatag tgtcctcttg aaaccccctc tgccttgaaa atgttttatg ggagactagg    1740
ttttaactgg gtggcccccat gacttgattg ccttctactg gaagattggg aattagtcta   1800
aacaggaaat ggtggtacac agaggctagg agaggctggg cccggtgaaa aggccagaga    1860
gcaagccaag attaggtgag ggttgtctaa tcctatggca caggacgtgc tttacatctc    1920
cagatctgtt cttcaccaga ttaggttagg cctaccatgt gccacagggt gtgtgtgtgt    1980
ttgtaaaact agagttgcta aggataagtt taaagaccaa taccccgta cttaatcctg     2040 tgctgtcgag ggatggatat atgaagtaag gtgagatcct taacctttca aaattttcgg    2100
gttccaggga gacacacaag cgagggtttt gtggtgcctg gagcctgtgt cctgccctgc    2160
tacagtagtg attaatagtg tcatggtagc taaaggagaa aaaggggggtt tcgtttacac   2220 gctgtgagat caccgcaaac ctaccttact gtgttgaaac gggacaaatg caatagaacg    2280
cattgggtgg tgtgtgtctg atcctgggtt cttgtctccc ctaaatgctg ccccccaagt    2340
tactgtattt gtctgggctt tgtaggactt cactacgttg attgctaggt ggcctagttt    2400
gtgtaaatat aatgtattgg tcttttctccg tgttctttgg gggttttgtt tacaaacttc   2460
tttttgtatt gagagaaaaa tagccaaagc atctttgaca gaaggttctg caccaggcaa    2520
aaagatctga aacattagtt tggggggccc tcttcttaaa gtggggatct tgaaccatcc    2580
tttcttttgt attcccccttc ccctattacc tattagacca gatcttctgt cctaaaaact   2640
tgtcttctac cctgccctct tttctgttca ccccccaaaag aaaacttaca cacccacaca   2700
catacacatt tcatgcttgg agtgtctcca caactcttaa atgatgtatg caaaaatact    2760
gaagctagga aaaccctcca tcccttgttc ccaacctcct aagtcaagac cattaccatt    2820
tctttctttc tttttttttt tttttaaaa tggagtctca ctgtgtcacc caggctggag    2880
tgcagtggca tgatcggctc actgcagcct ctgcctcttg ggttcaagtg attctcctgc    2940
ctcagcctcc tgagtagctg ggattcagg cacccgccac actcagctaa ttttttgtatt    3000 tttagtagag acggggtttc accatgttgt ccaggctggt ctggaactcc tgacctcagg    3060
tgatctgccc accttggctt cccaaagtgc tgggattaca ggcatgagcc accatgctgg    3120
gccaaccatt tcttggtgta ttcatgccaa acacttaaga cactgctgta gcccaggcgc    3180
ggtggctcac acctgtaatc ccagcacttt ggaaggctga ggcgggcgga tcacaaggtc    3240
acgagttcaa aactatcctg gccaacacag tgaaaccccg tctctactaa aatcaaaaaa    3300
aattagccgg gtgtggtggt gcatgccttt agtcctagct attcaggagg ctgaggcagg    3360
```

```
ggaatcgctt gaacccgaga ggcagaggtt gcagtgagct gagatcgcac cactgcactc   3420
cagcctggtt acagagcaag actctgtctc aaacaaaaca aaacaaaaca aaaacacact   3480
actgtatttt ggatggatca aacctcctta attttaattt ctaatcctaa agtaaagaga   3540
tgcaattggg ggccttccat gtagaaagtg gggtcaggag gccaagaaag gaatatgaa    3600 tgtatatcca agtcactcag gaactttat gcaggtgcta gaaactttat gtcaaagtgg    3660
ccacaagatt gtttaatagg agacgaacga atgtaactcc atgtttactg ctaaaaacca   3720
aagctttgtg taaaatcttg aatttatggg gcgggagggt aggaaagcct gtacctgtct   3780 gttttttttcc tgatcctttt ccctcattcc tgaactgcag gagactgagc ccctttgggc  3840
tttggtgacc ccatcactgg ggtgtgttta tttgatggtt gattttgctg tactgggtac   3900
ttcctttccc attttctaat cattttttaa cacaagctga ctcttccctt ccttctcct    3960 ttccctggga aaatacaatg aataaataaa gacttattgg tacgcaaact gtca         4014

<210> SEQ ID NO 7
<211> LENGTH: 1823
<212> TYPE: DNA
<213> ORGANISM: Homo sapiens

<400> SEQUENCE: 7
gagaagctag gggtgaggaa gccctggggc gctgccgccg ctttccttaa ccacaaatca     60
ggccggacag gagagggagg ggtgggggac agtgggtggg cattcagact gccagcactt    120
tgctatctac agccggggct cccgagcggc agaaagttcc ggccactctc tgccgcttgg    180
gttgggcgaa gccaggaccg tgccgcgcca ccgccaggat atggagctac tgtcgccacc    240
gctccgcgac gtagacctga cggccccga cggctctctc tgctcctttg ccacaacgga    300
cgacttctat gacgacccgt gtttcgactc cccggacctg cgcttcttcg aagacctgga   360
cccgcgcctg atgcacgtgg gcgcgctcct gaaacccgaa gagcactcgc acttccccgc   420
ggcggtgcac ccggccccgg gcgcacgtga ggacgagcat gtgcgcgcgc ccagcgggca   480
ccaccaggcg ggccgctgcc tactgtgggc ctgcaaggcg tgcaagcgca agaccaccaa    540
cgccgaccgc cgcaaggccg ccaccatgcg cgagcggcgc cgcctgagca agtaaatga    600 ggcctttgag acactcaagc gctgcacgtc gagcaatcca aaccagcggt tgcccaaggt    660
ggagatcctc cgcaacgcca tccgctatat cgagggcctg caggtctgc tgcgcgacca    720 ggacgccgcg ccccctggcg ccgcagccgc cttctatgcg ccgggccgc tgcccccggg    780 ccgcggcggc gagcactaca gcggcgactc cgacgcgtcc agcccgcgct caactgctc    840 cgacggcatg atggactaca gcggccccc gagcggcgcc cggcggcgga actgctacga   900
aggcgcctac tacaacgagg cgcccagcga acccaggccc gggaagagtg cggcggtgtc    960
gagcctagac tgcctgtcca gcatcgtgga gcgcatctcc accgagagcc ctgcggcgcc    1020
cgccctcctg ctggcggacg tgccttctga gtcgcctccg cgcaggcaag aggctgccgc    1080
ccccagcgag ggagagagca gcggcgaccc cacccagtca ccggacgccg cccgcagtg    1140 ccctgcgggt gcgaacccca acccgatata ccaggtgctc tgaggggatg gtggccgccc   1200
acccgcccga gggatggtgc ccctaggtgtc cctcgcgccc aaaagattga acttaaatgc    1260
ccccctccca acagcgcttt aaaagcgacc tctcttgagg taggagaggc gggagaactg    1320
aagtttccgc cccgcccca cagggcaagg acacagcgcg gttttttcca cgcagcaccc    1380
ttctcggaga cccattgcga tggccgctcc gtgttcctcg gtgggccaga gctgaacctt   1440
```

| | |
|---|---:|
| gaggggctag gttcagcttt ctcgcgccct cccccatggg ggtgagaccc tcgcagacct | 1500 |
| aagccctgcc ccgggatgca ccggttattt gggggggcgt gagacccagt gcactccggt | 1560 |
| cccaaatgta gcaggtgtaa ccgtaaccca ccccaaccc gtttcccggt tcaggaccac | 1620 |
| ttttttgtaat acttttgtaa tctattcctg taaataagag ttgctttgcc agagcaggag | 1680 |
| cccctggggc tgtatttatc tctgaggcat ggtgtgtggt gctacaggga atttgtacgt | 1740 |
| ttataccgca ggcgggcgag ccgcgggcgc tcgctcaggt gatcaaaata aaggcgctaa | 1800 |
| tttataaaaa aaaaaaaaaa aaa | 1823 |

<210> SEQ ID NO 8
<211> LENGTH: 2490
<212> TYPE: DNA
<213> ORGANISM: Homo sapiens

<400> SEQUENCE: 8

| | |
|---|---:|
| agcactctct cacttctggc cagggaacgt ggaaggcgca ccgacaggga tccggccagg | 60 |
| gagggcgagt gaaagaagga aatcagaaag gaagggagtt aacaaaataa taaaaacagc | 120 |
| ctgagccacg gctggagaga ccgagacccg gcgcaagaga gcgcagcctt agtaggagag | 180 |
| gaacgcgaga cgcggcagag cgcgttcagc actgactttt gctgctgctt ctgctttttt | 240 |
| ttttcttaga aacaagaagg cgccagcggc agcctcacac gcgagcgcca cgcgaggctc | 300 |
| ccgaagccaa cccgcgaagg gaggagggga gggaggagga ggcggcgtgc agggaggaga | 360 |
| aaaagcattt tcacttttt tgctcccact ctaagaagtc tcccggggat tttgtatata | 420 |
| ttttttaact tccgtcaggg ctcccgcttc atatttcctt ttctttccct ctctgttcct | 480 |
| gcacccaagt tctctctgtg tcccctcgc gggccccgca cctcgcgtcc cggatcgctc | 540 |
| tgattccgcg actccttggc cgccgctgcg catggaaagc tctgccaaga tggagagcgg | 600 |
| cggcgccggc cagcagcccc agccgcagcc ccagcagccc ttcctgccgc ccgcagcctg | 660 |
| tttctttgcc acgccgcag ccgcggcggc cgcagccgcc gcagcggcag cgcagagcgc | 720 |
| gcagcagcag cagcagcagc agcagcagca gcagcaggcg ccgcagctga ccggcggc | 780 |
| cgacggccag ccctcagggg gcggtcacaa gtcagcgccc aagcaagtca agcgacagcg | 840 |
| ctcgtcttcg cccgaactga tgcgctgcaa acgccggctc aacttcagcg ctttggcta | 900 |
| cagcctgccg cagcagcagc cggccgccgt ggcgcgccgc aacgagcgcg agcgcaaccg | 960 |
| cgtcaagttg gtcaacctgg ctttgccac ccttcgggag cacgtcccca acggcgcggc | 1020 |
| caacaagaag atgagtaagg tggagacact gcgctcggcg gtcgagtaca tccgcgcgct | 1080 |
| gcagcagctg ctggacgagc atgacgcggt gagcgccgcc ttccaggcag gcgtcctgtc | 1140 |
| gcccaccatc tcccccaact actccaacga cttgaactcc atggccggct cgccggtctc | 1200 |
| atcctactcg tcggacgagg gctcttacga cccgctcagc cccgaggagc aggagcttct | 1260 |
| cgacttcacc aactggttct gaggggctcg gcctggtcag gccctggtgc gaatggactt | 1320 |
| tggaagcagg gtgatcgcac aacctgcatc tttagtgctt tcttgtcagt ggcgttggga | 1380 |
| gggggagaaa aggaaaagaa aaaaaaaga agaagaagaa gaaagagaa gaagaaaaaa | 1440 |
| acgaaaacag tcaaccaacc ccatcgccaa ctaagcgagg catgcctgag agacatggct | 1500 |
| ttcagaaaac gggaagcgct cagaacagta tctttgcact ccaatcattc acggagatat | 1560 |
| gaagagcaac tgggacctga gtcaatgcgc aaaatgcagc ttgtgtgcaa aagcagtggg | 1620 |
| ctcctggcag aagggagcag cacacgcgtt atagtaactc ccatcacctc taacacgcac | 1680 |
| agctgaaagt tcttgctcgg gtcccttcac ctcctcgccc tttcttaaag tgcagttctt | 1740 |

```
agccctctag aaacgagttg gtgtctttcg tctcagtagc ccccacccca ataagctgta    1800
gacattggtt tacagtgaaa ctatgctatt ctcagcccct tgaaactctg cttctcctcc    1860
agggcccgat tcccaaaccc catggcttcc ctcacactgt cttttctacc attttcatta    1920
tagaatgctt ccaatctttt gtgaattttt tattataaaa aatctatttg tatctatcct    1980
aaccagttcg gggatatatt aagatatttt tgtacataag agagaaagag agagaaaaat    2040
ttatagaagt tttgtacaaa tggtttaaaa tgtgtatatc ttgatacttt aacatgtaat    2100
gctattacct ctgcatattt tagatgtgta gttcaccttaa caactgcaat tttccctatg    2160
tggttttgta aagaactctc ctcataggtg agatcaagag gccaccagtt gtacttcagc    2220
accaatgtgt cttactttat agaaatgttg ttaatgtatt aatgatgtta ttaaatactg    2280
ttcaagaaga acaaagttta tgcagctact gtccaaactc aaagtggcag ccagttggtt    2340
ttgataggtt gccttttgga gatttctatt actgcctttt ttttcttac tgttttatta     2400 caaacttaca aaaatatgta taaccctgtt ttatacaaac tagtttcgta ataaaacttt    2460 ttccttttt taaaatgaaa ataaaaaaaa                                      2490

<210> SEQ ID NO 9
<211> LENGTH: 1426
<212> TYPE: DNA
<213> ORGANISM: Homo sapiens

<400> SEQUENCE: 9
gactatctcc cagcggcagg cccttcgata aaatcaggaa cttgtgctgg ccctgcaatg      60
tcaagggagg gggctcaccc agggctcctg tagctcaggg ggcaggcctg agccctgcac     120
ccgccccacg accgtccagc ccctgacggg gcaccccatc ctgaggggct ctgcattggc     180
ccccaccgag gcagggatc tgaccgactc ggagcccggc tggatgttac aggcgtgcaa      240
aatggaaggg tttcccctcg tcccccctca gccatcagaa gacctggtgc cctatgacac     300
ggatctatac caacgccaaa cgcacgagta ttacccctat ctcagcagtg atggggagag     360
ccatagcgac cattactggg acttccaccc ccaccgtgt cacagcgagt tcgagagctt      420
cgccgagaac aacttcacgg agctccagag cgtgcagccc ccgcagctgc agcagctcta     480
ccgccacatg gagctggagc agatgcacgt cctcgatacc cccatggtgc accccatcc     540 cagtcttggc caccaggtct cctacctgcc ccggatgtgc ctccagtacc catccctgtc     600
cccagcccag cccagctcag atgaggagga gggcgagcgg cagagccccc cactggaggt    660
gtctgacggc gaggcggatg gcctggagcc cgggcctggg ctcctgcctg gggagacagg    720
cagcaagaag aagatccgcc tgtaccagtt cctgttggac ctgctccgca gcggcgacat    780
gaaggacagc atctggtggg tggacaagga caagggcacc ttccagttct cgtccaagca    840
caaggaggcg ctggcgcacc gctggggcat ccagaagggc aaccgcaaga gatgacccta    900
ccagaagatg cgcgcgcgc tgcgcaacta cggcaagacg ggcgaggtca agaaggtgaa    960
gaagaagctc acctaccagt tcagcggcga agtgctgggc cgcggggcc tggccgagcg    1020 gcgccacccg ccccactgag cccgcagccc ccgccgggcc ccgccaggcc tccccgctgg    1080
ccatagcatt aagccctcgc ccggcccgga cacaggagg acgctcccgg ggcccagagg    1140
caggactgtg gcgggccggg cctcgcctca cccgcccct ccccccactc caggccccct    1200
ccacatcccg cttcgcctcc ctccaggact ccaccccggc tcccgacgc cagctgggcg    1260 tcagaccccca ccggggcaac cttgcagagg acgacccggg gtactgcctt gggagtctca    1320
```

| | |
|---|---|
| agtccgtatg taaatcagat ctcccctctc acccctccca cccattaacc tcctcccaaa | 1380 |
| aaacaagtaa agttattctc aatccatcaa aaaaaaaaaa aaaaaa | 1426 |

<210> SEQ ID NO 10
<211> LENGTH: 2591
<212> TYPE: DNA
<213> ORGANISM: Homo sapiens

<400> SEQUENCE: 10

| | |
|---|---|
| cggaggtgcg cgggcgcggg cgagcagggt ctccgggtgg gcggcggcga cgcccgcgc | 60 |
| aggctggagg ccgccgaggc tcgccatgcc gggagaactc taactccccc atggagtcgg | 120 |
| ccgacttcta cgaggcggag ccgcggcccc cgatgagcag ccacctgcag agcccccgc | 180 |
| acgcgcccag cagcgccgcc ttcggctttc ccggggcgc gggccccgcg cagcctcccg | 240 |
| ccccacctgc cgccccggag ccgctgggcg gcatctgcga gcacgagacg tccatcgaca | 300 |
| tcagcgccta catcgacccg gccgccttca cgacgagtt cctggccgac ctgttccagc | 360 |
| acagccggca gcaggagaag gccaaggcgg ccgtgggccc cacgggcggc ggcggcggcg | 420 |
| gcgactttga ctaccggggc gcgcccgcgg gccccggcgg cgccgtcatg cccggggag | 480 |
| cgcacgggcc cccgcccggc tacgctgcg cggccgccgg ctacctggac ggcaggctgg | 540 |
| agccctgta cgagcgcgtc ggggcgccgg cgctgcggcc gctggtgatc aagcaggagc | 600 |
| cccgcgagga ggatgaagcc aagcagctgg cgctggccgg cctcttccct taccagccgc | 660 |
| cgccgccgcc gccgcctcg cacccgcacc cgcacccgcc gccgcgcac ctggccgccc | 720 |
| cgcacctgca gttccagatc gcgcactgcg gccagaccac catgcacctg cagcccggtc | 780 |
| accccacgcc gccgccacg cccgtgccca gcccgcaccc cgcgcccgcg ctcggtgccg | 840 |
| ccggcctgcc gggccctggc agcgcgctca agggggctggg cgccgcgcac cccgacctcc | 900 |
| gcgcgagtgg cggcagcggc gcgggcaagg ccaagaagtc ggtggacaag aacagcaacg | 960 |
| agtaccgggt gcgcgcgag cgcaacaaca tcgcggtgcg caagagccgc gacaaggcca | 1020 |
| agcagcgcaa cgtggagacg cagcagaagg tgctggagct gaccagtgac aatgaccgcc | 1080 |
| tgcgcaagcg ggtggaacag ctgagccgcg aactggacac gctgcgggc atcttccgcc | 1140 |
| agctgccaga gagctccttg gtcaaggcca tgggcaactg cgcgtgaggc gcgcggctgt | 1200 |
| gggaccgccc tggccagcc tccggcgggg acccagggga tggtttgggg tcgccggatc | 1260 |
| tcgaggcttg cccgagccgt gcgagccagg actaggagat tccggtgcct cctgaaagcc | 1320 |
| tggcctgctc cgcgtgtccc ctcccttcct ctgcgccgga cttggtgcgt ctaagatgag | 1380 |
| ggggccaggc ggtggcttct ccctgcgagg aggggagaat tcttggggct gagctgggag | 1440 |
| cccggcaact ctagtattta ggataaccttt gtgccttgga aatgcaaact caccgctcca | 1500 |
| atgcctactg agtaggggga gcaaatcgtg ccttgtcatt ttatttggag gtttcctgcc | 1560 |
| tccttcccga ggctacagca gacccccatg agagaaggag gggagcaggc ccgtggcagg | 1620 |
| aggagggctc agggagctga gatcccgaca agcccgccag ccccagccgc tcctccacgc | 1680 |
| ctgtccttag aaaggggtgg aaacataggg acttggggct tggaacctaa ggttgttccc | 1740 |
| ctagttctac atgaaggtgg agggtctcta gttccacgcc tctcccacct ccctccgcac | 1800 |
| acaccccacc ccagcctgct ataggctggg cttcccttg ggcggaact cactgcgatg | 1860 |
| ggggtcacca ggtgaccagt gggagccccc accccgagtc acaccagaaa gctaggtcgt | 1920 |
| gggtcagctc tgaggatgta tacccctggt gggagaggga gacctagaga tctggctgtg | 1980 |
| gggcgggcat gggggtgaa gggccactgg gaccctcagc cttgtttgta ctgtatgcct | 2040 |

| | |
|---|---:|
| tcagcattgc ctaggaacac gaagcacgat cagtccatcc cagagggacc ggagttatga | 2100 |
| caagctttcc aaatattttg ctttatcagc cgatatcaac acttgtatct ggcctctgtg | 2160 |
| ccccagcagt gccttgtgca atgtgaatgt gcgcgtctct gctaaaccac cattttattt | 2220 |
| ggttttgtt ttgttttggt tttgctcgga tacttgccaa aatgagactc tccgtcggca | 2280 |
| gctgggggaa gggtctgaga ctcccttcc ttttggtttt gggattactt ttgatcctgg | 2340 |
| gggaccaatg aggtgagggg ggttctcctt tgccctcagc tttccccagc ccctccggcc | 2400 |
| tgggctgccc acaaggcttg tcccccagag gccctggctc ctggtcggga agggaggtgg | 2460 |
| cctcccgcca acgcatcact ggggctggga cagggaagg acggcttggt tctcttcttt | 2520 |
| tggggagaac gtagagtctc actctagatg ttttatgtat tatatctata atataaacat | 2580 |
| atcaaagtca a | 2591 |

<210> SEQ ID NO 11
<211> LENGTH: 1837
<212> TYPE: DNA
<213> ORGANISM: Homo sapiens

<400> SEQUENCE: 11

| | |
|---|---:|
| gagccgcgca cgggactggg aaggggaccc acccgagggt ccagccacca gcccctcac | 60 |
| taatagcggc caccccggca gcggcggcag cagcagcagc gacgcagcgg cgacagctca | 120 |
| gagcagggag gccgcgccac ctgcgggccg gccggagcgg gcagcccag gcccctccc | 180 |
| cgggcacccg cgttcatgca acgcctggtg gcctgggacc cagcatgtct ccccctgccg | 240 |
| ccgccgccgc ctgcctttaa atccatggaa gtggccaact tctactacga ggcggactgc | 300 |
| ttggctgctg cgtacggcgg caaggcggcc cccgcggcgc ccccgcggc cagacccggg | 360 |
| ccgcgccccc ccgccggcga gctgggcagc atcggcgacc acgagcgcgc catcgacttc | 420 |
| agcccgtacc tggagccgct gggcgcgccc caggcccggg cgcccgccac ggccacggac | 480 |
| accttcgagg cggctccgcc cgcgcccgcc cccgcgcccg cctcctccgg gcagcaccac | 540 |
| gacttcctct ccgacctctt ctccgacgac tacgggggca agaactgcaa gaagccggcc | 600 |
| gagtacggct acgtgagcct ggggcgcgcctg ggggccgcca agggcgcgct gcaccccggc | 660 |
| tgcttcgcgc ccctgcaccc accgccccg ccgccgccgc cgcccgccga gctcaaggcg | 720 |
| gagccgggct tcgagcccgc ggactgcaag cggaaggagg aggccggggc gccgggcggc | 780 |
| ggcgcaggca tggcggcggg cttcccgtac gcgctgcgcg cttacctcgg ctaccaggcg | 840 |
| gtgccgagcg gcagcagcgg gagcctctcc acgtcctcct cgtccagccc gcccggcacg | 900 |
| ccgagccccg ctgacgccaa ggcgccccg accgcctgct acgcggggc gcgccggcg | 960 |
| ccctcgcagg tcaagagcaa ggccaagaag accgtggaca gcacagcga cgagtacaag | 1020 |
| atccggcgcg agcgcaacaa catcgccgtg cgcaagagcc gcgacaaggc caagatgcgc | 1080 |
| aacctggaga cgcagcacaa ggtcctggag ctcacgccg agaacgagcg gctgcagaag | 1140 |
| aaggtggagc agctgtcgcg cgagctcagc accctgcgga cttgttcaa gcagctgccc | 1200 |
| gagcccctgc tcgcctcctc cggccactgc tagcgcggcc ccgcgcgcg tcccctgcc | 1260 |
| ggccggggct gagactccgg ggagcccg cgccgcgcg ctcgccccg ccccggcgg | 1320 |
| cgccggcaaa actttggcac tgggcactt ggcagcgcgg ggagcccgtc ggtaattta | 1380 |
| atatttatt atatatat atctatattt ttgtccaaac caaccgcaca tgcagatggg | 1440 |
| gctcccgccc gtggtgttat ttaaagaaga aacgtctatg tgtacagatg aatgataaac | 1500 |

| | |
|---|---|
| tctctgcttc tccctctgcc cctctccagg cgccggcggg cgggccggtt tcgaagttga | 1560 |
| tgcaatcggt ttaaacatgg ctgaacgcgt gtgtacacgg gactgacgca acccacgtgt | 1620 |
| aactgtcagc cgggccctga gtaatcgctt aaagatgttc ctacgggctt gttgctgttg | 1680 |
| atgttttgtt ttgttttgtt ttttggtctt tttttgtatt ataaaaaata atctatttct | 1740 |
| atgagaaaag aggcgtctgt atattttggg aatcttttcc gtttcaagca ttaagaacac | 1800 |
| ttttaataaa cttttttttg agaatggtta caaagcc | 1837 |

<210> SEQ ID NO 12
<211> LENGTH: 2098
<212> TYPE: DNA
<213> ORGANISM: Homo sapiens

<400> SEQUENCE: 12

| | |
|---|---|
| attataaatc tagagactcc aggattttaa cgttctgctg gactgagctg gttgcctcat | 60 |
| gttattatgc aggcaactca ctttatccca atttcttgat acttttcctt ctggaggtcc | 120 |
| tatttctcta acatcttcca gaaaagtctt aaagctgcct taaccttttt tccagtccac | 180 |
| ctcttaaatt ttttcctcct cttcctctat actaacatga gtgtggatcc agcttgtccc | 240 |
| caaagcttgc cttgctttga agcatccgac tgtaaagaat cttcacctat gcctgtgatt | 300 |
| tgtgggcctg aagaaaacta tccatccttg caaatgtctt ctgctgagat gcctcacacg | 360 |
| gagactgtct ctcctcttcc ttcctccatg gatctgctta tcaggacag ccctgattct | 420 |
| tccaccagtc ccaaaggcaa caacccact tctgcagaga agagtgtcgc aaaaaaggaa | 480 |
| gacaaggtcc cggtcaagaa acagaagacc agaactgtgt tctcttccac ccagctgtgt | 540 |
| gtactcaatg atagatttca gagacagaaa tacctcagcc tccagcagat gcaagaactc | 600 |
| tccaacatcc tgaacctcag ctacaaacag gtgaagacct ggttccagaa ccagagaatg | 660 |
| aaatctaaga ggtggcagaa aaacaactgg ccgaagaata gcaatggtgt gacgcagaag | 720 |
| gcctcagcac ctacctaccc cagcctttac tcttcctacc accagggatg cctggtgaac | 780 |
| ccgactggga accttccaat gtggagcaac cagacctgga caattcaac ctggagcaac | 840 |
| cagacccaga acatccagtc ctggagcaac cactcctgga cactcagac ctggtgcacc | 900 |
| caatcctgga caatcaggc ctggaacagt cccttctata actgtggaga ggaatctctg | 960 |
| cagtcctgca tgcagttcca gccaaattct cctgccagtg acttggaggc tgccttggaa | 1020 |
| gctgctgggg aaggccttaa tgtaatacag cagaccacta ggtattttag tactccacaa | 1080 |
| accatggatt tattcctaaa ctactccatg aacatgcaac ctgaagacgt gtgaagatga | 1140 |
| gtgaaactga tattactcaa tttcagtctg gacactggct gaatccttcc tctcccctcc | 1200 |
| tcccatccct cataggattt tcttgtttg gaaccacgt gttctggttt ccatgatgcc | 1260 |
| catccagtca atctcatgga gggtggagta tggttggagc ctaatcagcg aggtttcttt | 1320 |
| tttttttttt ttcctattgg atcttcctgg agaaaatact tttttttttt tttttttga | 1380 |
| aacggagtct tgctctgtcg cccaggctgg agtgcagtgg cgcggtcttg ctcactgca | 1440 |
| agctccgtct cccgggttca cgccattctc ctgcctcagc ctcccgagca gctgggacta | 1500 |
| caggcgcccg ccacctcgcc cggctaatat tttgtatttt tagtagagac ggggtttcac | 1560 |
| tgtgttagcc aggatggtct cgatctcctg accttgtgat ccacccgcct cggcctccct | 1620 |
| aacagctggg atttacaggc gtgagccacc gcgcccgcc tagaaaagac atttaataa | 1680 |
| ccttggctgc cgtctctggc tatagataag tagatctaat actagtttgg atatcttag | 1740 |
| ggtttagaat ctaacctcaa gaataagaaa tacaagtaca aattggtgat gaagatgtat | 1800 |

```
tcgtattgtt tgggattggg aggctttgct tattttttaa aaactattga ggtaaagggt    1860
taagctgtaa catacttaat tgatttctta ccgttttggg ctctgttttg ctatatcccc    1920
taatttgttg gttgtgctaa tctttgtaga aagaggtctc gtatttgctg catcgtaatg    1980
acatgagtac tgctttagtt ggtttaagtt caaatgaatg aaacaactat ttttccttta    2040
gttgatttta ccctgatttc accgagtgtt tcaatgagta aatatacagc ttaaacat     2098

<210> SEQ ID NO 13
<211> LENGTH: 2573
<212> TYPE: DNA
<213> ORGANISM: Homo sapiens

<400> SEQUENCE: 13
gggtggcgcc gggagtggga acgccacaca gtgccaaatc cccggctcca gctcccgact     60
cccggctccc ggctcccggc tcccggtgcc caatcccggg ccgcagccat gaacggcgag    120
gagcagtact acgcggccac gcagctttac aaggacccat gcgcgttcca gcgaggcccg    180
gcgccggagt tcagcgccag ccccctgcg tgcctgtaca tgggccgcca gccccgccg     240 ccgccgccgc accgttccc tggcgccctg ggcgcgctgg agcagggcag cccccggac    300 atctccccgt acgaggtgcc cccctcgcc gacgaccccg cggtggcgca ccttcaccac    360
cacctcccgg ctcagctcgc gctccccac ccgcccgccg ggcccttccc ggagggagcc    420
gagccgggcg tcctggagga gcccaaccgc gtccagctgc ctttcccatg gatgaagtct    480
accaaagctc acgcgtggaa aggccagtgg gcaggcggcg cctacgctgc ggagccggag    540
gagaacaagc ggacgcgcac ggcctacacg cgcgcacagc tgctagagct ggagaaggag    600
ttcctattca acaagtacat ctcacggccg cgccgggtgg agctggctgt catgttgaac    660
ttgaccgaga gacacatcaa gatctggttc caaaaccgcc gcatgaagtg gaaaaaggag    720
gaggacaaga gcgcggcgg cgggacagct gtcggggtg gcggggtcgc ggagcctgag    780
caggactgcg ccgtgacctc cggcgaggag cttctggcgc tgccgccgcc gccgccccc    840 ggaggtgctg tgccgcccgc tgcccccgtt gccgcccgag agggccgcct gccgcctggc    900
cttagcgcgt cgccacagcc ctccagcgtc gcgcctcggc ggccgcagga accacgatga    960
gaggcaggag ctgctcctgg ctgaggggct tcaaccactc gccgaggagg agcagagggc   1020
ctaggaggac cccgggcgtg gaccaccgc cctggcagtt gaatgggcg gcaattgcgg    1080 ggcccacctt agaccgaagg ggaaaacccg ctctctcagg cgcatgtgcc agttggggcc   1140
ccgcgggtag atgccggcag gccttccgga agaaaaagag ccattggttt ttgtagtatt   1200
ggggccctct tttagtgata ctggattggc gttgtttgtg gctgttgcgc acatccctgc   1260
cctcctacag cactccacct tgggacctgt ttagagaagc cggctcttca agacaatgg    1320 aaactgtacc atacacattg gaaggctccc taacacacac agcggggaag ctgggccgag   1380
taccttaatc tgccataaag ccattcttac tcggcgacc cctttaagtt tagaaataat   1440
tgaaaggaaa tgtttgagtt ttcaaagatc ccgtgaaatt gatgccagtg gaatacagtg   1500
agtcctcctc ttcctcctcc tcctcttccc cctcccttc ctcctcctcc tcttcttttc    1560
cctcctcttc ctcttcctcc tgctctcctt tctcccccct cctctttcc ctcctcttcc    1620 tcttcctcct gctctccttt cctcccccte ctctttctcc tcctcctcct cttcttcccc    1680
ctcctctccc tcctcctctt cttccccctc ctctcccctcc tcctcttctt ctccctcctc   1740
ttcctcttcc tcctcttcca cgtgctctcc tttcctcccc ctcctcttgc tccccttctt    1800
```

| | | | | |
|---|---|---|---|---|
| ccccgtcctc | ttcctcctcc | tcctcttctt | ctccctcctc | ttcctcctcc tctttcttcc | 1860 |
| tgacctctt | ctttctcctc | ctcctccttc | tacctccct | tctcatccct cctcttcctc | 1920 |
| ttctctagct | gcacacttca | ctactgcaca | tcttataact | tgcaccccctt tcttctgagg | 1980 |
| aagagaacat | cttgcaaggc | agggcgagca | gcggcagggc | tggcttagga gcagtgcaag | 2040 |
| agtccctgtg | ctccagttcc | acactgctgg | cagggaaggc | aaggggggac gggcctggat | 2100 |
| ctggggtga | gggagaaaga | tggaccccctg | ggtgaccact | aaaccaaaga tattcggaac | 2160 |
| tttctattta | ggatgtggac | gtaattcctg | ttccgaggta | gaggctgtgc tgaagacaag | 2220 |
| cacagtggcc | tggtgcgcct | tggaaaccaa | caactattca | cgagccagta tgaccttcac | 2280 |
| atctttagaa | attatgaaaa | cgtatgtgat | tggagggttt | ggaaaaccag ttatcttatt | 2340 |
| taacatttta | aaaattacct | aacagttatt | tacaaacagg | tctgtgcatc ccaggtctgt | 2400 |
| cttcttttca | aggtctgggc | cttgtgctcg | ggttatgttt | gtgggaaatg cttaataaat | 2460 |
| actgataata | tgggaagaga | tgaaaactga | ttctcctcac | tttgtttcaa acctttctgg | 2520 |
| cagtgggatg | attcgaattc | acttttaaaa | ttaaattagc | gtgttttgtt ttg | 2573 |

<210> SEQ ID NO 14
<211> LENGTH: 1062
<212> TYPE: DNA
<213> ORGANISM: Homo sapiens

<400> SEQUENCE: 14

| | | | | |
|---|---|---|---|---|
| atggccgcgg | agctggcgat | gggcgccgag | ctgcccagca | gcccgctggc catcgagtac | 60 |
| gtcaacgact | cgacctgat | gaagttcgag | gtgaagaagg | agcctcccga ggccgagcgc | 120 |
| ttctgccacc | gctgccgcc | aggctcgctg | tcctcgacgc | cgctcagcac gccctgctcc | 180 |
| tccgtgccct | cctcgcccag | cttctgcgcg | cccagcccgg | gcaccggcgg cggcggcggc | 240 |
| gcggggggcg | gcggcggctc | gtctcaggcc | ggggcgccc | ccgggccgcc gagcggggc | 300 |
| cccgcgccg | tcggggcac | ctcggggaag | ccggcgctgg | aggatctgta ctggatgagc | 360 |
| ggctaccagc | atcacctcaa | ccccgaggcg | ctcaacctga | cgcccgagga cgcggtggag | 420 |
| gcgctcatcg | gcagcggcca | ccacggcgcg | caccacggcg | cgcaccaccc ggcggccgcc | 480 |
| gcagcctacg | aggcctttcg | cggcccgggc | ttcgcgggcg | gcggcggagc ggacgacatg | 540 |
| ggcgccggcc | accaccacgg | cgcgcaccac | gccgcccacc | atcaccacgc cgcccaccac | 600 |
| caccaccacc | accaccacca | ccatggcggc | gcgggacacg | gcggtggcgc gggccaccac | 660 |
| gtgcgcctgg | aggagcgctt | ctccgacgac | cagctggtgt | ccatgtcggt gcgcgagctg | 720 |
| aaccggcagc | tccgcggctt | cagcaaggag | gaggtcatcc | ggctcaagca gaagcggcgc | 780 |
| acgctcaaga | accgcggcta | cgcgcagtcc | tgccgcttca | gcgggtgca gcagcggcac | 840 |
| attctggaga | gcgagaagtg | ccaactccag | agccaggtgg | agcagctgaa gctggaggtg | 900 |
| gggcgcctgg | ccaaagagcg | ggacctgtac | aaggagaaat | acgagaagct ggcgggccgg | 960 |
| ggcggccccg | ggagcgcggg | cggggccggt | ttccgcgggg | agccttcgcc gccgcaggcc | 1020 |
| ggtcccggcg | gggccaaggg | cacggccgac | ttcttcctgt | ag | 1062 |

<210> SEQ ID NO 15
<211> LENGTH: 2193
<212> TYPE: DNA
<213> ORGANISM: Homo sapiens

<400> SEQUENCE: 15

| | | | | |
|---|---|---|---|---|
| cgggagccca | tggagcactg | tcctcagaga | tgcgcaggtt | aggctcactg tctaggccag | 60 |

```
gcccaccttta gtcactgtgg actggcaatg gaagctcttc ctggacacac ctgccctagc    120
cctcaccctg gggtggaaga gaaatgagct tggcttgcaa ctcagaccat tccacggagg    180
catcctccct tccctgggct ggtgaataaa agtttcctga ggtcaaggac ttccttttcc    240
ctgccaaaat ggtgtccaga actttgaggc cagaggtgat ccagtgattt gggagctgca    300
ggtcacacag gctgctcaga gggctgctga acaggatgtc ctcggacgac aggcacctgg    360
gctccagctg cggctccttc atcaagactg agccgtccag cccgtcctcg ggcattgatg    420
ccctcagcca ccacagcccc agtggctcgt ccgacgccag cggcggcttt ggcctggccc    480
tgggcaccca cgccaacggt ctggactcgc cacccatgtt tgcaggcgcc gggctgggag    540
gcaccccatg ccgcaagagc tacgaggact gtgccagcgg catcatggag gactcggcca    600
tcaagtgcga gtacatgctc aacgccatcc ccaagcgcct gtgcctcgtg tgcgggggaca    660
ttgcctctgg ctaccactac ggcgtggcct cctgcgaggc ttgcaaggcc ttcttcaaga    720
ggactatcca agggaacatt gagtacagct gcccggccac caacgagtgc gagatcacca    780
aacggaggcg caagtcctgc caggcctgcc gcttcatgaa atgcctcaaa gtgggatgc     840
tgaaggaagt gtgcgccctt gatcgagtgc gtggaggccg tcagaaatac aagcgacggc    900
tggactcaga gagcagccca tacctgagct tacaaatttc tccacctgct aaaaagccat    960
tgaccaagat tgtctcatac ctactggtgg ctgagccgga caagtctat gccatgcctc    1020
ccctggtat gcctgagggg gacatcaagg ccctgaccac tctctgtgac ctggcagacc    1080
gagagcttgt ggtcatcatt ggctgggcca agcacatccc aggcttctca agcctctccc    1140
tgggggacca tgatgagcctg ctgcagagtg cctggatgga atcctcatc ctgggcatcg    1200
tgtaccgctc gctgcccctat gacgacaagc tggtgtacgc tgaggactac atcatggatg    1260
aggagcactc ccgcctcgcg gggctgctgg agctctaccg ggccatcctg cagctggtac    1320
gcaggtacaa gaagctcaag gtggagaagg aggagtttgt gacgctcaag gccctggccc    1380
tcgccaactc cgattccatg tacatcgagg atctagaggc tgtccagaag ctgcaggacc    1440
tgctgcacga ggcactgcag gactacgagc tgagccagcg ccatgaggag ccctggagga    1500
cgggcaagct gctgctgaca ctgccgctgc tgcggcagac ggccgccaag gccgtgcagc    1560
acttctatag cgtcaaactg cagggcaaag tgcccatgca caaactcttc ctggagatgc    1620
tggaggccaa ggcctgggcc agggctgact cccttcagga gtggaggcca ctggagcaag    1680
tgccctctcc cctccaccga gccaccaaga ggcagcatgt gcatttccta actcccttgc    1740
cccctccccc atctgtggcc tgggtgggca ctgctcaggc tggataccac ctggaggttt    1800
tccttccgca gagggcaggt tggccaagag cagcttagag gatctcccaa ggatgaaaga    1860
atgtcaagcc atgatggaaa tgccccttc caatcagctg ccttcacaag cagggatcag    1920
agcaactccc cggggatccc caatccacgc ccttctagtc caacccccct caatgagaga    1980
ggcaggcaga tctcacccag cactaggaca ccaggaggcc agggaaagca tctctggctc    2040
accatgtaac atctggcttg gagcaagtgg gtgttctgca caccaggcag ctgcacctca    2100
ctggatctag tgttgctgcg agtgacctca cttcagagcc cctctagcag agtggggcgg    2160
aagtcctgat ggttggtgtc catgaggtgg aag                                 2193
```

<210> SEQ ID NO 16
<211> LENGTH: 41
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 16
aaaaagctag ctgtttgagg ttgctagtga acacagttgt g                           41

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aaaaaaccgg tgctcgcttt cttgctgtc                                         29

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcaatgaaaa taaatgtttt ttattaggca gaatccagat g                           41

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
taatacgact cactataggg acattt                                            26

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
caaacagcta gccaccatg                                                    19

<210> SEQ ID NO 21
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
accggtgctc gc                                                           12

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
            oligonucleotide

<400> SEQUENCE: 22
taatacgact cactataggg                                                    20

<210> SEQ ID NO 23
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
taatacgact cactataggg acatttgctt ctgacacaac tgtg                         44
```

UNITED STATES PATENT AND TRADEMARK OFFICE
CERTIFICATE OF CORRECTION

Page 1 of 1

PATENT NO. : 10,837,020 B2
APPLICATION NO. : 13/455327
DATED : November 17, 2020
INVENTOR(S) : Mehmet Fatih Yanik et al.

It is certified that error appears in the above-identified patent and that said Letters Patent is hereby corrected as shown below:

In the Claims

In Claim 1, at Column 95, Line 36:
"…IFIT1, IFIT2, IFIT3; and…"
Should read:
--…IFIT1, IFIT2, and IFIT3; and…--

In Claim 13, at Column 96, Line 47:
"…encoded protein is Ascl 1…"
Should read:
--…encoded protein is Ascl1--

Signed and Sealed this
Twenty-fifth Day of May, 2021

Drew Hirshfeld
*Performing the Functions and Duties of the
Under Secretary of Commerce for Intellectual Property and
Director of the United States Patent and Trademark Office*